United States Patent [19]
Bro

[11] Patent Number: 5,722,418
[45] Date of Patent: Mar. 3, 1998

[54] METHOD FOR MEDIATING SOCIAL AND BEHAVIORAL PROCESSES IN MEDICINE AND BUSINESS THROUGH AN INTERACTIVE TELECOMMUNICATIONS GUIDANCE SYSTEM

[76] Inventor: L. William Bro, 8939 S. Sepulveda #530, Los Angeles, Calif. 90045

[21] Appl. No.: 315,630

[22] Filed: Sep. 30, 1994

Related U.S. Application Data

[63] Continuation of Ser. No. 112,955, Aug. 30, 1993, Pat. No. 5,377,258.
[51] Int. Cl.$^6$ .............................. A61B 5/021; A61B 5/04
[52] U.S. Cl. ...................... 128/732; 128/731; 128/630; 128/905; 128/920; 434/118; 482/9
[58] Field of Search ..................... 128/630, 637, 128/638, 670, 671, 731–733, 739–741, 904, 905, 920, 923; 434/236, 118, 365; 395/761; 370/449; 482/900, 901, 902, 8, 9

[56] References Cited

U.S. PATENT DOCUMENTS

| | | | |
|---|---|---|---|
| 3,742,938 | 7/1973 | Stern | 128/2.05 T |
| 3,808,694 | 5/1974 | Hutchinson et al. | 33/169 R |
| 4,112,425 | 9/1978 | Zobrist et al. | 340/347 AD |
| 4,237,344 | 12/1980 | Moore | 179/2 A |
| 4,328,494 | 5/1982 | Goodall | 340/870.18 |
| 4,377,214 | 3/1983 | Hansen et al. | 177/25 |
| 4,396,976 | 8/1983 | Hyatt | 364/167 |
| 4,602,127 | 7/1986 | Neely et al. | 179/2 A |
| 4,773,492 | 9/1988 | Ruzumma | 177/25 |
| 4,831,242 | 5/1989 | Englehardt et al. | 235/382 |
| 4,835,372 | 5/1989 | Gombrich et al. | 235/375 |
| 4,912,552 | 3/1990 | Allison, III et al. | 358/84 |
| 4,916,435 | 4/1990 | Fuller | 340/573 |
| 4,922,514 | 5/1990 | Bergeron et al. | 379/6 |
| 4,933,873 | 6/1990 | Kaufman et al. | 364/513.5 |
| 4,952,928 | 8/1990 | Carroll et al. | 340/825.54 |
| 5,008,835 | 4/1991 | Jachmann et al. | 364/513.5 |
| 5,014,298 | 5/1991 | Katz | 379/93 |
| 5,018,736 | 5/1991 | Pearson et al. | 273/439 |
| 5,023,901 | 6/1991 | Sloan et al. | 379/38 |

(List continued on next page.)

OTHER PUBLICATIONS

Mori, DeAnna L., "The Vulnerable Body Image of Females with Feelings of Depression," *Jrnl. Research and Personality* 25, 343–354 (1991).

(List continued on next page.)

*Primary Examiner*—Robert Nasser
*Assistant Examiner*—Stephen Huang
*Attorney, Agent, or Firm*—Cislo & Thomas

[57] ABSTRACT

A method for mediating social and behavioral influence processes through an interactive telecommunications guidance system for use in medicine and business (10) that utilizes an expert (200) such as a physician, counselor, manager, supervisor, trainer, or peer in association with a computer (16) that produces and sends a series of motivational messages and/or questions to a client, patient or employee (50) for changing or reinforcing a specific behavioral problem and goal management. The system (10) consists of a client database (12) and a client program (14) that includes for each client unique motivational messages and/or questions based on a model such as the transtheoretical model of change comprising the six stages of behavioral change (100) and the 14 processes of change (114), as interwining, interacting variables in the modification of health, mental health, and work site behaviors of the client or employee (50). The client program (14) in association with the expert (200) utilizes the associated 14 processes of change (114) to move the client (50) through one of the six stages of behavioral change (100) when appropriate by using a plurality of transmission and receiving means. The database and program are operated by a computer (16) that at preselected time periods sends the messages and/or questions to the client (50) through use of a variety of transmission means and furthermore selects a platform of behavioral issues that is to be addressed based on a given behavioral stage or goal (100) at a given time of day.

58 Claims, 4 Drawing Sheets

U.S. PATENT DOCUMENTS

| | | | |
|---|---|---|---|
| 5,036,462 | 7/1991 | Kaufman et al. | 364/413.01 |
| 5,038,800 | 8/1991 | Oba | 128/904 |
| 5,068,080 | 11/1991 | Impink, Jr. et al. | 376/215 |
| 5,085,527 | 2/1992 | Gilbert | 374/14 |
| 5,126,957 | 6/1992 | Kaufman et al. | 364/479 |
| 5,127,003 | 6/1992 | Doll, Jr. et al. | 370/110.1 |
| 5,142,484 | 8/1992 | Kaufmann et al. | 222/638 |
| 5,170,426 | 12/1992 | D'Alession et al. | 379/38 |
| 5,189,395 | 2/1993 | Mitchell | 340/539 |
| 5,206,897 | 4/1993 | Goudreau et al. | 379/38 |
| 5,218,344 | 6/1993 | Ricketts | 340/573 |
| 5,219,322 | 6/1993 | Weathers | 600/27 |
| 5,224,173 | 6/1993 | Kuhns et al. | 382/2 |
| 5,245,656 | 9/1993 | Loeb et al. | 380/23 |
| 5,462,051 | 10/1995 | Oka et al. | 128/630 |

OTHER PUBLICATIONS

Nelson, R. Eric and Craighead, W. Edward, "Selective Recall of Positive and Negative Feedback, Self–control Behaviors and Depression," *Jrnl. Abnormal Psych.* 1977, vol. 86 No. 4, 379–388.

Freeman, Walter J., "The Physiology of Perception," *Scientific American*, Feb., 1991, pp. 78–85.

Cann, Arnie and Ross, Debra A., "Olfactory Stimuli as Context Cues in Human Memory," American Jrnl. of Psychology, Spring 1989, vol. 102, No. 1, pp. 91–102.

Schab, Frank R., "Odors and Remembrance of Things Past," *Jrnl. Expmtl. Psych:Learning, Memory and Cognition* 1990, vol. 16, No. 4, 648–655.

Tulving, Endel & Thomson, Donald M., "Encoding Specificity and Retrieval PRocesses in Episodic Memory," *Psych. Rev.* 1973, vol. 80, No. 5, 352–373.

O'Hair, Dan and Cody, Michael J., "Gender and Vocal Stress Differences During Truthful and Deceptive Information Sequences," *Human Relations*, vol. 40, No. 1, 1987, pp. 1–14.

Ulett, George A.; Akpinar, Sevket and Itil, Turan M. "Quantitative EEG Analysis During Hypnosis," *Electroenceph. Clin. Neurophysiol.*, 1972, 33:361–368.

Blair, Alan J.; Lewis, Vivien J. and Booth, David A., "Responses to Leaflets About Eating and Shape by Women Concerned About Their Weight", *Behavioral Psychotherapy*, 1992, 20, 279–286.

Kearsley, Greg P. and Frost, Jana, "Design Factors for Successful Videodisc–Based Instruction," *Educational Technology*, Mar. 1985, pp. 7–13.

Jones, Loretta L. and Smith, Stanley C., "Lights, Camera, Reaction! The Interactive Videodisc:A Tool For Teaching Chemistry," *T.H.E. Journal*, 78 Mar. 1989.

McConnaughy, Eileen A., et al., "Stages of Change in Psychotherapy:A Folow–Up Report," *Psychotherapy*, vol., 26, Winter 1989 No. 4.

METHOD FOR MEDIATING SOCIAL AND BEHAVIORAL PROCESSES IN MEDICINE AND BUSINESS THROUGH AN INTERACTIVE TELECOMMUNICATIONS GUIDANCE SYSTEM

CROSS-REFERENCED RELATED APPLICATION

This application is a continuation of application Ser. No. 08/112,955 filed Aug. 30, 1993 (now U.S. Pat. No. 5,377,258 issued Dec. 27, 1994.

TECHNICAL FIELD

The invention pertains to the general field of information exchange services, in business, education and personal health care and more particularly to a computerized telecommunication system that conveys health awareness and goal management messages which maintain surveillance over patents, clients or employees by periodically sending behavioral motivation reinforcement messages and/or questions that require a patient's or employees interaction. In addition, the system uniquely utilizes social power through the avenue of telecommunications for modifying human behavior. It draws upon or is utilized by various authority figures or peers alternatively for modifying or reinforcing individual behavior. The invention can be supplemented by the addition of an additional expert or authority figure such as a physician or administrator to the system for providing interactive behavioral and motivational guidance to increase healthy behavioral changes to the patient or employee's prescribed medical regimens or work goals based upon his interaction over a period of time. Alternatively, peers or other persons of social influence may be added through its system to enhance each individual's performance.

BACKGROUND ART

One of the major advances of present-day society is in the field of computerized telecommunications. Today, in the growing fields of social psychology, behavioral medicine, and human motivation, formal verbal interchange is essential to provide modification of behavior and reinforcement. By using computerized telecommunications coupled with voice recognition technology, a client's or employees behavior can be modified and reinforced at the site where behavior occurs and wherever the client or employee goes. It has been found that as the frequency of reinforcing feedback increases, the client shows more rapid progress towards a particular goal. Similarly, the establishment of goals requires feedback and feedback requires goals, thus feedback is one of the key mechanisms in which goals are attained.

However, numerous studies have shown that feedback in itself does not have the power to motivate performance without the establishment of goals. By utilizing a system of continuous computerized reinforcement, a client or employee can be provided with more opportunity and greater frequency of therapeutic contact or feedback than through treatment or supervision in person. Additionally, the use of an interactive system vastly increases the therapeutic effect of this method of behavioral modification and reinforcement. As such, the subject invention uniquely mediates positive or beneficial expectancies of the physician, counselor, manager, administrator or other authority figure to the patient, client or employee.

Learning is enhanced through interactive feedback, and feedback in some form heightens the learning experience. The number of times in school a teacher asks any one child for an answer is fairly limited. Most of the time, children raise their hands and respond, and get back a "right" or "wrong." If they are wrong, they have lost their chance, and someone else is called upon for the answer. In traditional adult education, motivation and behavioral modification, the amount of continuing feedback is limited to the time actually spent with a counselor or supervisor, or in a class or seminar. Here, too, the feedback is limited to the actual time the physician, counselor, supervisor or trainer spends providing interaction with any one client or employee. By contrast, the addition of a computer and telecommunications or broadcast transmission allows "narrowcast" interaction and feedback on a continuous 24-hour basis to the client or employee wherever he goes, allowing for far greater frequency of interaction. Most importantly, in the case of adult behavior modification, this feedback, reinforcement and resulting motivation becomes available for the first time at the site where the behavior occurs.

Learning by playing and doing is fundamental to all mammals. While audio broadcast or telecommunications are media based upon hearing, and video broadcast is a medium based upon seeing, interactive feedback utilizing these architectures is a medium based upon doing or responding to the stimulus of feedback. Recent studies have revealed that the single best way to increase mammalian intelligence is through interactive stimulation. The frequency of feedback that we receive in relation to goals generally is the single greatest factor affecting learning, motivation and modifying behavior. Further, learning by receiving immediate feedback is preferable to receiving a delayed response. Children prefer interactive television games to merely watching a television program. They become impatient with long strings of dialogue, and the focus of their attention is diverted by devices providing rapid feedback. Adults display the same behavior throughout their lives. For example, when purchasing an appliance, they rarely read the instructions before trying to use it. The need to receive continuing feedback, at all levels of life, is a human characteristic, thus providing a basic survival mechanism which fosters learning and continuing growth. When feedback is combined with goals it becomes a powerful motivating force.

Research indicates that learning is enhanced by interactive feedback. Where the quantity of interactive feedback is increased, focus is sustained or increased, thereby stimulating keen responsiveness, as is the case with video games. The active involvement required to respond by answering provocative questions stimulates conscious awareness of and focus on the issue at hand. Learning, motivation and behavioral modification systems that incorporate rapid feedback foster problem-solving abilities, pattern recognition, management and allocation of resources, logical thinking patterns, memory, quick thinking, and reasoned judgment. Most importantly, when these skills are practiced at the site where the desired behavior is to occur, learning is more vivid and is quickly integrated into real life.

A sense of control is perceived with the provision of feedback. By engaging the client or employee to direct his focus and asking provoking questions, involvement is increased and stimulation results. When the individual learner achieves success and immediately receives positive feedback, self-esteem is rapidly built. When success is rewarded, confidence and resilience are enhanced and knowledge is created.

Historically, individuals have sought self-improvement, guidance and learning through self-help books, manuals, seminar workshops, personal counseling and programs of a periodic or short duration. With the best of intentions relapse usually occurs within several days after reading a book or attending a seminar, or several months after the conclusion of a behavioral modification program.

In contrast, computer-derived, self-adjusting motivational guidance, which interactively cues and polls the client and comments on his performance as he goes about his daily life throughout the year, has a more lasting effect. It differs importantly from seminars and visits to counselors or with a supervisor in that it modifies behavior at the site where the behavior occurs, with personal or customized intervention. The more frequent interactive dialogue between the counselor or supervisor-controlled computer and the client or employee enhances the feedback and therapeutic simulation in much the same way as has been experienced in other interactive communication structures, such as education and entertainment. For instance, consumers accord a higher value to interactive entertainment software than to passive software, due to the greater stimulation afforded by this mode. In entertainment software, an example would be some of the new video games that present a mode which runs like an animated cartoon until one elects to interact. As an animated cartoon, the video usually becomes boring within minutes. But as an interactive video game, the software stimulates the user with hours of entertainment.

In our culture, it is usually assumed that, given adequate information, people will use it rationally. Numerous studies have indicated that compliance with medical recommendations alone is less than perfect and generally only approaches 50 to 60 percent in many instances. Many physicians assume that if an individual is exposed to verbal information pertaining to his or her health issue, that behavioral change will take place. Given this viewpoint, the physician's responsibility is often seen as ending when the proper words are spoken. In fact, many problem behaviors and compliance with various medical requirements require constant feedback and adjustment over an extended period of time. Likewise, in other forms of education, personal management, sales and advertising, continuing reinforcement is often necessary to achieve the desired results.

Before a patient or employee can be expected to follow the intended recommendation of a physician, supervisor or counselor, he must have a thorough understanding of what is expected of him/her. One major criticism of contemporary medical care is that patients do not receive as much information as they would like. The resultant dissatisfaction precipitates a tendency to (1) ignore the physician's or counselor's recommendations, (2) forego follow-up appointments and (3) "shop" physicians rather than continue with one whom he feels is too vague.

In medical practice, initially, the physician must establish a baseline of the patient's knowledge to determine the extent of the patient's understanding, his grasp of the rationale behind the recommended behavioral changes, and his perception of the actions such changes will entail. It is important that the physician confirm the patient's understanding by having the patient repeat the explanations and instructions he has received, or by asking the patient to rephrase them in his own words. Too frequently, a physician will disregard this procedure because of time constraints or because he is uncomfortable doing so—circumstances that need to be addressed by the physician.

Of valuable assistance in successful behavioral modification is social or referent power, which is defined as the "primary basis of the social action becoming a significant other, a person whose approval and acceptance is highly regarded." Incorporating the use of social or referent power into a behavioral modification program entails three phases: (1) building, (2) using, and (3) retaining referent power.

Phase I is typically established during the physician/patient information-provision stage, during which the patient database is determined. Once established, referent power can be applied during Phase 2, with the physician offering both directives and encouragement to the patient.

Behavior modification necessitated by a medical condition requires that the patient subscribe to a particular medical regimen. Tailoring a regimen comprises (1) consideration of the various facets of the patient's existing routine and (2) modification of the regimen to minimize changes in the patient's lifestyle. The patient's cooperation is often proportionate to the degree of change demanded of him. If fewer behavior modifications are expected, the patient is more likely to adhere to the regimen.

The quality of the physician-patient relationship is critical to the success of a prescribed medical regimen, with the physician's interpersonal skills and manner central to the patient's perception of the physician. A patient responds to the forthcoming changes in his lifestyle emotionally; a physician responds professionally. The result is frequently a dissatisfied patient, one who sees his physician as unfriendly and uncaring. Equipped with this opinion, a patient is much less likely to heed the parameters of his regimen. The evolution of a therapeutic physician-patient alliance can only occur if the physician conveys—both verbally and nonverbally—his interest in the patient, vis a vis giving a patient the cathartic opportunity to tell his own story, expressions of respect, and empathetic concern.

In research literature on social power and influence, the degree to which patients comply with the recommendations of health care practitioners has often been seen as directly related to the physicians' use of referent, reward and coercive powers. Generally, medical recommendations are mentally internalized by patients based upon the regard in which they hold the caregiver and the continuation of some form of positive reward or reinforcer. However, in modern medical practice, physicians have shown that they generally lack the time, inclination or financial incentives for the continuing monitoring of a patient's behavior and compliance with the prescribed regime.

Therefore, a need exists for a computer driven interactive two-way communication link that increases the opportunity to create realistic and engaging behavioral reinforcement and guidance in the home or office and at remote locations, with both stationary and portable wired and wireless communication devices to assist the physician in the practice of medicine by facilitating compliance with medical requirements in regard to their patients. Similarly, a parallel situation exists in business organizations for the motivation of employees on a continuing basis in their natural environment.

Although in medicine, a physician is crucial to achieving permanent behavior change, other components of the primary health care organization are also important. Optimally, the physician-patient contact provokes a commitment from the patient and the initiation of a behavior modification program. Maintenance of such change necessitates methodical instruction, coaching, and protracted follow-up. For example, a patient diagnosed with chronic heart disease will require more than just prescribed medication. He will need to institute or revise his exercise regimen, relearn cooking habits, and appraise stress-inducing activities. Such extreme behavior modification will involve not just physician and patient, but nurses, clinic aids, conferences, and possibly educators, dieticians, social workers and psychologists.

Furthermore, psychotherapy outcome studies have been aimed at how people change their behavior, with and without the use of psychotherapy counseling. The results of these outcome studies have produced a number of definitive structures or models of the process of change that underlies both self-initiated and therapy-assisted modification of human behavior.

In the past, these processes have been administered ad hoc or randomly by various counselors and supervisors within verbal exchange processes, in person or through various methods including but not limited to bibliotherapy, direct telephone contact and counseling, group therapy sessions and seminars. Furthermore, it must be remembered that outpatients, on the average, spend about 99 percent of their waking week outside of a therapy situation. Therefore, in medicine there are advantages to having a medical regimen and behavioral guidance parallel those self change efforts or techniques that patients utilize outside of the physician's office into their daily lives. The disadvantages of the prior art are overcome by the present invention which provides a more comprehensive approach while affording greater convenience and increased interactive contact for physicians, psychotherapists and various counselors as well as supervisors, managers and administrators in a commercial setting.

Years ago, family physicians developed their social power to such a high degree that patients would strive to get well by compliance with his medical recommendations. Due to trends toward greater specialization, medical economics, and use of evolving technology, the physician house call has generally become no longer possible. The subject invention, by utilizing various telecommunication devices and computers, uniquely permits the greater personalization of medical treatment on a continuing basis. Today, physicians are not able to spend the time to make effective use of the variety of behavioral techniques available for motivating patient compliance. However, by the use of the present subject invention which extends the physician's recommendations and monitors their implementation uniquely through a counselor and computer, former patient rapport and affiliation can be reestablished. In the commercial marketplace, various supervisors can orchestrate and monitor employee goals by providing continuing feedback and guidance regardless of where they are located.

Therefore, a need exists to apply and distribute behavioral change processes, individually and collectively, through the medium of computerized telecommunication in association with a physician, manager or person of authority or influence. More particularly, this need is magnified due to the large number of variables and combinations in timing the administration of processes and behavioral changes throughout a given, prescribed medical regimen. The computerized administration and transmission of these social, behavioral and motivational processes, both separately and collectively, is a novel and unique advancement not known in the art.

In summary, a computerized interactive system increases the patient's or employees ability to resolve his medical or work problems at the site where his behavior occurs, and adjusts him within the framework of a preset goal. By including, within the context of the personalized message, challenges in the form of questions, an entertaining and stimulating process can be added due to the increased feedback or interactive nature of new telecommunication technology.

With regard to the prior art, many types of systems have endeavored to provide an effective means for providing surveillance over the behavioral modification of a patient or client by using a telecommunication link. However, these prior art systems have not disclosed an adequate and cost-effective telecommunication network that uses a computer in combination with a telephone or other platforms to provide positive behavioral based motivational messages and/or questions that are answered by a patient or client by means of a dual tone multifrequency telephone set or other platforms.

Further, the prior art systems have not disclosed utilization with such hardware as voice stress analyzers, on line services, olfactory units, CD-ROM platforms, interactive television in connection with a telecommunication link as a further behavioral modification means in use with the client or employee.

A search of the prior art discloses patents that show different types of feedback mechanisms:

| PATENT NO. | INVENTOR | ISSUED |
|---|---|---|
| 3,742,938 | T. J. Stern | 03 July 1973 |
| 3,808,694 | W. Y. Hutchinson et al. | 07 May 1974 |
| 4,112,425 | G. J. Zobrist et al. | 05 Sep. 1978 |
| 4,237,344 | Moore | 02 Dec. 1980 |
| 4,328,494 | R. Goodall | 04 May 1982 |
| 4,377,214 | G. G. Hansen et al. | 22 Mar. 1983 |
| 4,396,976 | G. P. Hyatt | 02 Aug. 1983 |
| 4,602,127 | J. F. Neely et al. | 22 July 1986 |
| 4,773,492 | E. Ruzumna | 27 Sep. 1988 |
| 4,831,242 | W. H. Englehardt et al. | 16 May 1989 |
| 4,835,372 | Gombrich et al. | 30 May 1989 |
| 4,916,435 | Fuller | 10 Apr. 1990 |
| 4,922,514 | Bergeron et al. | 01 May 1990 |
| 4,912,552 | Allison III et al. | 27 Mar. 1990 |
| 4,933,873 | Kaufman et al. | 12 June 1990 |
| 4,952,928 | G. T. Carroll et al. | 28 Aug. 1990 |
| 5,008,835 | Jackmann et al. | 16 Apr. 1991 |
| 5,014,298 | Katz | 07 May 1991 |
| 5,018,736 | Person et al. | 28 May 1991 |
| 5,023,901 | Sloan et al. | 11 June 1991 |
| 5,036,462 | Kaufman et al. | 30 July 1991 |
| 5,038,800 | K. Oba | 13 Aug. 1991 |
| 5,068,080 | Impink Jr. et al. | 26 Nov. 1991 |
| 5,085,527 | P. A. Gilbert | 04 Feb. 1992 |
| 5,126,957 | S. B. Kaufman, et al. | 30 June 1992 |
| 5,127,003 | W. J. Doll, Jr. et al. | 30 June 1992 |
| 5,142,484 | S. B. Kaufman, et al. | 25 Aug. 1992 |
| 5,170,426 | F. D. D'Alessio, et al. | 08 Dec. 1992 |
| 5,189,395 | M. S. Mitchell | 23 Feb. 1993 |
| 5,206,897 | N. Goudreau, et al. | 27 Apr. 1993 |
| 5,218,344 | J. G. Ricketts | 08 June 1993 |
| 5,219,322 | L. R. Weathers | 15 June 1993 |
| 5,224,173 | R. J. Kuhns, et al. | 29 June 1993 |
| 5,245,656 | S. K. Loeb, et al. | 14 Sep. 1993 |

The Sloan et al., patent discloses a surveillance system which integrates voice identification with passive monitoring mechanisms. The system comprises a central station located at a supervisory authority and a plurality of remote voice verification units. Each unit is located at a designated locality for an individual under surveillance and is connected to the central station via telephone lines. The central station consists of a control computer system and a violation computer system. The central station maintains and analyzes all relevant data for each individual, and initializes and retrieves information from each voice verification unit. Each voice verification unit conducts a voice verification test of a respective individual according to test schedules outlined by the central station. Test and monitoring results obtained during a defined surveillance period are transmitted to the central station on a periodic or exigent basis. Each remote station has a modem input, test means input connected to a microphone, and a third input to receive passive monitoring signals. The active and passive signals are analyzed according to an algorithm and command signals received from the central station. The test means also has an output to prod the individual to speak a preselected series of words. The test schedule in each remote is randomly created for each period and individual.

The Fuller patent discloses a remote confinement monitoring station and system with a central office that provides means for automatic selection of a specific confinee. The central office selects scheduled or semi-random monitoring calls, to avoid a high degree of predictability by the confinee, auto dialing means for transmission of a prerecorded or synthesized audio instruction message to the confinee, and recording of information received in response to the acts of the selected confinee preformed in response to the communicated message. The central office has a computer with a telephone line modem, a voice synthesizer, and other accessories and displays for automatic recording of data received including a visual camera image and breath analyzer results, and can include automatic image comparison and violation signal alarming.

The Moore patent discloses a rapid response hospital health care communications system. The system includes an auto dialer telephone system to allow patients to communicate from outside the hospital to receive advice and health care as indicated by the patient's medical profile. The communications system includes a health care console with an information storing computer connected through various communication paths to in-hospital patients, and by telephone means to out-of-hospital patient locations. Each out-of-hospital location includes a communication interface with a telephone, a console, and a hand-held remote control comprising a plurality of sensors, indicators and features. The interface includes an auto dialer and auto identifier that dials the health care console and identifies the patient by a computer recognizable code.

The Kaufman et al., patent discloses an interactive patient assisting device that has both preselected doses of medicine and a physical testing device that can communicate with a remote medical center over the telephone system. The system includes a clock/calendar unit that can be programmed to establish a schedule of a variety of activities, a pharmaceutical dispenser, a voice synthesizer and recognition unit, a computer, displays, and monitor means for blood pressure, oxygen and temperature. For communicating to a remote location, an automatic dialer, modem and telephone are included.

The Bergeron et al., patent discloses a method and system for the dispatch of resources to remote sites in response to alarm signals. A processor accesses the database of, for instance, a field service engineer designated to provide services to particular remote sites in response to the alarm signals received from those sites. The processor then attempts to establish a telephone connection with the field service engineer and provide the engineer with information by means of synthesized voice messages. The system may execute remote diagnostic programs and determine the results and attempt to communicate with selected resources. The system has a conventional processor with a database, voice synthesizer, voice system and auto dialer. When the system dials and the telephone is answered, the system requests an identification code by means of the touchtone buttons before it communicates.

The Hutchinson patent discloses a weighing and height measuring device. It is especially adapted for use with a remote digital read-out system. The device comprises a weight responsive moving platform connected by cable to a remote digital read-out unit. One of the objects of the invention is to provide a weight measuring device adapted for use with a remote read-out and/or computer input device.

The Stern patent discloses a cardiac pacer and heart pulse monitor for remote diagnosis wherein information from a pair of sensors is transmitted by means of a telephone handset and transmitter, over a commercial telephone system to a remote receiver. Information received at the receiver may then be processed by means of an appropriate computer and program system.

The Carroll patent discloses an adaptable electronic monitoring system. The system is configured to fit the needs of a particular monitoring or identification application by selecting appropriate modules. The system provides for monitoring at a central location and communication between the location of the sensed information to the processing site by means of a normal telephone communications system.

The Doll patent discloses a digital/audio interactive communications network. The digital network may be a wide area, metropolitan or local area network, and may communicate with other networks. The digital network ties a digital LAN server and an audio server together. The system works with software directed to a client/server architecture in an application that requires recording and playback of audio information.

The D'Alessio patent discloses a method and system for home incarceration using a telephone network and voice verification. The system has a control center with a process server connected to controllers through a LAN such as an ethernet or wide area network. New inmates are added by voice training so that the system can create voice templates of selected words. A data base of the voice templates and phone numbers, work schedules, etc. is created. Calls received are screened by using caller ID. Calls to and from the inmate are performed on a predetermined or random frequency, the frequency being a function of the patient's behavior. All activities are maintained in a log file.

The Ricketts patent discloses a method and system for monitoring personnel using computers and transceivers and a network. The interactive system monitors the identity and location of the inmates of a correctional facility, hospital, school or the like, and can alert the inmate that the inmate is entering a restricted area, or being approached by another inmate within a predetermined threshold distance. The inmate's transceiver can include a bar code for use of vending machines, telephone and the like, with the transactions being allowed or denied by the computer.

The Weathers patent discloses a psychotherapy apparatus and method for treating undesirable emotional arousal of a patient. The system presents visual and audio stimuli in each ear and eye separately and synchronously and alternately, the presentation being controlled in response to the patient's physiological responses to the stimuli. In addition to the behavior modification stimuli supplied to the patient by the computer, an operator, using a microphone, can direct the patient's attention.

The other cited patents are for background purposes and are indicative of the art to which the invention relates.

It will be noted that the above mechanisms and systems do not allow the utilization of various well known elements used in a unique random calling manner with a client, employee or patient database and client, employee or patient program of prescribed messages and/or questions for particular persons. More particularly, the instant apparatus and method provides a uniquely reinforcing approach of allowing the physician, person in authority, peer, or expert to use prescribed messages and/or questions for particular persons. More particularly, the instant apparatus and method provides a uniquely reinforcing approach of allowing the use of random calls at random locations from a list of possible locations where a client, employee or patient may be located. Furthermore, this system utilizes existing telecommunication technology including pagers, online services, etc., unlike many of the devices described in the above referenced patents.

SUMMARY OF THE INVENTION

The automated and interactive positive motivational system is designed to be used by doctors, psychologists, counselors, managers, administrators, peers or other trainers to provide motivational messages and/or questions to clients, employees and patients having behavioral and various addiction, volitional or motivation problems. Its basic configuration comprises:

(a) means for recording and accessing a patient's database that includes for each patient the name, schedule of telephone numbers where the patient may be reached during each 24-hour period, personal identification number, and previous history of messages and the patient's responses;

(b) means for measuring and recording a patient's weight without revealing their weight to them and transmitting said weight information telephonically for use in a weight reduction program;

(c) first means for recording and accessing a patient's or employees program that includes for each patient or employee specific motivational messages, personal and unique metaphoric references, goals, and/or questions that are to be responded to by the patient or employee through either the telephone, one- or two-way interactive beeper, personal communicator, modem, personal computer, or interactive television;

(d) a computer having means for accessing the patient database and said patient or employee program. If a match is found between a patient's or employee's database and patient or employee's program, the computer produces a sequence, a digital telephone signal which corresponds to his telephone number or beeper or personal communicator number, a digital patient or employee validation request signal and a digital motivational message(s) and/or questions. The messages and/or questions are only then sent if the patient's or employee's validation request signal is responded to by the patient with a valid personal identification number (PIN) in the telephone mode, or broadcast without a PIN with a beeper or personal communicator;

(e) means for converting the digital signals produced by the computer to telephone tone signals that are sent to a patient's dual tone multifrequency telephone set or computer and modem via a telephone network. The telephone set or a computer is used to respond to the computer's validation request, hear the motivational message(s) and/or to respond to the questions;

(f) means for converting the telephone tone signals originating at the patient's telephone set, personal computer, or hand-held wireless device, to digital signals for application to and processing by the host computer; and (g) second means for permanently recording all the outgoing and incoming patient or employee communications.

An important object of the invention is that the system manipulates speech messages that are stored, not in an analog format common to audio tape storage systems, but in digital format that is stored on a read-only compact disc, a computer hard drive or the like. The use of compact discs allows the system to access files quickly and accurately. Therefore, it is possible for the computer to access more than one speech file at a time. Each telephone line that the system is servicing is actually a small "slice" of computer time during which speech files are being played from or recorded. The more lines that are active, the more slices of time that must be managed. The system provides the functions to operate with more than one telephone line simultaneously, thereby allowing a physician, manager or other counselor, at all times over a 24-hour period, to process and supervise many more patients or employees than otherwise. In addition, the system allows for a patient or employee to receive more doses of behavioral intervention over any time period than in any other manner.

Another object of the invention is directed to accomplishing most tasks in a voice response application by accepting, recognizing and making decisions based on a keypad input from the caller's dual tone multifrequency telephone or computer. The telephone keypad generally sends dual tone multifrequency (DTMF) tone signals but occasionally multifrequency (MF) tones are used by certain types of telephone switching equipment. While these two signalling methods are not compatible, the system will work with either one equally well.

Still another object of the invention is the use of digitized voice signals for the transmission of messages to the patient or employee. Digitized voice signals are typically made by sampling the voice wave form 6000 to 8000 times per second in order to accurately reconstruct good speech quality. Each sample takes 8 to 12 bits, this results in 48,000 to 96,000 bits of information per second that must be stored. It is common in telephonic applications for a digitized voice to be compressed by storing only the differences between samples. Therefore, the speech card that the system supports uses a compression technique known as Adaptive Differential Pulse Code Modulation (ADPCM) which recognizes that there is only a small difference between the speech samples and stores a logarithmic function of the difference between speech samples. The result is good speech quality at only 3000 bytes per second of data throughput.

Yet still another object of the invention is the utilization of an expert, such as a physician or authority figure, to a system of behavioral motivation and guidance which adds an additional dimension of support and, most importantly, increases the impact of the intervention. Often, individuals regard certain "experts" with elevated respect and regard their advice with increased attention. Various categories of experts, such as doctors, educators, scientists, and public personalities, are attributed elevated or enhanced knowledge by the public at large and their recommendations and advice are accorded greater recognition and enhanced value. Today in modern commerce, recommendations and endorsements by experts and public personalities are traded for monetary value in recognition of their value in facilitating the sale of goods and services to consumers. Likewise, in the practice of medicine, the recommendation of a physician is generally accorded higher import to a patient than that of a layman. In the field of commerce, a parallel example would be that of a person of influence who sits higher in hierarchy of his employer than that of his immediate superior. Alternatively, peers mediate social influence through their equalitarian or reciprocal relationships.

Therefore, the present invention involves a method to increase the impact of various behavioral modification formats, delivered by telecommunications, and administered by one or more computers. uniquely extends the prior art of physician counseling and sales, marketing and personal management techniques by the addition of an "expert" who is regarded by the patient, consumer or employee with a degree of respect or regard at appropriate or strategic times during the behavioral process or intervention. In addition, it provides for the addition of peer influence for additional reinforcement and support.

Yet, another object of the invention is that the patient or employee program may be directed to any subject matter such as motivational training, teaching, psychological behavior modification, and reinforcement of a medical regimen, wherever motivations would be facilitated by daily or periodic intervention. The following is a partial list of some of the component areas that the patient or employee program may be directed to:

1. nutrition
2. exercise
3. weight loss (diet/weight management)
4. optimism (and hope)
5. life-long learning
6. time management
7. stress management
8. optimal health management
9. immune system enhancement
10. midlife transformation/emergence
11. women and men in aging and transition (heart disease, menopause, etc.)
12. control or self-discipline
13. compliance with medical requirements
14. pain control
15. anger management
16. acceptance of mortality
17. reforming the concept of aging
18. memory management
19. reformation of self-destructive behavior
20. transformation of regret
21. anxiety management
22. mental and physical resilience
23. early cancer screening and detection
24. an interactive journal
25. wake up and sleep meditations
26. control of performance anxiety and mental rehearsal
27. enhanced self-esteem
28. Short and long term goal management Accordingly it is an object of the present invention to record the daily or periodic activity schedule of each patient or employee enabling contact with the patient or employee on a scheduled or random basis by telephone, personal computer or other means such as a wireless alpha-numeric pager, laptop computer, personal communicator, cellular phone, or modem that is used to contact patients or employees wherever they may be during the day or night. If the patient or employee misses a call, they may call in to the computer and get their message by using a specific password.

Yet a further object of the invention is that the patient or employee program in association with the use of an expert or authority figure will utilize one of several types of behavioral modification techniques. By way of example, but not of limitation, one such behavioral modification technique used may be the transtheoretical model of change comprising the six stages of behavioral change and the 14 processes of change, as interwining and interacting variables in the modification of health and mental health behaviors of the patient. These six invariant stages of behavioral change, which have been identified and to which the patient program may be directed, are:

1. Precontemplation
2. Contemplation
3. Preparation
4. Action
5. Maintenance
6. Relapse The patient program further includes the associated 14 processes of change utilized to move the patient through the six stages of behavioral change. The following is a list of these 14 process areas that the patient program may be directed to:

A. Consciousness raising
B. Self Liberation
C. Social Liberation
D. Self re-evaluation
E. Environmental re-evaluation
F. Counter conditioning
G. Stimulus control
H. Reinforcement management
I. Dramatic relief
J. Helping relationships
K. Self efficacy
L. Temptations to relapse
M. Decisional pros
N. Decisional cons The object of the present invention is to utilize these 14 processes within the previously cited six behavioral stages of individual growth, through computerized management and administration, by initiating prompts and cues and related educational material for guidance and reinforcement by the patient or employee program in association with the use of an expert or authority figure in addition to that of his supervisor, counselor or trainer.

Another object of the invention is that the use of an expert and the patient program may be directed to the field of chronic disease detection. More particularly, the patient program will provide periodic behavioral cues to aid the expert in the early diagnosis and cure of such chronic diseases as glaucoma, dental and periodontal disease, cancer, heart disease, and diabetes.

Still yet another object of the present invention is the use of the patient program to address issues for the management of such chronic diseases as diabetes, hypertension, and others where compliance with the expert's suggested medical regimen can be critical. By applying the aforementioned transtheoretical model, the patient program will provide the gradual courage to overcome individual resistance and to reinforce periodic self and physician examinations while extending the relationship with the expert in a manner heretofore not known.

Yet another object of the present invention shall be the formulation and publication of individually customized information in the form of reports, or graphs, indicating performance and response profiles, educational monographs, and tutorials and other materials necessary for providing motivation and education for use by both the counselor, expert and the patient or employee. By storing in a data base memory device a group of prerecorded informational data of a generalized nature and accumulating personal response profiles in said memory device, it is possible to mix or formulate a customized set of unique and individual printed educational and medical record documents.

Another object of the present invention would be that for each individual patient or employee, based upon his education, gender, age, demographic profile, psychological profile and prior response profiles, an educational document and text would be formulated according to the individual's present behavioral stage.

A further object of the present invention is to provide a large central mainframe computer or interconnected series of personal computers containing a multiplicity of microprocessors which could be used by local or regional clinics and hospitals for interactive, telecommunication and/or multivideo transmission for enabling thousands of individual patients to be provided interactive medical guidance and feedback in real time or delayed service, whereby a hospital may currently serve a greater outpatient population in its locality and place increasing emphasis on home health care.

Another object of the present invention is to use higher capacity transfer modes of transmission such as asynchronous transfer mode (ATM) and Integrated Services Digital Network (ISDN) as an alternative method of transmission for behavioral guidance and motivational reinforcement. Since the present invention relies upon telecommunications which are transmitted or delivered synchronously, this alternative embodiment relates to the asynchronous transmission of information by both wire and wireless means in private and public networks. Therefore, an additional object of the present invention is to use such higher capacity transfer modes as asynchronous transfer mode and ISDN for both data and real time and delayed transmissions; as an example, voice and video wherein it is equally adaptable to both local and wide area networks.

The rationale of the system is that man is in a continuous state of growth and development. The system provides the motivation and reinforcement through continuous daily monitoring of each patient as he works towards his basic goals for optimal health by maintaining prescribed regimens or goals. By this daily or periodic reinforcement and guidance utilizing interactive feedback, the system is able to maintain the organization and intervention between the physician, counselor, manager, the patient, or employee and his or her goals.

By mobilizing patients to accept responsibility for their own health through behavioral guidance in preventive health programs and to comply with medical prescriptions in the dispensing and taking of medicines, large savings can thereby be realized, contributing to national goals of medical cost containment. The aging of the population necessitates greater health care expenditures which in turn are aggravated by the possibility of older individuals having one or more chronic diseases wherein non-compliance with medical regimens can become financially costly, dangerous and even life-threatening. Likewise, large savings can accrue by keeping employees motivated and focused on assigned goals.

These and other objects and advantages of the present invention will become apparent from the subsequent detailed description of the preferred embodiment and the appended claims taken in conjunction with the accompanying drawings.

DESCRIPTION OF THE PREFERRED EMBODIMENT

Figure 1:
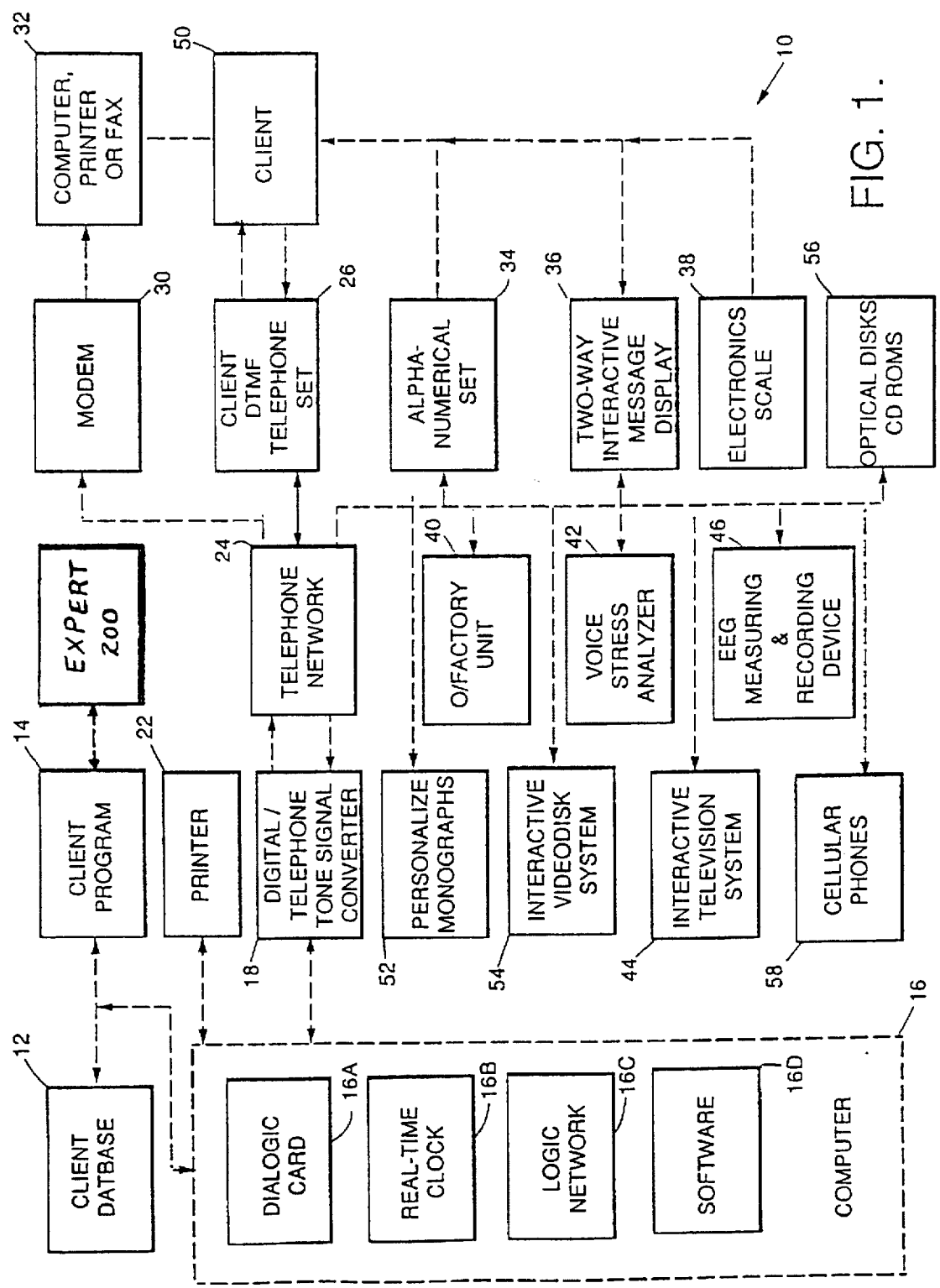
FIG. 1 is a block diagram showing the interactive activity between the system and a patient, client or employee.

An optimal best mode for carrying out the invention is presented in terms of a preferred embodiment that is designed to allow doctors, psychologists, counselors, managers, peers and other trainers to maintain surveillance over their patients or employees by utilizing a wired or wireless telecommunication link to perform automated information exchange. The preferred embodiment of the interactive social process guidance system 10, as shown in FIG. 1, comprises a means for recording and accessing a patient's or employee's database 12 and a patient's or employee's program 14, by using a computer 16, having a digital signal/telephone tone converter 18 and a printer 22, wherein access means comprise a telephone or other wired or wireless telecommunications network 24 and a patient or employee dual tone multifrequency telephone set 26. A patient or employee 50 uses the system 10 which can also be enhanced by the incorporation of the following elements that are operated by the aforesaid network 26: a modem 30 that operates a computer printer or facsimile machine 32, an alpha-numeric one-way or two-way pager 34, a two-way interactive message device 36, an electronics scale 38, an olfactory unit 40, a voice stress analyzer 42, an interactive television system or personal computer 44, an EEG or blood sugar or blood pressure or heart monitor or cholesterol measuring and recording device 46, general or personalized monographs, interactive video, optical discs, i.e., CD-ROMs, cellular phones, and a timing device 47 for measuring response latency.

The patient or employee database 12 in the preferred embodiment consists of a compact disc (CD) recording that is played back on a CD player that interfaces with the computer 16 as shown in FIG. 1. However, other database recording and playback units can also be used. By way of example but not of limitation, these units include but are not limited to hard disks or other random access memory devices or a tape cartridge that is played back to the computer by means of a tape cartridge player or an optical disc and optical disc playback unit. The patient, client or employee database includes for each patient or employee 50, the patient's, client's or employee's name, their calling schedule by week, day and time, each patient's or employee's personal identification number (PIN), and previous history of messages received and response profiles.

The patient, client or employee program 14 in the preferred embodiment, is also recorded and played back by a CD player or other recording and/or playback units, as described above for the patient, client or employee database 12, and is connected to the computer 16 and to the telecommunications network 24 as shown in FIG. 1. The patient or employee program 14 is especially designed to serve a plurality of specific patients or employees. The program 14 can include as many motivational and reinforcement messages as are necessary to help with a specific behavioral problem. The motivational and reinforcement messages are designed to provide therapeutic or behavioral intervention at specific or random times and more particularly to provide therapeutic intervention at the site and appropriate time where the behavior to be corrected occurs. In the field of behavioral guidance and reinforcement it has been found that even with the best of intentions, relapses usually occur within several days following the reading of a book or attending a seminar to several months after the conclusion of a behavioral modification program. Thus, by transmitting feedback or progress towards goals plus behavioral motivation and reinforcement messages on a periodic or random basis, the behavioral modification program can continue on course to a curable or successful conclusion.

In addition to or in combination with the messages, the system 10 is also designed to send a patient or employee behavioral modification queries or polling questions. These questions may be answered by the patient or employee by pressing on a specific key on the keypad of the dual tone multifrequency telephone set, computer keyboard, touch-screen 26 or by use of a speech recognition device. The answers to the questions are analyzed by the patient's or employees doctor or trainer to find root problems and to determine the next series of messages and/or questions that are to be transmitted to him or her 50 at the next transmittal period. All messages, questions and the patient's or employee's response to the questions as well as the time, date, duration of each call and touch tones entered by the patient or employee 50 are retained in a permanent log or record by means of the printer or other type of storage device 22 which is directly connected to the computer 16 as shown in FIG. 1.

The telephone by its very nature, has always been interactive on a two-way basis and because of its wide usage it lies within the comfort zone of nearly all patients. The telephone is also cost effective and is convenient for both the caller and the patient. Additionally, social learning theories suggest that education carried out in the setting in which the behavior is taking place will have the greatest impact. Thus, telephone counseling at home or in the work place may have greater behavioral impact and relevance than that within the clinic. For patients who cannot come to a clinic because of their physical condition, distance or the presence of a psychiatric disorder that makes the intimacy of face-to-face contact intolerable, the telephone or other remote communications device is the sole available means for counseling. By calling patients on their transportable cellular telephones or other portable communication devices 58, behavioral reinforcement can also be provided for busy patients on the go and increase the instances wherein motivation can be provided in the place where the behavior occurs. In a similar manner, employees can benefit by the usage of such a system for motivation in the workplace.

The patient or employee database 12 and patient program 14 interface with the computer 16 that in the preferred embodiment consists of a personal computer. The patient or employee database 12 and patient or employee program 14 as described above, are externally stored as shown in FIG. 1. However, these elements may also be stored on a hard disc located within the computer 16 or on other mass media storage devices such as CD-ROM, writable optical media, or removable mass media cartridges. The computer 16 is configured in part to include a speech card such as a Dialogic D41 4-line or larger 16A, having a real-time clock 16B and a logic network 16C, operated by the system software 16D.

The Dialogic type card or other similar device 16A allows a speech compression technique to be used that samples a small difference between speech samples and stores a logarithmic function of the difference between the speech samples. This technique results in good speech quality at only 3000 bytes per second. The real-time clock 16B sets and selects the appropriate time for a particular patient to be accessed from the patient database 12 and the patient program 14. The logic network 16C provides the logic necessary to determine if a match between the patient or employee stored in the database 12 and in the patient or employee program 14 is available. The system software 16D provides the algorithms to operate the system 10 in combination with the logic network 16C. The operating steps of the software program are shown in the software flowchart included as FIGS. 2A and 2B.

Figure 2A:
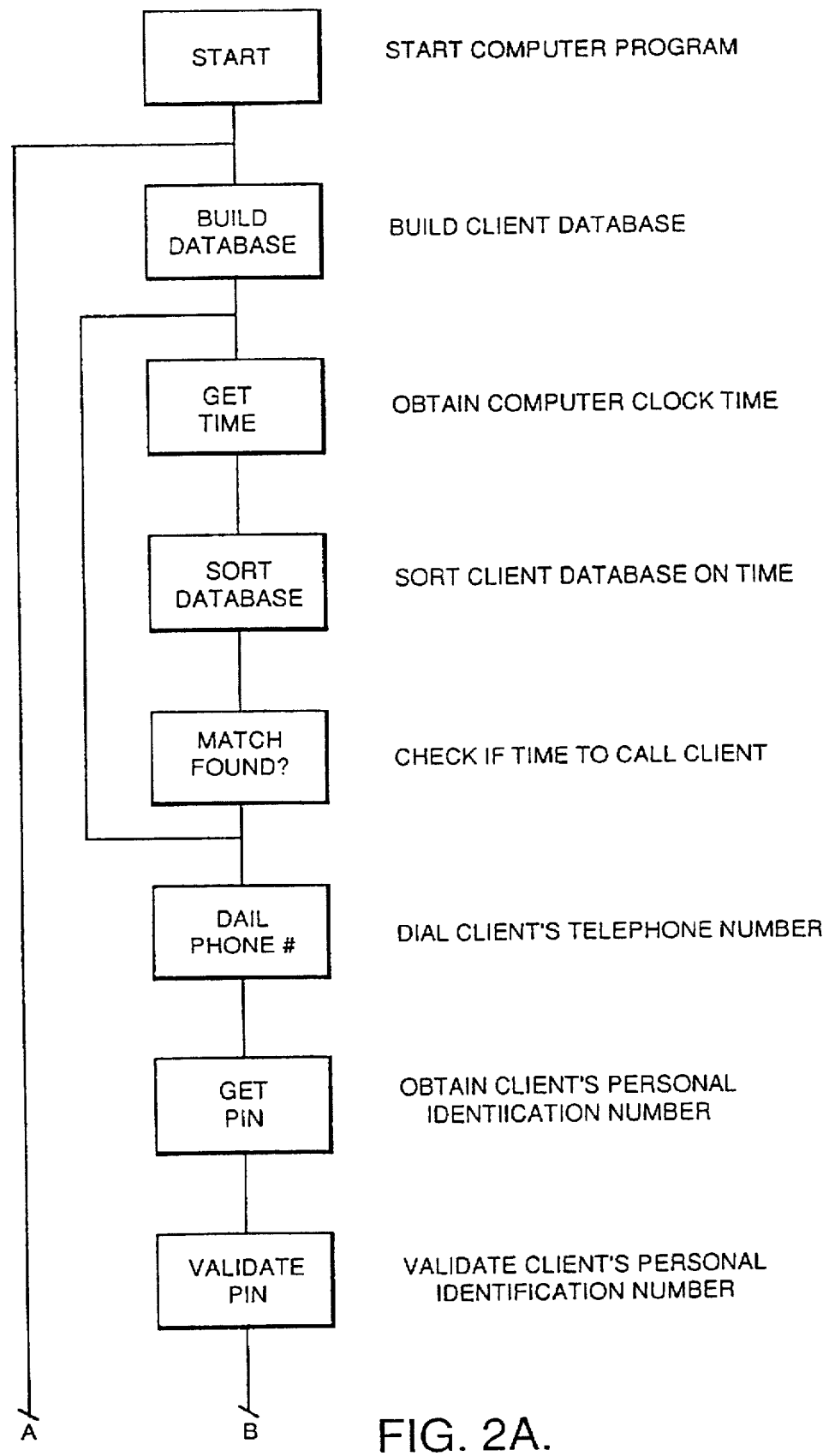
FIG. 2A is an application flowchart of the computer software program.
Figure 2B:
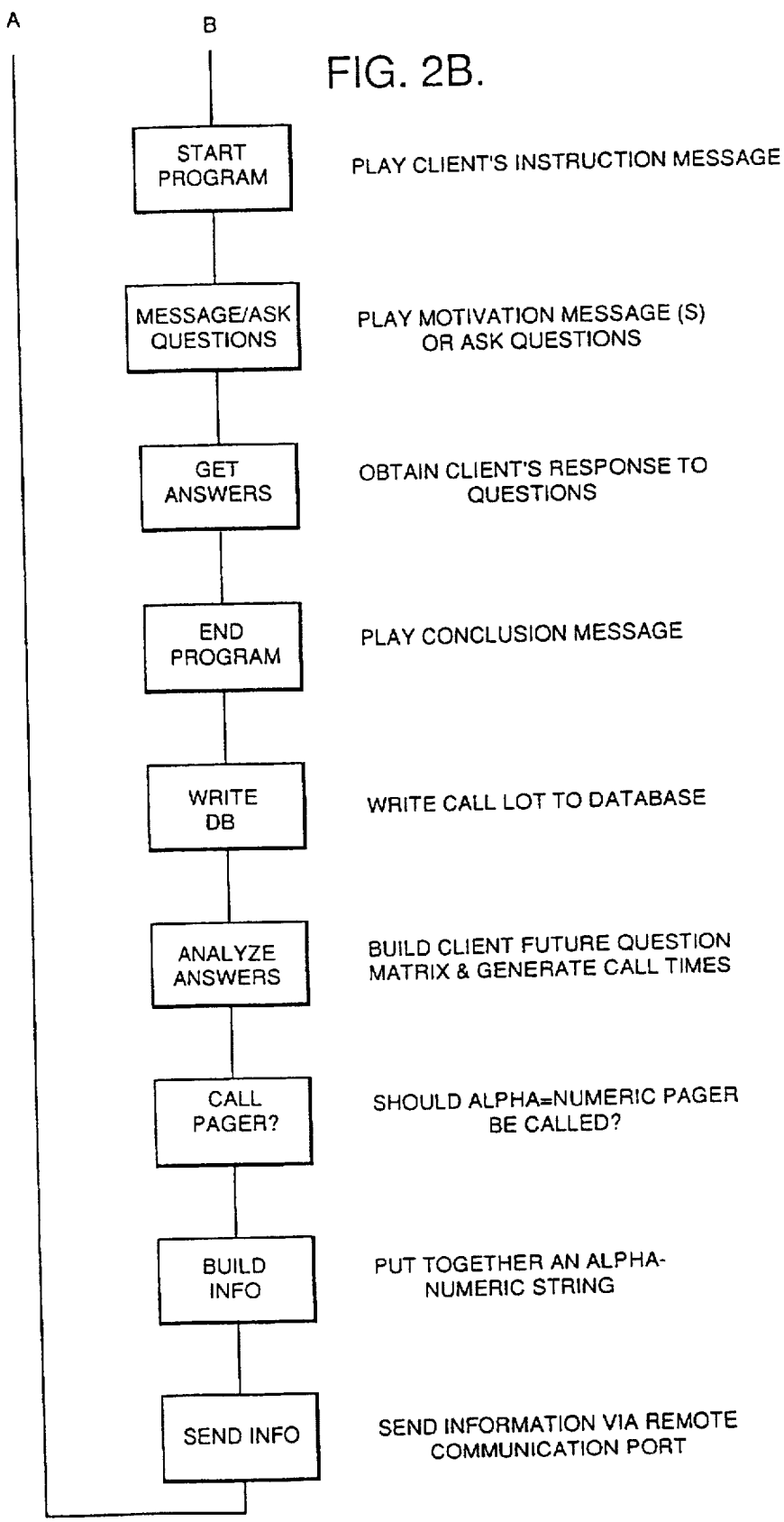
FIG. 2B is a continuation of the application flowchart of FIG. 2A.

As shown in FIGS. 2A and 2B, the computer program builds a patient or employee database and sets the database to a computer clock time. In a typical operating sequence, the computer 16 at a preselected week and time, accesses the patient or employee database 12 and the patient or employee program 14. If a match is found between the patient's or employee's database entry 12 and program 14, the computer 16 via the logic network 16C, produces in sequence, a digital telephone number and a digital patient or employee validation request signal.

Both of these signals are applied to the digital signal/telephone tone signal converter 18. The converter 18 includes circuit means to accept and convert the digital signals from the computer 16 to telephone tone signals that correspond to the patient's or employee's telephone number and a personal identification number. The converter 18 can also be designed to include a telephone number redial circuit and a random telephone number dialer circuit. The redial circuit allows a patient's or employee's busy telephone number to be automatically re-dialed at selectable time intervals. The random number dialer allows patient or employee telephone numbers stored in the patient or employee database 12 to be randomly selected and called.

From the digital signal/telephone tone signal converter 18, the telephone tone signals are applied as shown in FIG. 1 to a telephone network 24. The network 24 relays the tone signals to the patient's or employee's dual tone multifrequency telephone set 26 from where the patient or employee 50 can answer the telephone 26 and respond to the request to provide a personal identification number. The patient or employee 50 responds by pressing on specific keys on the keypad of the telephone set 26. If the patient or employee 50 responds with a valid number it is routed via the telephone network 24, back through the converter 18 to the logic network 16C in the computer 16. Upon the receipt of a valid number, the logic network 16C enables the patient or employee program 14 to allow the audio signals carrying the messages and/or questions to be transmitted via the telephone network 24 to the patient's or employee's telephone or computer 26 from where the patient or employee 50 can receive the message and respond to the questions.

The telephone network 24 used in the preferred embodiment is serviced by the local telephone public utility company, or cable company supplying telephone. However, if a closed circuit operation is desired, such as within the confines of a network, an enclosed area or building, a private telephone network or Local Area Network (LAN) may be employed. In either of the above scenarios the patient's or employee's dual tone multifrequency telephone set 26 may be hardwired to the telephone network 24 or, a transportable cellular 58 or a two-way pager 34 that uses RF or satellite communication links may be used. By calling a patient or employee 50 on their transportable cellular telephone or other device 58, the motivation message can in many instances be sent to the place where the behavior is occurring when the message carries its greatest effect. As also shown in FIG. 1 by dotted lines, in lieu of making the initial patient or employee contact by using the telephone set 26, the contact can be made by means of a modem 30, an alphanumeric pager 34, a two-way, interactive, computer activated message display 37 or other such devices. If a modem 30 is used, it can be connected directly to a computer printer or facsimile machine (FAX), text screen telephone or on-line system 32. In this patient or employee alerting medium, after the patient or employee 50 receives a motivational message or a question, the patient 50 response can be made by calling the computer 16 on the dual tone multifrequency telephone 26 by use of a special computer access telephone number. Likewise, if an alpha-numeric pager 34 is used the patient or employee response would be made as previously described.

The use of a two-way interactive message display 36 further provides an enhanced patient or employee interface in that text and graphics can be included with the messages and questions. The display 36 is connected directly to the computer 16 via the telephone network 24 and digital/telephone tone signal converter 18. Additionally, screen and textual media position the software developed hereunder for future interactive television and multimedia applications when they commercially appear and may be added to the system.

Although not shown, it may be envisioned in one embodiment that a one-way or two-way, interactive message display 36 be in the form and design of a ladies' compact containing a mirror. The compact 36 comprises a small screen for the reception of alpha/numeric data which it receives over existing paging networks, and in addition, as an option, it may receive wireless voice transmission over a built-in speaker. For transmission purposes, in one embodiment, the compact 36 comprises four (4) response buttons which allow the patient 50 to respond to the messages and questions received either as data on the alpha/numeric screen or as audio transmission from the built-in speaker. In use, the compact 36 would utilize the before described cellular wireless, PCS or PCS modes and would operate on either analog or digital transmission.

Another embodiment would be a wrist communicator which would be used for providing behavioral modification through a one-way or two-way interactive message display 36 and designed to be attached to the wrist with a flexible band. The aforesaid device would receive data from paging networks or via wireless transmission and display the data on an alpha-numeric screen. For transmission purposes, the wrist unit 36 would contain response buttons, allowing the patient or employee 50 to respond to messages and polling questions transmitted from the personal communication device or via cellular transmission. Both the aforesaid ladies' compact 36 and the wrist unit 36 could operate through a variety of transmission modes in either analog or digital format.

Additionally, a unique software program which is commercially available instructs the computer to send text messages which are encoded to activate special software algorithms contained within the computer 16 receiving the messages via the modem 30. This special software contained in the receiving computer will activate either internal or external speakers or telephone handset in order that the text messages may be heard as the text scrolls across the screen. The sound emphasizes and enhances the text presentation, or the patient or employee 50 may choose to listen and not read the text while performing other tasks.

Likewise, an interactive television system 44 can be used wherein customized broadcasts can be responded to by individual patients or whole classes of subscribers, providing a low cost alternative to individual customized instruction. In addition to or in lieu of an interactive television system 44, an interactive videodisc system 54 comprising a videodisc player or similar means such as a CD-ROM or the like and monitor interfaced with a microcomputer may be used.

Additionally, the aforementioned speaking screen embodiment is equally applicable to all screen media, such as the aforementioned interactive television, screen telephones, personal digital assistants, communicators and computer terminals.

Alternatively, the aforementioned interactive data communications may be performed by asynchronous transfer mode or other high capacity transfer modes in addition to the currently available transfer mode commonly used to transmit digitized voice. The asynchronous transfer mode is one of a general class of digital packet switching technologies that relay and route traffic by means of an address contained within a very short, fixed-length packet referred to in the industry as a cell. Therefore, it is envisioned that the system 10 may utilize a packet switching technology as the aforementioned asynchronous transfer mode to route traffic by means of addresses contained within packets, in contrast to the transfer modes or technologies that route data over dedicated physical paths that are established during call set-up and remain fixed for the duration of a call. With the system 10 using asynchronous transfer mode, the creation of local area networks or LANs can be used for the mounting volume of traffic generated by the current patient or employee behavioral program. Moreover, unlike other transfer modes, an asynchronous transfer mode provides two further benefits: (1) it positions local area networks for future multimedia applications if they appear when more patients or employees are added to the system, and (2) it seamlessly integrates local traffic into the future wide area asynchronous transfer mode network.

With the use of optical discs or CD-ROMs 56, CDI and similar devices a computer-based information metering system is envisioned wherein a patient 50 may be billed through the use of an encryption-metering device only for amount of therapy the patient 50 wishes to access.

The motivation and behavioral messages and patient questions can also be used in combination with auxiliary devices to fortify the patient's messages or questions and provide feedback to the physician or counselor. For example, in the field of weight loss, an electronics scale 38 can be utilized to supply the timely weight of the patient to determine if a weight loss or gain has occurred during the reporting period. As shown in FIG. 1, the electronic weight scale is connected to an ordinary telephone line which automatically dials the telephone number associated with the operating system and transmits the weight of a patient 50 standing on the scale 38 digitally to the patient's program 14 and database 12 for later feedback and analysis in accordance with a weight reduction program.

The scale 38 prevents the patient 50 from becoming aware of their day-to-day weight fluctuations. This is consistent with new insights in behavior theory with respect to human motivation which allow an observer or instructor using the computer to review the patient's weight periodically through the use of the computer 16 which is at a remote location and can guide the patient 50 from time to time based upon the trend or average of their weight, and other devices such as glucose monitoring, blood pressure, heart rate, and cholesterol monitoring.

Yet another preferred embodiment shown in FIG. 1 incorporates the use of a voice stress analyzer 42, which offers a digital numerical evaluation of the speaker's voice stress level to monitor a patient's or employee's response during a behavioral motivation reinforcement question. Research by D. O'Hair and M. J. Cody entitled "Gender and vocal stress differences during truthful and deception information sequences," in *Human Relations*, Vol. 40, 1–14 (1987), indicates that voice stress analyzers can be objectively and unobtrusively used to detect vocal stress indicative of deception. If a patient or employee 50 knows that his veracity is being tested and that his responses are being analyzed for deception, then there is greater motivation on his part to adhere to the program 14 and hence more rapidly progress towards a particular goal. In addition, commonly encountered self-deception is reduced using this mode.

Yet another preferred embodiment would be a timing means which would be started at the end of a polling question. The timing means would be stopped upon commencement of the patient's or employee's response and the interval between the end of the question and the commencement of the response would be recorded. While polling is often useful as a means of determining a patient's or employee's progress, or lack thereof, it is extremely difficult to determine on the basis of traditional methods whether the response is based on an actual occurrence or feeling of the patient or employee 50 or whether it is fabricated on the spot for the purpose of providing an answer. In the former case, it is common to think of the attitude as being pre-integrated and crystallized and thus quite stable, whereas in the latter case the response represents an improvisation or may be lacking veracity. By first observing the patient's or employee's base line or time to respond to questions of known behavior or fact a typical observable pattern emerges. Later his pattern can be compared to the latency in response time to questions of unknown veracity. By measuring and observing the patient's or employee's latency response interval over a period of time, useful clues and insights emerge which can be used to assess and predict more accurately the degree of crystallization of a person's attitudes and resulting behavior. Such a latency response measuring tool could also be utilized in conjunction while a live counselor or manager is working in real time with the patient or employee 50.

This embodiment could be utilized in conjunction with any of the cited means herein of communicating polling questions. It is a unique application of determining latency of response to computerized behavioral reinforcement in order to determine the relative degree of crystallization of gradually learned behavior. A further advantage is that such method and apparatus would be transparent from the perspective of the respondent.

Another preferred embodiment incorporates the use of an EEG measuring and recording device 46 which can be used to assess hypnotic susceptibility either in the presence of the patient 50 or at some distance by use of a modem for transmitting signals which indicate various brainwave states. Behavior research indicates that there is an increase in alpha activity in the EEG when subjects are exposed to behavioral intervention techniques such as hypnosis, relaxation and meditation. In addition, studies with psychotropic drugs have demonstrated that increased and synchronized alpha activity is a characteristic of all the major tranquilizers. A 1972 study by G. A. Ulett, S. Akpinar and T. M. Itil ("Quantative EEG analysis during hypnosis," *Electroencephalography and Clinical Neurophysiology*, Vol. 33, 361–368) reported significant EEG differences between the hypnotic and awake states, with all subjects experiencing increased alpha activity in the hypnotic state. The computer 16 in this mode, receiving and analyzing the signals, can then adjust the intervention to correspond to the patient's 50 brainwave state.

Another preferred embodiment shown in FIG. 1, is a computer-driven system for behavioral and motivational reinforcement and guidance which can be applied to various modes of interactive television 44. Its feature of providing customized instruction, learning, and motivational prompts and cues, often where the behavior occurs, provides a unique approach toward directed interactive learning and behavior modification. Using interactive television 44, the computer-driven system converts the traditional broadcast format to a customized "narrowcast," where either classes of learners or individual subscribers are addressed according to their individual issues without specific categories, and each in turn returns individual specific responses to questions or polling, which are then recorded in the patient or employee database 12. This application becomes possible because of the larger number of channels available with fiber optic cable, wireless transmission or a combination of both facilitating two-way interaction.

It is envisioned that three separate modes of transmission from a computer with interactive television can be utilized:

(1) fiber optic cable for two-way communication—the computer transmission would appear on the subscriber's screen and he would in turn reply either through a remote control unit or telephone back over the fiber optic cable. The computer would receive his return transmission or reply and note it accordingly in its memory. Periodic and finer tuned follow-up reinforcement could occur via wired or wireless telephone based upon the patient's or employee's responses over specific time periods.

(2) coaxial cable—inasmuch as existing coaxial cable systems can transmit hundreds of times more data than a conventional telephone line, the subject computer driven system can transmit learning, motivational guidance and reinforcement to classes of subscribers over existing coaxial cable systems and the subscribers can reply using a remote unit containing computer hardware for reply back over the cable. Alternatively, the remote unit can contain a modem for reply back over wired or wireless telephone line.

(3) wireless transmission—subscribers without cable would receive the signal via antenna in the case of localized transmission or dish in the case of satellite transmission. The transmission would contain the computer driven learning, motivation and reinforcement. The subscriber would reply via wired or wireless telephone.

In each mode of transmission, subscribers can be reminded of an upcoming transmission via telephone 26 or wireless radio pager 34 as described herein. Additionally, explanatory brochures can be used with any of the above described interactions as a method of further reinforcing a patient or employee 50 toward a particular goal. With today's technology and regulatory infrastructure, programming for interactive television would remain in its current analog form and a special unit, usually a controller box plus remote positioned atop the TV set, would allow the viewer to dip into the data stream and manipulate what appears on the TV screen. With digital and compression technology (compression of up to six or more digital channels into the same bandwidth as one analog channel), a settop box would be used to decode and decompress video and audio signals in real time.

Another preferred embodiment is the use of a computer-based information metering system that uses optical discs 56 as transport and storage media, encrypting to protect data and is metered or by other payment means to permit usage by patients on a pay-per-view or pay per bit of information basis. The encryption-metering device would use digital technology and would be made available through cellular phones, wireless cable transmission, modem, interactive television and CD-ROM. Information would be distributed in encrypted form to users. After the user browses through the menu or index at no charge and selects the item needed, the encryption-metering device will decrypt the information required, record which data was used, by whom and for what issues or subjects, and will permit the user to be billed only for the data used. This information would be unreadable or unlistenable until decrypted and users would be charged based on the number of bits of information selected. A metering chip or computer board would be used to gauge data use just as an electric meter tracks power demand. Information may be retrieved in either full-text audio or image form. A decryption program keeps track of how much data is decoded and can subtract its costs from a prepaid credit stored on a chip as a form of payment. The encryption-metering technology may use a Microsoft Windows® based application or other commercially available software, with familiar graphical interfaces and menuing systems to which users are accustomed, and would be available on a variety of computer platforms.

Another preferred embodiment is the use of CD-ROM or CDI 56 (Compact Disc with Read Only Memory), a high-density storage and delivery medium similar to digital audio compact discs, which stores vast amounts of data in a digital form. Each CD-ROM 56 will hold about 600 megabytes of data, equivalent to a shelf of books almost 100 feet long, with a full text index. CD-ROMs 56 offer the fastest and most convenient way to access material from large data bases. However, most present CD-ROM systems require the user to purchase an entire data base on CD-ROMs. By contrast, the use of encryption technology and metering allows the applicant to distribute each CD-ROM for little or no cost and then charge the user only for the information actually used. The CD-ROMs 56 would be used with standard as well as portable CD-ROM players, allowing users instant access to the material virtually anywhere.

Additionally, the system of computerized telecommunications as previously described and enumerated will include the adjunct of a system for collecting expert comment, feedback and advice to greater facilitate the behavioral intervention.

Inasmuch as the relevant expert or authority figure 200 would be located some distance from the primary counselor or manager, a system has been devised for providing expert feedback at regular or periodic intervals, as follows:

A. The expert or authority figure 200 would receive summary reports of the patient's, employee's or client's 50 progress at discrete intervals. These reports would either be in the form of text, graphs, charts or verbal communications.

B. The expert or authority figure 200 would, in addition, receive recommendations of the appropriate behavioral technique, relevant goals and progress thereto, and prompts and cues in accordance with a behavioral model, such as the transtheoretical model 100, which will be more fully described below. These recommendations could additionally be in the form of prefabricated scripts which would provide greater time-saving and convenience for the health care professional or authority figure.

C. All of the above would be provided either in writing, via modem, the mail, telephone, cable network, wirelessly, CD-Rom, or other compatible means.

D. The expert or authority figure 200, upon receiving the data on each patient, employee, or client 50, would then record his advice and recommendations by means of audio tape, video tape, or download in real time his recommendations by dialing the counselor's or manager's computer for replay at a later time.

E. The counselor's or manager's computer would, through its software program, mix and blend the expert's or authority figure's 200 feedback and advice into the patient's or employee's program at appropriate intervals, all in accordance with the behavioral model or the expert's or counselor's decision.

In a system of sales, advertising, or commercial business, expert or authority messages would provide recommendations and advice at appropriate branches in the behavioral model, depending upon the employee's behavior and his stage of progress towards his sales or commercial goals.

Numerous studies have demonstrated that practitioners can use the esteem, trust and motivation provided by the physician-patient relationship to build up self-control and personal responsibility on the part of patients, resulting in heightened adherence and greater compliance with medical regimens. The subject invention facilitates the application of specific, proven behavioral strategies by extending the intervention into the patient's daily life by allowing the addition of an expert's or appropriate authority figure 200 comments to be used as an adjunct to the counselor or manager interaction. Specifically, while the counselor or manager and patient or employee proceed through their ongoing relationship process, the expert 200 or physician or other authority figure elicits a commitment from the patient, client or employee to investigate behavioral change or focus on predetermined goals. The counselor or manager in turn reinforces the commitment. The expert 200, physician, authority figure or manager receives written reports as to the patient, client or employee's progress and in turn comments upon them to the patient, client or employee in subsequent messages using the subject invention as a means of communication.

The power of an expert or authority figure 200 allows figures such as physicians or administrator's to exert social power over their patients or employees. One behavioral strategy to harness a form of this social power is to facilitate behavioral compliance with medical regimens. Research has shown that greater feelings of self-control increase behavioral commitment and play an important role in facilitating adherence. Generally, individuals may be more likely to adhere to preventive health measures if they are actively involved in making choices and in implementing their own decisions.

The subject invention facilitates individual choice, self-monitoring and self-reinforcement, all under the supervision of both expert 200, physician, or other authority figure and counselor or manager jointly, thereby increasing personal responsibility. Personal or individual responsibility has been variously cited in a medical context as the key to a policy of national health promotion and disease prevention, with the result of reduced overall medical costs. By facilitating greater compliance with medical regimens and resulting lower medical costs, the subject invention extends the state of the art accordingly.

In utilizing the subject invention, the expert 200 or physician utilizes a proven behavioral Strategy consisting of three phases. This procedure can be used effectively in conjunction with the transtheoretical model 100, described more fully below, or with other behavioral, motivational or goal setting procedures.

In the first phase, the practitioner or expert 200 attempts to build his or her motivating power. This is done by assessing the patient's 50 expectancies and responding to them with sufficient interest and concern. This phase is synchronized to the precontemplation 102 and contemplation stages 104 of the transtheoretical model 100 as will be more fully explained below.

Phase two consists of providing continuing motivation and encouragement to embark on the needed course of action. This phase is synchronized to the preparation 106 and action stages 108 of the transtheoretical model 100, described more fully below. In addition, during this phase two, the physician or expert 200 can utilize the rapport developed during phase one to prepare the patient or client 50 to realistically expect difficulties and problems that may lie ahead. This procedure is called behavioral rehearsal or stress inoculation. The principle underlying stress inoculation is that it enable individuals to cope more adequately with short-term loss before long-term gains are attained. This behavioral rehearsal is used in conjunction with providing preparatory information. Preplanning, role playing and imagery are variously used in behavioral rehearsal.

In the third phase, the expert 200 or physician provides support for the patient's preparation and anticipation of ongoing self-sufficiency. This phase is synchronized with the action and maintenance stages of the transtheoretical model. This procedure lessens potential adverse reactions to separation from treatment upon attainment of the patient's or patient's goals, by giving assurances of positive regard and arranging for gradual rather than abrupt termination of contact. By continuing to build the patient's or client's 50 sense of self-esteem and self-sufficiency during this period, a sense of personal responsibility is thus fostered. These dispositioned attributions for success thereby increase the likelihood of long-term maintenance.

In instances where relapse 112 occurs, as in the transtheoretical model 100, the expert 200 or physician may immediately intervene by allowing the patient or client 50 to attribute the relapse to normal factors outside of his control and encourage him to quickly re-enter the process by providing the recontemplation of another attempt.

During each of these phases, the physician or expert 200 may schedule additional appointments for face-to-face patient evaluation.

A singular advantage of the subject invention is that the physician or expert 200 can custom tailor reinforcement for compliance to the patient's or client's 50 response profile. Adherence drops off sharply, according to a number of studies, as the complexity of treatment regimens increases. Acute, serious illness with painful symptoms elicit the highest degrees of compliance. Chronic illness, especially those of a longer duration, elicit the lowest. In the elderly, the risk of non-compliance increases where several chronic illnesses are present requiring multiple medications at various intervals during the day. The subject invention can be uniquely adjusted to suit such situations by increasing the timing of interactive reinforcement and balancing the ratio of reinforcement prompts and cues between the counselor and physician in a manner prescribed by the physician or other expert 200.

Figure 3:
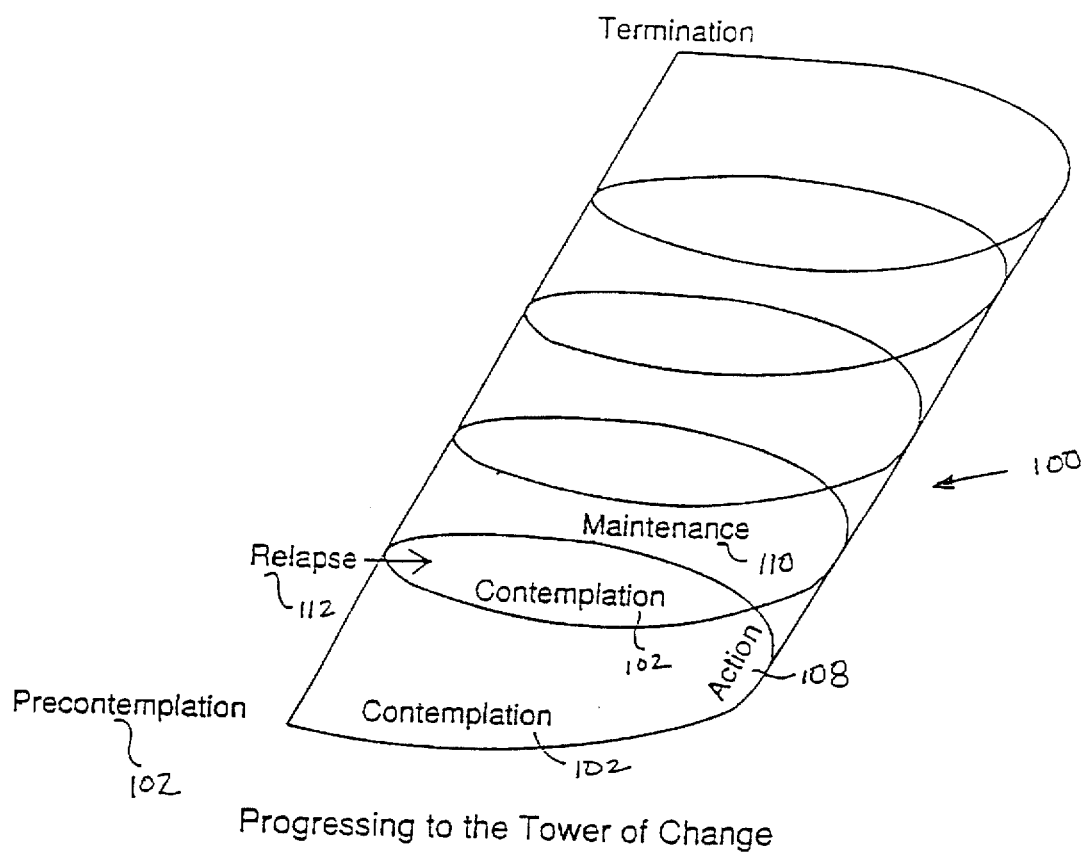
FIG. 3 is a diagram of the spiral model of the stages of change utilized by the expert in association with the client program.

As shown in FIG. 3 and as reported by Prochaska and DiClemente (1984), the preferred behavioral model embodiment is the application of the spiral or staged model of change incorporated within the patient program 14 and utilized by the expert 200 which comprises a multifaceted behavioral modification program.

Researchers James Prochaska, Carlo DiClemente and John Norcross have created a spiral model of behavioral change 100 which conceptualizes the process of behavioral change in a patient 50 in the context of a non-linear framework. Their research revealed that relapse is the rule rather than the exception among individuals with addictive behavior patterns. Therefore, by reframing relapse as a normal stage in the process, their model suggests that relapse is merely a temporary setback and that most relapsers do not regress all the way back to where they began. Instead, they use relapse as a learning experience from which to attain newer heights and move forward, in a spiral process change.

The spiral model of change 100, as shown in FIG. 3, depicts the cycle of change as consisting of six (6) distinct behavioral stages. Therefore, the patient program 14 will be directed to moving the patient 50 from one of the following six and variant stages of behavioral change 100, which are: precontemplation stage 102; contemplation stage 104; preparation stage 106 (not shown); action stage 108; maintenance stage 110; and relapse stage 112.

Prochaska, et al., have found that each of these six (6) behavioral stages is characterized by a set of specific behavior patterns. Precontemplation 102 is the behavioral stage 100 in which people are not intending to change their behavior. Many individuals or patients in this stage are unaware or underaware that they have a problem. Typically, their families, friends, neighbors or employers are well aware that there are problems. Usually the patient 50 in this behavioral stage 100 feels coerced into changing. He may feel pressured by a spouse who threatens to leave; an employer who threatens to fire him; parents who threaten to disown him; or courts who threaten to punish him. He may even demonstrate change as long as the pressure is on. Once the pressure is off, however, research has shown that he quickly returns to his old ways.

The contemplation stage 104 is the behavioral stage 100 in which one becomes aware that a problem exists. In this behavioral stage 100, the patient 50 seriously thinks about overcoming his problems. Although contemplators think about change, they have not made commitments to take action. Research has typically shown that patients in this behavioral stage 100 remain stuck in the contemplation stage 104 for long periods of time.

The preparation stage 106 is that behavioral stage 100 in which the patient 50 begins to start the modification of his behavior, which is directly followed by the action stage 108, wherein he is modifying his behavior, experiences, and/or environment in order to overcome his behavioral problem. The action stage 108 is the busiest stage and requires considerable commitment of time and energy. Behavioral changes made in the action stage 108 tend to be most visible and receive the greatest recognition from others.

The maintenance stage 110 is the time in which one works to prevent relapse and continue the gains made during the action stage 108. Traditionally, the maintenance stage 110 was viewed as a static stage. However, research has shown that the maintenance stage 110 is not an absence of change, but a continuation of behavioral change. Unfortunately, with some of the most common behavior problems, the patient 50 will not successfully maintain his gains the first time through the stages of change 100. By way of example but not of limitation, smokers who are successful self changers make an average of three to four action attempts before they become long-term maintainers. Since the relapse stage 112 is the rule rather than the exception, in solving such common problems as alcohol abuse, smoking, and weight control, the patient 50 will demonstrate a behavior along the spiral model of change 100.

In the spiral pattern, the patient 50 will process from contemplation 104 to preparation 106 (not shown), to action 108, to maintenance 110, but most individuals will go back to the relapse stage 112. During the relapse stage 112, the patient 50 will regress to an earlier stage. Some relapsers feel like failures: embarrassed, ashamed, and/or guilty. These individuals become demoralized and do not want to think about change. As a result, they return to the precontemplation stage 102.

Therefore, it is an object of the patient program 14 in this embodiment to utilize the patient's data base 12 and computer 16 to determine where the patient is on the stage model of change 100, and from there—through interactive telecommunications and in association with the expert 200—move the patient 50 from one stage to the next stage, until the maintenance stage 110 is achieved and maintained, and the targeted problem behavior is eliminated. The likelihood of successful change appears to be directly linked to an individual's position on the spiral (i.e., the particular stage within the model). Indeed, the progress made by patients as a result of professional interventions tends to be a function of the stage 100 they are in at the start of treatment.

By way of example but not of limitation, the patient program 14 and patient data base 12 will ask the patient 50 if he currently has a problem or has engaged in a desired positive behavior. If he reports an undesired status and does not intend to change in the foreseeable future such as the next six months, he will be categorized as being in the precontemplation stage 102. If the patient 50, however, intends to change within the next six months, then he is categorized as being in the contemplation stage 104. For the preparation stage 106, the patient 50 indicates that he is planning to change in the next month or have made some changes, but was not at a particular criterion. By way of example but not of limitation, an exercise program wherein the patient 50 was performing a minimum of 20 minutes three times a week would be considered in the action stage 108. Similarly, a patient 50 in the action stage 108 would have reached a particular criterion, such as quitting smoking or cocaine, within the past six months. A patient 50 in the maintenance stage 110 has reached the criterion more than six months before the patient data base 12 was instituted. The timing criteria varies, but most often is the same for all behavioral problems, wherein a 12-month criterion is typically appropriate for assessing action and intentions to be taken.

Once the behavioral stage 100 has been categorized from the patient data base 12, the stages of change 114 are utilized by the patient program 14 at the critical temporal dimension that allows the patient program 14 to move the patient 50 from one behavioral stage 100 to another. In the spiral or stage model of change 100, the identification of these stages of change 114 permit us to assess how the patient 50 is to proceed to change behaviors.

Change processes 114 are covert and overt activities that individuals use to modify problem behaviors. In the past, these independent variables were used by therapists, patients, or individuals attempting to change without therapy. Hereafter, these processes 114 will be used by the patient program 14 in order to change the patient's behavior stage 100.

As shown in Table I below, there are 14 identified processes of change 114 that have received the most theoretical and empirical support in research to date. A common set of change processes 114 has been clearly identified across such diverse problem areas as the psychological distress syndrome (a combination of anxiety, depression and lowered self-esteem) and smoking and weight control.

TABLE 1

| Processes of Change | |
|---|---|
| 116. | Consciousness raising |
| 118. | Self-reevaluation |
| 120. | Self-liberation |
| 122. | Counterconditioning |
| 124. | Stimulus control |
| 126. | Contingency management |
| 128. | Helping relationships |
| 130. | Dramatic relief |
| 132. | Environmental reevaluation |
| 134. | Social liberation |
| 136. | Self-efficacy |
| 138. | Temptations to relapse |
| 140. | Decisional pros |
| 142. | Decisional cons |

Table II shows a correlation used by the patient program 14 for the process of change 114 for a given behavioral stage 100 to demonstrate the mechanism of the aforementioned processes of change 114:

TABLE II

| Correlation Between Behavioral Stage and Selected Processes of Change | | |
|---|---|---|
| | Behavioral Stage | Process of Change |
| 1. | Contemplation | Intervention |
| | | Consciousness raising |
| | | Dramatic relief |
| 2. | Preparation | Self reevaluation |
| | | Environmental reevaluation |
| | | Helping relationships |
| 3. | Action | Self liberation |
| | | Counterconditioning |
| | | Stimulus control |
| | | Reinforcement management |
| | | Helping relationships |
| 4. | Maintenance | Counterconditioning |
| | | Stimulus control |

By integrating the processes and stages of change as outlined by Prochaska et al., to create a multifaceted and multidimensional treatment system, this system tailors particular behavioral interventions accompanied by facts of the subject invention and its embodiments to patients in a customized manner consistent with the stage they are in within each cycle and stage within the aforesaid spiral process as shown in FIG. 3. For example, during the contemplation stage 104, individuals are most open to consciousness-raising techniques and are more likely to use bibliotherapy and other feedback and reinforcement educational techniques. During the action stage 108 patients need help with behavioral processes such as counter-conditioning and stimulus control to prevent relapse. During the maintenance stage 110, there is a continued emphasis on coping skills as well as a focus on improving self-efficacy levels. In some cases, the same intervention or technique may be used across several different stages of change, but with varying degrees of intensity and/or frequency. There are numerous research studies which support the notion that matching therapy programs and processes to the patient's stage of change 100, as conceptualized by Prochaska et al., will better serve the majority of patients.

By way of example but not of limitation, an online and/or CD-ROM multimedia or video game with an ascending spiral interaction or script would be used as part of the program 14. Patients 50 would be consciously or unconsciously imprinting the spiral image in their minds each time they played the game, acting out or visualizing the process of contemplation 104, preparation 102, action 108, maintenance 110 and relapse 112, and then starting again over the same cycle, thereby providing themselves with a strong sense of dramatic victory without personal or physical danger. The lessons learned, such as problem solving, pattern recognition, quick thinking, resource management and reasoned judgment, could then be gradually adopted within the patient's life. For online users it may be envisioned that a settop box would be used to render interactive 3D graphics in real time.

By way of example but not of limitation, attached hereto as Appendix A is a typical thirty day format that may be utilized by the client program 14 in association with an expert 200 such as a physician and a counselor for development of a dialogue for use in a pain management program using the aforementioned processes of change 114 shown in Table II in association with stage model of behavioral change 100 in Table. I.

And yet another preferred embodiment provided by the subject invention is than of the application of the technique or strategy of overlearning. The subject invention permits the implementation of the concept "overlearning." Overlearning is a technique which consists of providing supplementary practice once the criterion or mastery of a behavior or task has been achieved. It has been shown routinely that overlearning facilitates long-term retention of memory and behavior. Therefore the application by the subject invention of overlearning in the form of providing supplementary trials in a more convenient and economical means further extends the prior art.

Another preferred embodiment is application of the generation effect. In the subject invention the patient, client or employee 50 is asked questions which require an answer in his or her own words thereby requiring cognitive self-organization. It has been shown that individuals who generate their own organization of verbal materials remember those material better at a later time. The subject invention provides cues in the form of questions and the client 50 or patient then presses a number on the telephone 26 or other device which activates a recording means 26 for his reply. As with other embodiments, this reply is then stored for future retrieval along with appropriate comments by the physician 200, counselor or manager to the client 50, patient or employee.

Another embodiment would be refresher practice. Thus far all previous embodiments have addressed initial training and behavior modification, relapse and completion or internalization of the desired behavior or skill. However, refresher learning, practice or rehearsal is necessary typically during periods of nonuse. The subject invention allows refresher training to be more feasible and practical than all prior methods in the art. The subject invention utilizes refresher training, practice or rehearsal through at least four techniques. One is by using or substituting covert or imagery practice as symbolic rehearsal of the already learned behavior. Another technique is the provision of an abbreviated session(s) which possess reduced fidelity which is not as high as the original session(s). A third technique to provide conceptual simulation or partial-task training instead of the original guidance conditions. Lastly, the use of brief or partial cueing in the form of reminder information which would be a test or verbal questions.

In yet still another preferred embodiment is the provision of contextual variety. Numerous studies have shown that providing a variety of experiences in varied environments or providing tasks or challenges which require judgments facilitate greater cognitive processing and resulting increased long-term transfer and retention of learned behavior. The subject invention provides the patient or client 50 with behavioral prompts, cues, questions, and quizzes of a variety of settings using a plurality or modes of reinforcement. This reinforcement can be shifted randomly or periodically from telephone receiver 26, to beeper-pager 58, to on-line computer, screen-phone, to personal digital assistant, to fax 32, etc. All of which, when used in varying combinations and configurations, increase the provision of contextual variety. Further, contextual variety is achieved by varying the content of behavioral guidance material from explicit to implicit content which requires a greater degree of inferential cognitive processing. Higher levels of inferential processing can be provided by the use of incomplete or inconsistent content which requires resolving organizational discrepancies, explanations, completing details, or extrapolations and embellishments. All of which, can be provided with the object of creating challenges utilizing the subject invention which in turn can establish greater cognitive generalization and long-term retention of behavior. All of the established forms of learning and reinforcement are uniquely provided by the subject invention.

And yet an additional embodiment is the delivery of an increased plurality of descriptive examples. Positive transfer of learning and behavior has been shown to increase with the number of examples provided during training. The provision of examples increases the chance of learning new behavior or reinforcing desired established behavior. Therefore, the subject invention, in a novel and unique manner stimulates behavioral reinforcement by the provision of an increased plurality of examples, and illustrations, which may be accompanied by relevant algorithms or rules for long-term retention.

And yet another embodiment uses the instructional strategy of providing relational explanations, prompts and cues. There is considerable evidence that qualitative explanations of new knowledge and skills help an individual develop models for making new knowledge or desired behavior fit more meaningfully into his or her existing knowledge and behavioral structures by relating the new knowledge or skill to what has been previously learned or understood. Qualitative explanations enhance retention by enabling a patient, client, or employee 50 to reach a higher level of understanding and thus guide his behavior accordingly. By prompting the patient, client or employee 50 to apply the new knowledge thus learned the subject invention, in a novel manner, thus changes the prior art. Alternatively, the subject invention can prompt the patient or client 50 to utilize mnemonics or other associative strategies to create his or her own cues for recall of the learned behavior. In each instance, the subject invention increases the practical ability of the physician, counselor or manager 200 to expand and extend the practical and feasible limits over which the new knowledge and behavior thus learned and elaborated can be reinforced and applied.

Still another embodiment would be the use of multiple or a plurality of computer monitors such as interactive Television 44, or of a subdivided display screen or screens for the preparation and distribution of behavioral reinforcement through the subject invention. The operator, physician, counselor, trainer or other party responsible for delivering reinforcement could use a separate monitor, subscreens or monitors which indicated the subject patient, employee or client's 50 status, while one or more other monitors could provide appropriate textual content or scripts for delivery. Alternatively, preferred content could be indicated by symbols, icons or figures which would serve to act as prompts to the individual operator responsible for creating and delivering reinforcement.

Another embodiment would be to alter the content of reinforcement by initially providing content which is rich in explanations, facts, and relevant information but low in enumeration of rules, demands, polling or feedback. The content would be gradually varied or shifted to provide reduced explanations by increased requests for performance and polling as to compliance. Simultaneously, as the content shifted, feedback would be increased from the physician, manager or counselor 200. This extended procedure complies with the cognitive principle of providing contextual variety to improve the long-term transfer of learning and behavior.

And still yet another embodiment is the use of double-bind quizzes or questions to crystallize positive compliance. A double-bind question focuses the employee, patient or client 50 onto preparing to take action where he has not yet complied. An example would be, "Have you taken your medication yet or do you plan to within the next hour? Answer one for yes, or two for no." The second part of the compound question referring to the patient or subject's intention directs the subject to consider the polling as a prompt, and to crystallize a positive or negative declaration through his answer. The subject invention provides a means for the extensive application of intention-provoking prompts in a novel manner unknown in the prior art.

Another embodiment is the use of the subject invention by the physician, manager or counselor 200 to establish and orchestrate both simple, complex, difficult, short term and long term goals for the patient, employee or client 50. Goals provide expectations about future reinforcement, and, as such, determine intentions and future behavior. The core of goal theory is the proposition that individual's performance will be maximized when they hold specific goals. However, goals require feedback. The subject invention provides a means for establishing, communicating, reminding, changing and rewarding behavior with respect to goals. In addition, it provides a means for providing continuing feedback with respect to an individual's progress towards goals. Goals once established are more conveniently reviewed and reinforced using the subject invention than in the prior art. As such the subject invention uniquely provides a means for the cognitive regulation of individual behavior.

Another preferred embodiment is that of the interactive quiz. In the field of education it has been found that the use of daily quizzes bolsters learning and retention of factual material. In order to increase the retention of educational material, educators have found a positive correlation between the number of tests or quizzes and retention of information. For example, compared to a single test held every month, or perhaps two or three times a semester, students were given brief daily quizzes. At first, many students objected, yet they soon came to prefer the daily quizzes to longer exams. It was found that quizzes on the prior day's reading assignment helped them maintain better reading habits and greater recall than did one-hour tests given at less frequent intervals.

A novel application of the subject invention is that of extending the prior art of physician, manager and counselor behavioral guidance into applying methods utilized in the field of education. The subject invention facilitates the application of educational principles and research by allowing the daily use of interactive quizzes selected by the computer 16 from relevant material to each patient's, employee's or client's 50 stage of progress within the aforementioned transtheoretical model 100 or other applicable behavioral model.

The reinforcement of learning derived from the educational field can now be applied through the reinforcement of daily interactive or frequent quizzes which stimulate the retention of behavioral guidance and reinforcement. The advantages of the subject invention become obvious when it is seen that the patient, employee or client 50 can receive immediate feedback on his performance by answering quizzes and receiving the appropriate correction or answer when necessary. The feedback thus received is instantaneous and occurs within his daily life, at the place of performance, in a convenient and easy-to-use manner not previously known in the prior art.

Daily quizzes facilitate absorption of the subject behavioral reinforcement on a step-by-step basis. The daily quiz strategy in the field of education made it unnecessary for students to cram a large amount of material the day before exams. Immediate feedback (such as the correct answers being read aloud as soon as the quiz papers are collected) appears to promote the interactivity necessary for rapid learning.

The frequent reinforcement thus provided assisted in comprehension and recall. Insight on more elementary aspects of the educational material gradually built understanding of more complex material, followed by, a mastery of the subject, it was found. The subject invention, thus, for the first time, provides the method for utilizing findings in the field of education and adapting them to the field of behavioral guidance, medical management, and general business of such issues as compliance, goal management and the behavioral basis of a variety of chronic diseases.

An additional preferred embodiment derived from the field of education is that of review. Behavioral research has found that the human mind consolidates memory at certain key time intervals. The initial phase of memory consolidation occurs in the first few minutes after we are exposed to a new idea or learning experience. The next phase occurs during our sleep that night. If a learning experience has on-going meaning to us, the next week or so serves as a further period of memory consolidation. In effect, in this phase, the material moves from short-term memory to long-term memory for storage. Learning which is not geared to fit the natural process of memory consolidation will be more subject to the curve of forgetting.

Therefore, the subject invention facilitates ways to systematically enhance learning and memory consolidation. Through the use of the automatic nature of computer reinforcement, the computer clock 16B is synchronized to give messages of reinforcement in the natural cycle of memory consolidation. From the field of learning we know that to absorb written material, for example, it is effective to review the material five or ten minutes after first reading it. This helps encode new material in the brain and considerably improves later recall. The second natural period for review is about 24 hours later. A two or three minute review at this juncture reinforces the consolidation which occurs during sleep and will compensate for any initial decline owing the natural curve of forgetting. The third review to assist in long-term memory consolidation should occur about one week later and should last, again, for about two to three minutes. A brief review a month later, followed by another one in six months should permanently foster the retention of the material in memory.

The subject invention can be configured through the use of the computer clock 16B to enable behavioral reinforcement of prior learning to occur in a time-synchronized pattern with the normal curve of forgetting. It thus extends the prior art of medical and behavioral reinforcement for such areas as compliance with medical regimens and behavioral reinforcement in the field of chronic disease. The use of such an automatic systems synchronized to the natural processes of memory consolidation is thus a novel extension of prior art in the field of medicine and behavior.

And, yet another preferred embodiment is that of rehearsal. Rehearsal differs in a significant way from that of review mentioned hereinabove. Review acts as a reminder by reciting and summarizing material learned in the past in order to facilitate the transference to long-term memory. Review, in effect, revitalizes long-term memory. Rehearsal, by contrast, internalizes behavioral memory by the act of doing. Once again, research in the field of education is now adaptable through the application of the computerized management and transmission of behavioral guidance.

Two domains of learning are relevant to a fuller understanding of the subject invention. They are: 1) the acquisition of facts in the process of learning; and, 2) the acquisition of skills, habits and behaviors. Generally, when we read a newspaper or self-help book, or watch television, we learn facts or are at least exposed to them. By contrast, when we practice golf or tennis, try a new cooking recipe or quit smoking, we gradually learn a new skill or develop a habit. We can develop an appreciation for certain behaviors by reading and learning facts. However, it has been found in the field of education that learning by doing is the way habits, skills and behaviors are developed and subsequently internalized into our life in a lasting way.

The process of rehearsal acts to facilitate the need to learn by doing. In school, we manage to learn and internalize information and accompanying new skills because we practice reading, arithmetic and other skills on a daily basis. Structured guidance from teachers was a crucial element in our development. The stimulating environment of the classroom itself assisted in our growth. These elements added up to a total learning experience which was facilitated by the actual rehearsal and performance in this venue. This same learning experience also occurs among athletes: regular practice among peers, with an enthusiastic coach providing consistent guidance, correction and support. Practice or rehearsal is a necessary facet of learning new behaviors. When it is accompanied by feedback as in the case of a coach, teacher, counselor, manager or physician, the experience is enriched by the interaction with mentors, authority figures and peers. The subject invention extends the prior art by introducing the ability to provide prompts and cues for each patient, employee or client 50 to engage in the act of practice and rehearsal.

In the field of education, it has been found that rehearsal is particularly meaningful when it occurs at the site at which performance is to later occur. Students who are allowed to study at the same location where an upcoming test is to be given enhance their learning, recall, and subsequent test results. The subject invention facilitates rehearsal and practice based upon behavioral prompts and cues within the lifestyle of the client 50 or patient in a more convenient manner than the prior art. The progressive insight developed by successive rehearsal is enhanced when the material gradually builds the patient's, employee's or client's 50 understanding from simple to more complex material in a progressive manner. Mastery of the subject then results from this process.

In healthcare, critical issues of life and death, survival and optimal living, are related to an individual's behavior. In this context, mastery is no longer an abstract concept. Until now, it has not been possible to supply the ongoing feedback and reinforcement necessary for individuals to achieve the resulting behavioral mastery over issues which require continued practice and rehearsal. In the subject invention the client 50 or patient is asked to engage in prescribed regimens. He receives instructions as to the possible consequences, pros and cons, of his decision. He responds to questions, messages and cues regarding how well his practice or rehearsal of the prescribed regimen is perceived. Day by day, therefore, the client 50 practices replacing old undesirable behaviors with new desirable ones. In doing so, the client 50 or patient is focused on a prescribed goal in a more convenient, frequent and effective manner than has been possible in the prior art. Through practice and rehearsal he learns to differentiate between appropriate and inappropriate behavior.

The subject invention facilitates this kind of supported learning and reinforcement on a daily basis, thereby internalizing behavior. Behavior is learned by doing and is facilitated by the process of internalization. Internalization is not simply a copying process but rather a process of cognitive reconstruction. It involves rebuilding, through rehearsal, a new set of mental operations and procedures which in turn yield a new behavioral pattern. The use of a system of computerized reinforcement which integrates both a counselor and his physician 200, a manager and his administrator, provides a greater frequency of doses of reinforcement for rehearsal and practice than the prior art and represents a novel contribution to the practice of medicine, counseling and prior management technique.

Another preferred embodiment is that of time and place shifting. A major advantage of the subject invention is that it allows the physician or expert 200 and counselor to shift the time and place that they provide guidance and reinforcement to one of their own convenience. The physician 200 or counselor can record messages at the time and place most convenient to himself and then have them later programmed for delivery at a time most convenient for the client 50.

The subject invention provides behavioral guidance to the patient or client 50 at the time and place of his convenience, thereby facilitating greater receptivity in a more familiar and relaxed environment. Great convenience makes the patient more open and receptive to the behavioral prompts and cues, quizzes, reviews and rehearsals, thereby accelerating compliance and treatment progress. It is unique in that it permits the use by individuals who would not otherwise be able to receive such care and counseling due to cost or great distance from their physician or counselor.

And still yet another preferred embodiment is the ability of the subject invention to uniquely provide scalable content which can dynamically change and expand as the patient or client 50 himself grows. Each medical or behavioral intervention can be individually tailored to the client's 50 progress. Since the computer 16 is interactive, it responds at the client's 50 pace. The flexibility of this system permits both physicians and patients to adjust the appropriate dosage on demand.

Moreover, the unique combination of computers and telecommunication devices permits the packaging a wide range of behavioral content which can be simultaneously integrated in order to provide more rigid monitoring of compliance with medical regimens. This singular feature is of importance because the prevention and management of various issues of chronic disease often require the management of interrelated issues. For instance, in the area of weight loss, nutrition, exercise, stress management, and other factors all relate to the primary issue of weight loss. A treatment plan which integrates interrelated issues and topics, strategies as is facilitated by the subject invention engages the patient or client 50 and provides a more comprehensive and engaging regimen.

And yet another preferred embodiment would consist of retrieval cues which would be embedded in the behavioral reinforcement message for later retrieval. Each behavioral message within this embodiment would be accompanied by a cued word or sentence which had some relevant association which would either be strongly connected or weakly connected to the relevant material in the message. An example might be, "It's a lovely day. It's such a good day, don't forget to remember to get some exercise." In another case, the patient or client 50 would be told, "It's a lovely day. Don't forget to take your medication." It has been found by behavioral research that cue words or sentences substantially increase recall of the target words or sentences. In order for the retrieval cue to be effective, however, it has to be initially presented at the same time as the target word or sentence. For example, "It's a lovely day," has to be presented at the same time as the target, "It's such a good day, don't forget to remember to get some exercise." or "Don't forget to take your medication." Within this preferred embodiment the subject invention utilizes the retrieval cue concept for triggering planned associations to retrieve various responses from memory of the client, patient or employee 50.

The subject invention exploits the behavioral principle that recognition is almost always easier than free or uncued recall. Presenting a relevant retrieval cue which has been associated with earlier behavior evokes the original experience and acts as a prompt for the new desired behavior. By imbedding retrieval cues within its messages, the subject invention accesses the employee's, patient's or client's 50 memory by using a fragment of an earlier experience as a key to the whole desired behavior.

And yet another embodiment is adding the association of multiple dimensions to provide multiple cues for behavioral guidance. It has been found that memory performance is excellent when instead of merely reading words or seeing objects, subjects are required to perform some activity as well. Adding an action dimension facilitates recall and prevents it from deteriorating from the effects of time or aging. Combining multiple cues in one behavioral interaction more richly encodes them in memory in terms of vision, semantics and action. Material such as counting rhymes and folk songs have stood the test of time because they combine the richness of semantic coding with the rhyming and rhythmic constraints of verse. Instead of merely reading text or listening to auditory prompts and cues, patients or clients 50 can be required to perform simultaneous activity as well. For example, they might be required to scribble with a pencil, push a lever or button, or engage in some other activity requiring manual or digital manipulation. The subject invention can uniquely be adapted to providing multiple cues in order that patients or clients 50 can engage in activities which more richly encode memory.

An additional embodiment is to integrate context-dependent memory into the scheme of behavioral reinforcement within the subject invention. Context-dependent memory operates on the effect that reinstating the environment in which an event has been experienced will bring the memory of that event flooding back. Environmental cues have been shown to help to trigger relevant memory trace. In an intervention where behavior is reinforced and occurs only within a select environmental context, replicating the desired environment will trigger the desired behavior.

Therefore, if the patient or client 50 is directed through the subject invention to reestablish the desired environment by the physician or counselor 200, it will be facilitated through the medium of the subject invention thereby extending the prior art.

Alternatively, in instances where it is not possible for the patient or client 50 to reestablish the desired environment, he can be instructed to visualize the desired environment through the use of guided imagery by the physician or counselor 200 through the subject invention for the purpose of cueing desired behavior.

Another preferred embodiment would be the use of state-dependent memory for the purpose of acting as a retrieval cue in behavioral reinforcement and guidance. State-dependent memory refers to altering the patient's or client's 50 cognitive environment or conscious awareness through the use of a drug or other internalized substance which could be accessed upon cue by the counselor or physician and ingested through the mouth or through a subcutaneous injection. The purpose of the drug or other substance would be to facilitate and altered feeling, mood or state of consciousness from the patient's or client's 50 present state for various medical and therapeutic purposes including that of association with a prior similar feeling or altered state in order to trigger recall of behavior incurred during that prior state.

The subject invention uniquely extends the prior art by allowing the expert 200 to direct the patient or client 50 to access a medicine or consciousness-influencing substance in order to initiate new or recall prior behavior. As such, it uniquely extends the prior art by initiating or retrieving a state-dependent memory which cues the correct response.

Another preferred embodiment is the use of mood congruent memory for the purpose of cueing behavioral guidance. Mood congruent cueing works on matching the content of behavioral reinforcement messages to the mood state of the patient or client 50.

The subject invention asks the client 50 to rate his present mood on a scale such as Likert scale and assign a relative numerical value to it. Based upon the relative numerical value indicated by the client 50 the subject invention matches the content of behavioral reinforcement material in a like manner. Mood-congruent memory operates on the principle that behavior learned in one mood is likely to be recalled in that same mood. Research has shown that when subjects were hypnotized and induced to adopt one or other mood in learning, then they later recalled the same material when in that identical mood.

The subject invention provides behavioral prompts and cues are positively or negatively toned to the client's 50 current mood. Often subjects in a depressed mood have difficulty retrieving pleasant memories, a phenomena that may well be part of the problem of depression. If a patient or a client 50 indicates that he or she is depressed, the recall of pleasant incidents from the past will be difficult, further lowering self-esteem and deepening the depression. Cognitive approaches to the treatment of depression as applied by the subject invention can help the patient or client 50 access less depressing memories and revalue the more positive aspects of their lives, aspects that tend to be hidden in the circle of their depressive thoughts.

Conversely, in instances where the client 50 indicates a somewhat heightened mood, the subject invention will provide additional reinforcement in order to sustain his mood and provide prompts and cues which are appropriate for his circumstance. Another variation on this method would be for the subject invention to keep record of pleasurable events and activities in which patients engage. It has been demonstrated that there is a significant relationship between daily mood changes in depressed patients and the number of pleasant activities in which they engage. Further, the more the patient participates in these activities, the less depressed he or she feels. In this regard, the subject invention would be utilized to cue the patient or client to engage in events and other pleasurable activities which had been recorded previously by the patient or client. The use of the subject invention for cueing behavioral prompts and cues in manner which is congruent with the client's 50 or patient's mood is unique and a further advancement of the art.

And yet another embodiment is the use of two distinctly different types of questions for polling and interactive quizzes. The first type consists of questions which directly access memory and are part of the output of the explicit declarative memory system. The second type of questions utilized would be those which are dependent upon more implicit non-declaratory sources of memory such as priming. Priming refers to the observation that when a word or object is seen or heard more than once, it will be seen or heard more readily on second and later occasions. Learning acquired in this manner is described as implicit because the subject is not asked about earlier presentations of material to be learned, but their influence is reflected indirectly in the speed or nature of subsequent performance. The use of implicit memory can be especially useful in areas where memory associated with behavior is utilized, as contrasted to memory for facts or events. An alternative distinction of memory refers to memory for facts or events as declarative with non-declarative memory incorporating skills and behavior. By framing questions to correspond to the declarative or non-declarative memory, they are thus organized in a manner which links their content with the type of memory to be utilized.

The second type of questions shown are inference questions which use priming, are implicit and utilize the non-declarative form of learning and memory. If such information is available, it is likely to be directly available unless it is accessed by inference by other more available information. With the second type of question, inference is the more likely source of the information and provides priming for accessing the required knowledge. With inference questions, the content addressability is utilized which feeds a fragment into memory in order to call up the rest of it.

Inference questions give rise to considerably more semantically-related answers than do direct access questions. Thus, semantic factors are more significant in the indirect retrieval of information. By utilizing semantic priming, the subject invention uniquely integrates principles of semantics, language, learning, for behavior reinforcement and guidance.

And still yet another embodiment is the provision of behavioral prompts and cues synchronized to the cyclic rhythms of the human body. It has been shown in research that subjects who learn material immediately before going to bed show better retention 24 hours later than subjects who learn in the morning and then indulge in a normal day's activities. The human body has a number of cyclic rhythms that vary through a 24-hour period. The strongest one is the sleep/wake cycle. Others include body temperature which rises during the day and drops at night, and the production of a range of hormones, all of which influence the appropriateness of the provision of behavioral prompts and cues. By synchronizing behavioral prompts and cues to cyclic physiological states, the subject invention uniquely extends the prior art in as much as learning ability varies with the time of day.

Another preferred embodiment is the varying of a presentation of behavioral prompts, cues, polling and quizzes in a manner which varies with the correctness of the patient's or client's 50 answers and related behavior. In instances where a patient's or a client's 50 behavior or answers to questions conforms with the desired behavior or answers, the interval or delay between the correctly answered question and subsequent questions would be extended. Conversely, in instances where the patient's or client's 50 behavior or answer is undesired or incorrect, or it fails in relation to predetermined goals then the material or related material will be presented after a delay which becomes increasingly shorter. Spaced presentation of material enhances memory. The sooner an item is tested, the greater the probability that it will be correctly recalled, and hence the greater the probability that its recall will be strengthened.

However, by using a flexible strategy and varying the time interval for receiving additional prompts and cues inversely to the interval where incorrect behavior and answers were received, the resulting behavior becomes better learned and internalized as the practice interval is gradually extended. The eventual aim of this procedure is to extend the patient's or client's 50 appropriate behavior to the longest interval that it can be reliably repeated. The subject invention uniquely employs this strategy and extends the prior art in the application of flexible spaced presentation of reinforcement by adjusting to the context of the individual patient's or client's 50 behavior.

And yet another embodiment consists of the use of a specialized software implemented spectrum analyzer which is utilized to distinguish ring signals, busy signals or noise to permit behavioral reinforcement based on the type of signal that is detected. Software may utilize fast fourier transform interval, cadence or other detection of pulse dialing at a recipient's telephone 26, the presence of a telephone answering machine 24, or the presence or absence of voice, aids in the operation of the subject invention and makes it both efficient and less annoying for recipients.

One of the most inefficient factors when utilizing an automatic computerized polling system is the frequent use of telephone answering machines. Furthermore, nothing is more annoying to a recipient than the recording of a polling message on a telephone answering machine. Recently, techniques have been devised for detecting telephone answering machines in conjunction with computerized telecommunications polling. The subject invention integrates this feature in a new and unique manner for behavioral reinforcement and is an extension of the prior art which consisted of applications in the fields of advertising and marketing research.

And yet another embodiment is the use of branching in the design and formulation of behavioral content. The subject system branches in distinctly different ways. First, it branches in response to the employee or client's 50 answers to polling, questions, or quizzes. Upon the patient, client or employee 50 replying to a question, the system determines the appropriate level of response and subsequent question based upon the client's or employee's 50 profile stored in the database 12. The content and the level of its material can thus be scaled to the educational level and background of the client, patient or employee 50.

Secondly, the content of behavioral reinforcement provided by the subject invention branches with respect to individual choices provided to the client 50 or patient with respect to the direction and level of interest of each participant. The client 50 or patient thus is able to choose between topics and to follow his own level of interest. Branching decisions are based on answers, with branching to another sequence based upon an erroneous answer, a non-response, a correct answer, or a menu choice by the participant. A dual-tone, multiple frequency detector is utilized to detect answers from so-called touch-tone or DTMF systems 26. Alternatively, the client or patient 50 may reply via personal computer or interactive television 44 or a two-way pager 34.

And yet another embodiment consists of the ability to encode messages and provide for multiple types of branching based upon the answers given with a minimum amount of "dead time" so that the recipient has very little opportunity to hang up or lose interest in the interaction. Messages must be appropriate, easily edited, and "natural sounding" so that a natural sounding message is transmitted with "dead time" between the initial message and any following messages being virtually eliminated. The importance of the elimination of "dead time" cannot be over-emphasized in view of the fact that a recipient given even a small amount of "dead time" may feel embarrassed about answering questions generated by a computer 16 and consequently hang up the telephone 26 or other communications device, as opposed to being encouraged to participate in the interaction. Speed of computerized response is determined among other things by the type of central processing unit utilized, configuration of software and access to databases among others.

The software 16D of the subject invention as it coordinates the various components possesses an editing capability for elimination of "dead time," thereby minimizing the annoyance to the patient or client 50 and consequent non response. The software's 16D ability to approximate or guess the patient's or client's 50 choice or answer based upon prior performance provides the opportunity for more rapid response utilizing neural network and expert system software.

An additional embodiment is a convertibility feature which permits configuring the subject invention to be in a call-in/call-out mode. The subject invention can be configured for calling out for behavioral reinforcement and guidance of select patients or clients 50 in which the client 50 is contacted through the invention in its various embodiments; or, a dial-in system is provided in which the client 50 or patient contacts the system through various modes which are described in prior embodiments. This is accomplished through the utilization of storage associated with the subject invention and a detector which detects when the subject invention is receiving an incoming telephone call.

The subject invention can be configured in a manner which it can simultaneously place out-going messages and receiving incoming messages. An important feature of the subject system is that it can cross-correlate statistics online, real time, from multiple answers, as opposed to single answer statistics thus allowing for greater flexibility in the response, compilation and analysis of patient or client 50 data.

And yet another embodiment consists of a break-off control or attention circuit which may terminate the computer interface aborting to a terminal for direct communication with an operator. One appropriate abort capability allows a call to a patient or client 50 to go to vocal communication with an operator, nurse, physician, expert, or counselor in a live mode in order to establish or reinforce rapport, check-up, customer satisfaction, discipline, congratulations, or other forms of approval or disapproval all in a personalized manner. Statistical analysis and selection can be utilized with respect to patients, employees, or clients 50 who are provided such "live" communication through the subject invention.

In various operating formats, the patients, employees or clients 50 may be variously qualified on the basis of entitlement in order to receive personalized intervention. They thus then may be prompted, either through the subject invention or through personalized interaction to provide appropriate data. Software 16D can be programmed as suggested above, or may be qualified as belonging to an entitled set of persons to accommodate specific health, sales, marketing, or management objectives. Alternatively, patients or client 50s may be selected based upon varying levels of critical need. Where necessary, verification of identity can be provided through a personal identification number (PIN) and/or credit card numbers.

Another distinct operation may involve actuation of a printer 32 to provide documents in relation to the operating format, or as for providing award certificates or coupons to isolated clients 50 or patients. The subject invention in this enhancement thus allows a subset of clients 50 or individuals to be isolated with respect to need, infirmity, disease, psychological attribute, or change in current condition. Furthermore, the subject invention in this embodiment comprises a conventional communication or telephone instrument for voice communication means in order to provide vocal operating instructions to an individual patient, employee or client 50. Allowing a person to communicate directly with said individual. Alternatively, on incoming calls after the patient or client 50 has once identified himself with his personal identification number (PIN) or credit card, the subject invention includes a cut-through circuit which enables the client 50 or patient to directly access a physician, expert 200, nurse or counselor for response to questions presented. In the alternative, on incoming calls, a member of the aforesaid group could randomly select to interact with respondents.

The subject invention thus uniquely allows an individual to verbally communicate with patients, employees or clients 50. From the respondent's viewpoint, this makes the interaction more interesting in his not knowing when he will hear from a live individual for additional guidance. Alternatively, the patient, employee or client 50 can utilize the subject invention as a "hot line" for emergency or urgently-needed reinforcement. In instances where the live expert, manager, 200 or surrogate counselor interrupted the incoming call an audible ring or other distinct sound could be provided announcing his pending arrival thus allowing physicians, nurses, experts and counselors or their surrogates to selectively interact with patient, employee, or client 50 participants in a unique and novel manner which further extends the prior art.

And yet another preferred embodiment consists of a means of awarding or crediting rewards from a predetermined deposit. In the past, an effective means in behavioral guidance has been the use of a deposit which is paid by the patient or client 50 and held by the counselor or physician 200. Cessation or abstinence based upon self-reported progress is the measure for returning a portion or all of the monetary deposit. The subject invention uniquely incorporates this technique by tabulating and statistically measuring the number of successes or failures in response to polling and quizzes. Generally, most individuals tell the truth most of the time, therefore, the patient or client 50 by risking his own money or objects of value monitors his own performance in relation to the diminution of their value based upon his self-reported behavior.

The subject invention periodically would remind the client 50 or patient of the current balance of his deposit. The diminution of value of said deposit would act as a reinforcer for correct behavior. Periodic or random feedback thus provided would serve the dual function as a measure or reminder of his behavior over a preset time interval and a continuing reinforcer as the deposit diminishes based on current or future behavior. The deposit has the affect of demonstrating the economy of the patient's or client's 50 behavior much like watching a tank of gasoline diminish in an automobile. It is expected that the client 50 or patient would seek to economize in order to slow or reduce the reduction of the aforesaid deposit.

Another embodiment consists of testing on data contained in written educational material. Often in the prescription of medication, and management and control of chronic disease numerous complex medical regimens are necessary. The written instructions provided by the physician or counselor most often provides no feedback mechanism by which it can be determined if the individual client 50 or patient understood what he or she read.

Thus, the subject invention acts as an educational testing system in which patients, clients or employees 50 at remote locations are able to use a communications or computer interface to interact with the subject invention for testing and motivational guidance education. The patient or client 50 is thus able to study the instructions or publication at his leisure. At any time that he wishes to be tested on the material or at the prompt of his physician, counselor or manager 200, he need merely telephone the subject invention to be exposed to a number of test modules. Each module will consist of a voice presentation of a question and a number of possible answers. Each answer would be related to a specific button on the telephone or computer interface device. The subject invention provides greater flexibility for the patient, client, or employee 50 in absorbing educational material in his natural environment.

The subject invention thereby tends to the convenience and time constraints of both the physician, counselor, or manager 200 and the patient, client, or employee 50 in the provision of educational material. Further, the process described herein is a more stimulating educational experience in that each individual receives an immediate answer or response to his test. These and other difficulties experienced with the prior art systems have been obviated in a novel manner by the present invention through its provision of immediate feed back and testing of the patient, client or employee 50 in his natural environment. It represents an educational system in which the client 50 or patient can participate at a time and place totally of his or her choice at a minimum cost and inconvenience.

Still another preferred embodiment will be the combining of behavioral messages which are related in real time and content to each of a plurality of derivative secondary interrogatory-containing messages with, preferably, only one of the plurality of other tracks comprising a unique selectable responsive message to a particular one of the real time related derivative secondary interrogatory messages which are chainlinked in content to a particular primary interrogatory message. Thus, the stored primary and derivative secondary interrogatory messages and the associated responsive messages are spatially related to each other along with storage medium tracks in the subject invention in real time and further related in content to one another for providing a transitional derivative response to the primary interrogatory message dependent on the track selected and the real time of selection for providing a conversational real time transitional environment. In this manner, the patient, employee or client 50 appears to verbally interact with the remotely-located storage medium in the subject invention on an individual patient, employee or client 50 basis which may vary from message to message.

And yet another preferred embodiment is the use of a debit card for establishing an account from which periodic amounts would be withdrawn based upon the lack of performance by the client 50 or patient. In the field of behavioral medicine the use of a cash deposit which is provided by the client 50 or patient has facilitated greater compliance. The object being that the deposit would be entirely or partially returned to the client 50 or patient after a predetermined period based upon his performance. In this embodiment the subject invention uses a credit card account known as a debit card where the deposit is placed into the account. The patient or client 50 could use the card to purchase other items. However, amounts would be periodically debited or withdrawn from the account through the use of the subject invention based upon the failure of the client 50 or patient to continue to engage in behavior which was in accordance with preset goals.

And yet another embodiment would be the use in the field of nursing for the creative use of patient-centered care. The subject invention would be utilized for such care-giving procedures as triggering the relaxation response, empathy, cognitive behavioral change, social support, humor, communication, and the utilization and direction of therapeutic touch. In addition, the subject invention could be utilized by nurses to reinforce and implement various medical regimens supervised or unsupervised by a physician. As such, the use of the subject invention uniquely extends the prior art by expanding nursing and caregiving outside of its prior context.

And yet another preferred embodiment consists of rewards in the form of credits which are provided for achieving prescribed or unprescribed performance goals. The use of rewards has been a proven component of operant conditioning in behavior modification for many years. In the subject invention, the patient, employee or client 50 would receive immediate rewards in the form of credits based upon his self-reported performance. These credits would be applicable to future credits, premiums or other inducements which he could receive at a later time. After the patient, employee or client 50 had completed a series of correct behaviors he would immediately receive feedback in the form of an announcement in either the voice of the counselor, manager or physician, or in a synthesized or robotic voice, announcing the amount of credits that he had received for his correct behavior. By providing immediate feedback in the form of rewards that were associated in a proximal time period with the behavior, the subject invention provides a means by which the client's, employee's or patient's 50 attention is continually refocused on his short and long-term goals. At the same time that the immediate reward in the form of a credit is announced, a total or sum of cumulative credits would be announced to the employee or client 50 in order that he might know how his progress in the form of the immediate credit relates to the total amount of credits amassed during a given cycle.

The subject invention uniquely applies principles of operant conditioning in behavior modification as follows: the use of the immediate feedback provided in the form of a credit which is announced upon the completion of a series of correct behaviors acts as a proximal reinforcer in reinforcing positive behavior. The mechanism of simultaneously announcing the total amount of credits further reinforces long-term behavior by providing a distal reinforcer which is more closely tied to a long-term or intermediate-term goal.

The subject invention uniquely applies reinforcement derived from operant conditioning by transmitting this behavioral technique through the means of remote communications in a manner which integrates the reinforcement directly into the client's 50 or patient's or employee's lifestyle as he goes about his daily life. In the prior art, symbolic rewards have been used in the forms of tokens or other reinforcers which would be symbolic of achievement towards a patient's, employee's or client's 50 goals. These rewards were used in institutions, firms, schools and in group meetings. Inasmuch as within the present invention the patient, client, or employee 50 is located some distance from the manager, physician or counselor, the use of credits is both unique and the only means of immediately providing reinforcement in a system of remote behavioral modification. A variation would be to provide coupons which would be exchangeable for tangible rewards which would be transmitted by facsimile telecommunications 32.

Once the client 50 or patient had reached prescribed goals the computer 14 would sense preset thresholds for reward and would in turn via modem transmit coupons which would be then printed by the patient's, employee's or client's 50 modem, printer or facsimile machine 32.

An additional preferred embodiment would utilize the operant conditioning and reinforcement technique known as a contingent contract. In this instance, the subject invention provides a means for allowing patients and clients 50 to set forth and monitor their own self-imposed rewards or reinforcers. In conjunction with prompts from a physician or counselor 200, the client 50 could enumerate tasks and goals which constituted desirable behavior. In conjunction therewith, the patient or client 50 upon prompts and cues from the physician or counselor 200, lists rewards or reinforcers which he would receive or provide in his daily life for his behavior.

An example would be in the field of weight loss. A client 50 could commit to not consuming more than 1500 calories a day for five days. In exchange thereof, he could select a reinforcer such as going to a motion picture upon the sixth or subsequent day which would act as a reward or reinforcer. The announcement and/or prerecorded commitment on the patient's or client's part to engage in approved behavior during a prescribed interval would be accompanied by a predetermined reward which would then be played to him upon his achievement of his own or negotiated preset goals. By announcing and recording his commitment to his goals, the client 50 or patient makes a public semi-commitment to change. The subject invention uniquely allows the client 50 to both choose his reward or reinforcer and then to immediately receive confirmation of his achievement of it once he has met prescribed goals. This self-reinforcing procedure uniquely extends the prior art and allows the client 50 himself to integrate his unique positive behavioral reinforcers into his daily lifestyle utilizing computerized telecommunications.

An additional embodiment which is a variation on the above reinforcement mechanism in the subject invention is the incorporation of negative reinforcement. In this embodiment in instances where the patient or client 50 ceased to engage in desirable behavior credits would be removed or subtracted from his total. In events where the subject client 50 or patient would cease to engage in prescribed behavior credits would be removed from his total and additional prerecorded messages from his counselor, manager or physician would be utilized for correction and/or redirection. Thus, the immediate feedback provided by the subject invention in delivering the full power of social influence which is derived from the presence of the physician, authority figure, or expert 200 accompanied by the counselor immediately provides encouraging feedback accompanied by the patient's, employee's or client's 50 perceived disapproval on the part of a significant other, in the form of his physician, counselor, administrator or other expert 200. By receiving immediate feedback in close proximity to his failure to engage in appropriate behavior, the present invention integrates a meaningful learning experience into the employee's, patient's or client's 50 life in a more rapid and convenient manner than the prior art.

And yet another embodiment would be the application of the behavioral principle of stimulus control. In this embodiment the patient, employee or client 50 would receive behavioral guidance and reinforcement delivered by the subject invention at a fixed time and fixed place on a regular or periodic schedule. A novel characteristic among others of the subject invention is that it is flexible and can deliver behavioral reinforcement and guidance at any time, 24 hours a day, and to any predetermined place which is accessible by remote communications. By selecting a predetermined time and place for behavioral reinforcement in conjunction with the client 50, the principle of stimulus control can be utilized in conjunction with the subject invention in a novel and unique manner. In all prior embodiments, it has been assumed that the reinforcement could be applied in either a random or fixed time interval. However, in this embodiment both the time and/or the place of reinforcement are predetermined and fixed. The client 50 thus associates the place of reinforcement with the message of reinforcement within that time interval. In other words, if four o'clock and a specific place or room are designated by the patient or client 50 and physician or counselor 200, then the daily or periodic nature of this prearrangement acts to amplify the reinforcement of the stimulus of the behavioral prompts and cues.

Examples of this in the prior art are having students study each day in the same room at the same time. Alternatively, psychologists have required client 50 with insomnia to use their bed for sleeping only when they felt tired and at a fixed time each day. The principle involved was in allowing the patient or client 50 to associate that particular room and desk or bed only with the purpose for which it was designated. In the case of insomnia, psychologists have not allowed patients to eat or watch television in the bed that was designated for sleeping. By thus controlling the stimulus through remote communications, the subject invention utilizes the principle of stimulus control found in the prior art in a novel and unique manner.

Once stimulus control is initially fixed and associated with a specific time and place, it can later be slowly expanded to wider time intervals and larger perimeters of space. In other words, the patient, employee, or client 50 would gradually expand the time intervals for reinforcement to a wider range and the place intervals from one room to the entire house or office.

An additional embodiment would be the use of guided imagery and visualization which was directed through the subject invention in the form of the content of the behavioral prompts and cues which complied with known successful principles of reinforcement and guidance. In this embodiment three forms of imagery or visualization would be utilized.

The first would be that of the physician or counselor 200 directing the patient, employee or client 50 to mentally visualize the appropriate or desired behavior. This could be in the form of a session in which visual prompts and cues were given utilizing standard techniques for guided imagery. The second would be observation. In this technique the client 50 or patient would be directed by the physician or counselor 200 to observe the appropriate behavior in others. He would be asked to watch others engage in behaviors which reinforced the prescribed behavior. This is an application of the well-known behavioral technique of modeling or learning by observation. A large proportion of human learning occurs through observation. By directing the patient, employee or client 50 to engage in focused observation and then polling him with the subject invention as to his participation in this behavior, learning and behavioral modification is facilitated. The subject invention extends the prior art by possessing the facility to give the patient or client 50 greater frequency of prompts and cues for engaging in the learning behavior of observation and integrating this technique into his daily life through the facility of remote communications directed by a computer.

An additional technique of behavior modification would be that of stress reduction through the use of guided imagery. Additional prompts and cues would be utilized through the subject invention to provide imagery and visualization for relaxation, stress reduction and acting out of imagery scenarios wherein the patient, employee, or client 50 overcame problem behaviors. All of the aforesaid techniques of guided imagery and visualization are possible and can be used with greater frequency utilizing the subject invention and can be integrated without limitation into all prior embodiments when appropriate.

Still another preferred embodiment would be the variation in the provision of feedback. The subject invention uniquely provides behavioral reinforcement in the form of information, prompts and cues. In addition, it possesses the ability to provide feedback in the form of comments on the results of the client's 50 or patient's performance. This feedback can be provided in the form of written reports, comments by the client's, employee's 50 or patient's physician, manager or counselor or automated response which is cued by the computer 16 based upon predetermined thresholds. This resulting feedback could be in either physician's, manager's or counselor's 200 voice or in a digitized or automated speech synthesis system. An abundance of behavioral research has shown that once a patient or client 50 has developed a rudimentary facility in the desired behavior, that varying the feedback on his performance results in improved performance. Once a client 50 or patient reaches a desired level of proficiency, the intermittent varying of the feedback on his performance generally tends to strengthen the resulting performance. In general, feedback is necessary when a new behavior is to be learned. However, there is evidence that the frequency of feedback is not critical once the new skill is integrated into the client's 50 or patient's lifestyle.

Another preferred embodiment is that of the use of systematic desensitization by means of the subject invention. The behavioral technique of systematic desensitization is based on laboratory research in classical conditioning. In instances where a patient or a client 50 possesses a fear of attempting a task or desired behavior, systematic desensitization proceeds in a gradual way so that fear and discomfort are kept to a minimum and extinction of the feared behavior is allowed to occur. The preferred procedure has three parts—the construction of a fear hierarchy, training in relaxation, and gradual presentation of items in the fear hierarchy to the patient or client 50. The fear hierarchy comprises a list of fearful situations of progressively increasing intensity. At the bottom of the list is an item that evokes only a very mild fear response in the patient or client 50, and at the top is the most highly feared situation.

After the fear hierarchy is constructed, the patient or client 50 is given training in progressive relaxation, or deep muscle relaxation. This technique is means of inducing a state of bodily calm and relaxation by having the patient or client 50 alternatively tense and relax specific groups of muscles through verbal instruction. For instance, the patient is first instructed to make a fist and to tense all the muscles of the hand as tightly as possible. After holding this tension for five or ten seconds, the patient is instructed to release the tension, and to concentrate on making the muscles of the hand as relaxed and limp as possible for 15 to 20 seconds. This procedure is used for muscles in the arm, neck, head, trunk and legs. The idea behind this procedure is that many people have a high level of muscle tension without being aware of it, and if simply told to "completely relax" a set of muscles they will be unable to do so.

However, by contrasting a high degree of muscle tension with subsequent relaxation, a person can learn to relax the muscles on cue. The progressive relaxation procedure can be cued to patients or clients 50 through the use of the subject invention in a novel manner which thereby extends the prior art. Upon completion of the relaxation technique using the subject invention as a means of transmission, the physician or counselor 200 begins with the weakest item in the hierarchy list, describing the scene to the patient, and asks the patient to imagine the scene as vividly as possible. Because the patient is in a relaxed state, and because the lowest item did not evoke a high degree of fear to begin with, it usually can be imagined with little or no fear. The patient is instructed to continue to hold the scene vividly in his imagination for a time interval determined by the physician or counselor 200. After a short pause in which the patient is told to relax, the first item is again presented. If the patient reports through the subject invention by answering an appropriate prompt that he senses no fear, then the computer 16 is signalled to repeat the procedure by slowly progressing up the list, being certain of one item is completely gone before going onto the next. Systematic desensitization has been shown to be an effective and efficient treatment for fear and performance anxiety. The subject invention provides a new and novel method in which the patient or client 50 can rehearse and eradicate fears and performance anxiety in dealing with a variety of problem behaviors which are troublesome for optimal performance.

The subject invention thus integrates systematic desensitization utilizing the aforementioned techniques of both visualization and rehearsal and combines them in a unique manner with computerized telecommunications to extend the prior art. Alternatively, the subject invention can be used for the cueing of progressive relaxation without the adjunct of systematic desensitization, or once again, in the alternative, the subject invention can be used for the systematic desensitization process utilizing rehearsal and visualization and a hierarchal list of fears which are progressively worked through in response to periodic prompts and cues given by the physician or counselor 200 and feedback provided by the client 50 or patient, all through the medium of the proposed invention.

And yet another preferred embodiment would be the use of specific scent, male or female, natural or synthesized human phenerome, for the stimulation of specific behavioral cues and related association in cueing memory of prior behavioral reinforcement. In classical conditioning it has been shown that the presentation of a conditioned stimulus such as a bell followed by food will elicit a response of salivation. Eventually, as in animals, the trials continue, the animal will begin to salivate as soon as the conditional stimulus is presented. It has been shown that human phenromes which are a family of scents which are naturally produced by the human body often produce a feeling of pleasure or satisfaction or contentment.

In the subject invention the use of natural or synthesized human pheneromes for cueing and anchoring in behavioral memory are herein described. As an adjunct to the stimulus of desired behavior, human pheneromes would be released either automatically or in conjunction with cues periodically in order to act as a reward in the development of positive behavior. Pheneromes are unique in a singular respect for their utilization in conjunction with stimulating positive behavior. Other naturally produced substances released by the body are generally produced by the brain or endocrine system and act as natural opiates such as endorphins. These naturally produced substances require the bloodstream for its use as a delivery system. In many cases they act as a natural stimulus to the nervous system and attach to specific receptor sites in the human neural network.

Pheneromes differ in that they are naturally produced by the human body through the skin and are triggered externally through the nose as a sensory organ without the necessity of passing into the bloodstream. In other words, pheneromes act as a natural stimulus which can be vaporized into the air and detected by the brain as a signal or stimulus without having to pass into the bloodstream or other internal channel.

The subject invention through the use of the computer program 16D would at appropriate intervals either remotely trigger the release of pheneromes or request the client 50 or patient to release or vaporize pheneromes in conjunction with a behavioral cue. Thus, the subject invention uniquely extends the prior art of behavioral reinforcement and conditioning by providing the stimulus of natural or synthesized pheneromes which are automatically or manually released for behavioral reinforcement and applies these substances in conjunction with a computer-mediated telecommunication system 16D utilizing wired or wireless transmission to extend the prior art. A variety of devices could be utilized to release these stimulus-providing substances such as inhalators, vaporizers, and diffusers which would be portable and could be carried on the person or would be stationary and could be placed within or adjacent to a communication device which could be located in the home, office or car of the patient or client 50.

Still yet another preferred embodiment would be use of priming to call forth either a verbal or a visual representation, to wit, a cue given verbally which would prime the verbal store in memory and a visual cue which would prime the visual store in memory. It is currently believed by many researchers that memories are stored in various forms of mental representations some of which may be visual, verbal or abstract. In order to access these memories, verbal, visual or scent based cues can be given in order to produce the desired behavioral response.

The subject invention uniquely stimulates priming of memory by calling forth the representations or cues which are necessary to trigger the desired behavior by the client 50. The computer 16 thus acts as a mediator through the medium of wired or wireless telecommunications to uniquely extend the prior art and further extend the power of the physician, manager or expert 200 or counselor to the client's, employee's 50 or patient's natural environment.

Another preferred embodiment is the use of future or past oriented imagery through the subject invention. Performance imagery is used by the physician, expert, counselor in the subject invention to rehearse acts and behavior involved in performing a task. Instructions to clients 50 or patients are given asking them to imagine a performance and to go through the steps in their minds without imagining an outcome. Either future or past oriented imagery may be utilized in conjunction with the subject invention by requesting that the client 50 or patient projects performance into the future for an upcoming task, or alternatively, recalls past performances and how they were done which is a form of review.

A further elaboration herein on the technique of review as applied through the subject invention is the review of the performance of relevant other individuals who historically confronted similar circumstances as to the client 50 or patient. In order that the client patient could view his circumstances in a new light models of historical relevance would be evoked and described as they passed successfully through similar circumstances. By recalling the patient's or client's 50 own past oriented performance and placing it in a historical context using the models of other known and unknown historical or unique figures in relevant or similar circumstances, the client, employee 50 or patient is thus enabled to gain new relevant progressive insights into his circumstance and to positively adapt accordingly in a progressive manner.

Another form of imagery would be utilized through the subject invention which is that of outcome imagery. In this instance the client 50 or patient would be requested to imagine the outcome of a task that may be positive or negative: for example, "imagine a ball rolling, rolling, right into the cup" or "rolling, rolling, toward the cup, but at the last second narrowly missing." By thus using mental practice and imagery the client, employee 50 or patient is afforded the opportunity to rehearse the sequence of movements in a given task in a symbolic manner for a learning experience. The subject invention can be thus used to cue either physical or mental rehearsal.

Another preferred embodiment is the use of the subject invention to cue the client, employee 50 or patient to engage in a variety of attentional strategies. These strategies attempt to focus the patient or client 50 on a specific object within a field. One application of this technique is in stress management. The client 50 or patient concentrates on, as in concentrative meditation, or shifts back and forth between several objects, as in integrated mediation. The subject invention would thus cue and rehearse the client 50 through imagery techniques such as guided imagery in the voice of the physician, expert or counselor 200.

Alternatively, the patient or client 50 would be directed to provide attention to a variety of internal events, including respiration, heart rate, electromyography, autonomic events, brain frequencies, finger temperature and peripheral vasoconstriction through the use of various electrical measuring and feedback devices. It has been found that these techniques are useful in the regulation of blood pressure, tension reduction, anxiety, distress, ability to relax and other physiologic functions and as a possible path to performance enhancement and concentration. The subject invention thus allows the physician, expert or counselor 200 to design regimens for administering treatments with greater frequency in the natural environment of the patient or client 50 for stress reduction and its family of related physical symptoms.

Yet another preferred embodiment would be the provision of a mechanism to provide the client 50 or patient with choice as to the mode of presentation of the behavioral reinforcement. The exercise of choice is an important cognitive principle in guiding human behavior. By providing the option of choice, self-control is fostered and self-esteem is enhanced. Inasmuch as the goal of any behavioral reinforcement scheme is the fostering of greater positive self-control by the patient, employee or client 50, the subject invention uniquely embodies the mechanism of choice. Patients, employees, or clients 50 are quizzed or polled as to their performance as previously described. In addition they are given choices as to the form of the specific intervention. For instance, as part of this embodiment a client, employee 50 or patient would be asked whether he preferred to receive reinforcement in a visual or auditory mode. By choosing a visual mode he could receive text or live or prerecorded video on either a television screen 44, computer or telephone screen or video phone 54. Alternatively, the visual text might be received on a similar hand-held or portable device 36. If the client 50, employee or patient were to choose a portable auditory or visual mode, the subject invention would allow him to receive auditory or visual behavioral reinforcement, prompts and cues through the use of a wired or wireless telephone or alphanumeric beeper device 58 respectively. Upon the client 50 electing to access an auditory or visual mode the computer would activate the appropriate storage and/or platform for the transmission of behavioral reinforcement accordingly. Alternatively, if the client, employee 50 or patient could elect to choose a form of behavioral content which would be appropriate for his particular issue. Thus the vital behavioral reinforcer of the provision of choice is fostered uniquely by the subject invention in a new and novel manner within the patient's, employee's or client's 50 natural environment. By providing choice, the client, employee 50 or patient is able to select the most personally relevant content and mode of intervention at the moment in order to derive qualitative behavioral reinforcement, explanations, and to develop models for making new knowledge fit in a more relevant and meaningful structure into what has been previously assimilated.

By providing choices within the subject invention, the long-term retention of procedural and behavioral memory are uniquely enhanced. The subject invention by providing choices within the patient's, employee's or client's 50 natural environment makes the intervention provided by the subject invention more impactful and relevant to patient, employee or client 50. The greater impact and relevance and resulting novelty increases the attention and focus of the patient, employee or client 50.

An additional preferred embodiment is that of the use of spacing of the interval of reinforcement. The subject invention uniquely possesses the ability to increase the level or retention of behavioral reinforcement by the patient, employee or client 50 by extending the spacing of reinforcement over long-term periods. One of the most reliable phenomena in human experimental psychology is the so-called spacing effect. This effect demonstrates that practice sessions or reinforcement spaced in time are superior to those of massed practice in terms of long-term retention. This effect is robust and appears to hold for verbal materials of all types and for motor skills. The subject invention allows the continuing reinforcement and spacing of review and reinforcement over extended periods within the natural environment of the client, employee 50 or patient in an economical and convenient manner. Due to the expandable nature of computer databases the subject invention allows an extremely large amount of prerecorded material to be stored so that its eventual repetition within a cycle of reinforcement is not obvious to by the patient, employee or client 50. In order to achieve maximum impact of behavioral reinforcement the content necessarily has to be fresh and novel. The use of expandable databases allow the retention of a growing library of behavioral reinforcement information, prompts and cues to be available for a novel intervention consistent with the need to provide spacing as opposed to massing of information over an extended period.

In the prior art, massed sessions were used because they generally took less total time and were more economical than spaced sessions. In the past physicians 200 or counselors were limited to the amount of material they could provide in an individual session with the client 50 or in a group. Alternatively, a book once read is seldom reviewed. A seminar once attended is infrequently revisited. The provision of spacing in the subject invention not only facilitates greater learning and compliance within the client's or patient's environment but also allows the subject client 50 or patient to proceed at his own natural pace consistent with his learning ability. The employee,1 patient or client 50 is thus more receptive and becomes accustomed to spaced reinforcement and is able to rely upon its consistent support.

And yet another preferred embodiment is that of cognitive apprenticeship. Cognitive apprenticeship fosters the direct modeling of complex cognitive tasks and borrows heavily from traditional apprenticeship which is quite successful in teaching physical skills. Traditional apprenticeship involves three components: observation, coaching and practice. Coaching physical skills involves two key features. First the coaching or feedback is given in a continuous, online fashion. For example, as an apprentice in weaving is weaving the threads, the master might guide the apprentice's hands; often the guidance is provided in the form of a physical demonstration which in itself is a form of modeling or verbal instruction. Second, the expert or master provides conceptual "scaffolding," that is the support, in the form of reminders and help, necessary for the apprentice to perform an approximation of the composite task. As the apprentice improves in his or her skill, the scaffolding can be "faded." The expert, therefore, must monitor the apprentice's zone of development or sensitivity to instruction. The zone of proximal development is the distance between the development levels at which a patient, employee or client 50 can perform a task alone and the level at which they can perform it with some assistance. Third, the apprentice practices with the master present. In this fashion, the apprentice begins by executing piecemeal aspects of the skill and yet enjoys the feedback and reward of the entire skill. The entire learning situation is imbedded in practice or guided practice. One aspect of this embodiment is that it can be used for the coaching or training of physical skills such as medical regimens necessary for the management and control of chronic disease which must be self-administered at home or in the patient's or client's 50 natural environment. Alternatively, employees 50 can be trained in the same manner in the workplace.

The subject invention is widely applicable to all physical and mental skills which have a behavioral component and have been listed herein in prior embodiments or in continuations in part. In addition, the subject invention is applicable to cognitive apprenticeship which differs from the learning or internalization of physical skills to the behavioral adoption of cognitive skills. Cognitive apprenticeship consists of six key components: modeling, coaching, scaffolding (and fading), articulation, reflection and exploration. The first three components are provided mostly by the physician, manager, expert, or counselor 200. The last three are exercised by the patient, employee or client 50.

In modeling all of the expert's 200 skills are revealed and imparted to the client, employee 50 or patient. In prior versions of the subject invention, a form of computer software 16D utilizing artificial intelligence of a knowledge base in the form of software were utilized. In this embodiment, the direct knowledge of the expert physician, manager or counselor 200 is applied in the expert's own voice. This type of behavioral instruction is superior to traditional instruction in which a client, employee 50 or patient is simply given a solution and is expected to carry out the procedure. The physician, manager, counselor or other expert 200 possesses superior knowledge in an area of importance to the patient, employee, or client 50. His influence, or referent power, is based on his identification with his expertise. The subject invention allows this expertise and associated social or referent power to be transmitted directly to the patient, employee or client 50 in his natural environment by the expert or authority figure in a convenient and unique manner which extends the prior art.

Coaching consists of observing the patient, employee or client 50 through analyzing feedback provided by reports which are generated by the computer 16 and derived from the employee or client's 50 answers to polling and quizzes. This feedback thus provided allows coaching by the physician, manager, counselor or expert 200 in the form of hints, reminders, new tasks or redirecting the client's 50 or patient's attention to an important feature—all with the goal of making the client's performance approximate the desired performance as closely as possible. Coaching provided by the physician, manager counselor or expert 200 can be in the form of prompts or cues for the patient or client 50 to ask questions, make predictions or clarify difficulties. Prompts or cues can include feedback such as remarks designed to raise the quality of the current performance. Scaffolding refers to the support the physician or counselor 200 provides so that the patient, employee or client 50 can succeed in reaching his behavioral goals. In scaffolding the client, employee 50 or patient is gradually allowed to take an increasingly larger burden for performing the task. Modeling, coaching and scaffolding all require the interactive effect provided by computerized two-way communication afforded by the subject invention.

The subject invention fosters comprehension, crystallization into memory and integration of behavior by its ability to direct the patient, employee or client 50 to make predictions about his own behavior, formulate questions about the next steps he should take, summarize his progress, and clarify difficulties in his performance. His acquisition and use of these skills through the subject invention thus improve his insights and behavior. An object of using the subject invention in cognitive apprenticeship is to encourage the client, employee 50 or patient to undertake three activities: articulation, reflection, and employee exploration. Through the use of the subject invention the client, employee 50 or patient can speak aloud for recording his summary of his progress, and predict his progress towards his goals, and ask relevant questions. The verbalizing aloud of his current cognitive state through the subject invention allows him to integrate, synthesize and link behavioral insights thus gained into memory. By reflecting on and evaluating his progress through the subject invention, he thus develops new insights, and the awareness to modify his or her own problem solving or decision making processes. Reflection involves complex processes: since it is known that confrontation by a physician, manager, administrator or counselor 200 is not necessarily an effective means of instruction. Self-perceived conflicts cognitively obtained through reflection through the use of the subject invention increase effectiveness in promoting behavioral learning. Exploration refers to the pursuing of new goals. By verbally articulating new goals through the medium of the subject invention the patient, employee or client 50 is thus able to display his own mental model to the physician, manager or counselor 200. The unique advantage in this process is that he is less self-conscious in displaying his new goals through the use of the subject invention than he would be in the physical presence of the physician, manager or counselor 200.

To some individuals it has been found that the physician, manager, expert or counselor 200 is intimidating to the client, employee 50 or patient when he is in his physical presence. Social learning theory indicates that student's mental models provide feedback to the teacher about the current level of the student's understanding. In student-teacher as in physician-patient or manager-employee relationships, it is the articulation by the less expert partner of his or her level of understanding and problems that is the critical source of learning and of construction of new knowledge. The subject invention through its ability to allow the patient, employee or client 50 to articulate his knowledge level and related problems thus promotes self-construction of behavioral skills and becomes a tool which extends the prior art in a novel manner.

Still yet another preferred embodiment is the application of the subject invention to the stimulation of behavioral learning without awareness. There is an ongoing revolution in how researchers view the storage and retrieval processes that underlie learning. We have come to realize that there are different types of storage that take place as a consequence of certain experience and that the presence of prior information may or may not influence later memory performance depending on the way in which memory is accessed. Certain types of learning appear to be data driven or stimulus driven; that is, they do not require effort, intention, or even awareness on the part of the learner, whereas other types of learning—those more familiar—are conceptually driven, that is they do require a conscious effort and intention to learn, and active interpretation of the material to be learned. Learning of the data driven type, can take place during sleep.

Traditional measures of learning do not always given the same picture of the amount of learning resulting from a given experience. In recent years, dramatic evidences emerge that certain indirect but sensitive measures of memory may yield a picture that is entirely different from that painted by the traditional measures. An event in one's life that cannot itself be recalled or recognized may nonetheless change one's perceptual thresholds, may bias one's semantic or effective interpretation of a verbal item, may reinforce earlier learning may enhance later learning.

While a person cannot remember specific events, especially seemingly inconsequential events, he or she may nonetheless have his behavior affected accordingly. Viewed from this perspective, a patient or client 50 can learn something from material presented during sleep or at a level below comprehension. The subject invention can provide subtle prompts and cues during the intervention at a subliminal level or while the client 50 is asleep. The subject invention allows the dynamic application of sleep learning procedures. Since an individual goes through cycles of the various stages of sleep as indexed by his or her pattern of EEG activity, some of which correspond to semi-wakefulness or higher arousal or both, the presentation of material can be programmed with the subject invention to occur during the natural arousal cycles.

By combining the subject invention with an EEG measuring device 46 for the recognition of peaks in cycles indicating higher arousal, the cost and sleep disruption would be minimized because the periods of arousal themselves would not be caused by the procedure. It has been found that learning that takes place in a deep stage of sleep does not transfer well to memory. However, the natural cycles of semi-wakefulness during the night share properties with states of drowsiness and semi-sleep that accompany exhaustion and sleep deprivation. At this stage, learning and creativity appear to be enhanced allowing greater receptivity to prompts and cues. The subject invention therefore facilitates greater learning by facilitating the synchronization of the timing of behavior reinforcement.

And yet a further embodiment of the subject invention is the integration of an enhanced graphical interface or hypertext into the text provided by the computer 16, television screen 44, text phone 36, lap top computer or other similar device. Hypertext is an elaborated form of text which is possible through the use of an interactive computer interface and may be available on CD-ROMS or other storage or related transmission media. Hypertext permits the provision of multiple reinforcers in the subject invention. Hypertext is a form of text which allows the patient, employee or client 50 to make choices and thus branches accordingly in its provision of content. It allows the patient, employee or client 50 to select information and proceed according to his own areas of interest and relevance to his or her self. The subject invention thus uniquely integrates the behavioral concept of choice with a text-driven medium which allows the patient, employee or client 50 to utilize choice for expanded interest and self-confidence.

Another preferred embodiment is in the treatment of acute and chronic pain. The subject invention can provide psychological support in the natural environment of the patient or client 50 following surgery or trauma in addition to utilizing support by the physician or counselor 200 to reduce anxiety and depression which accompany pain. Relaxation training is a powerful treatment for increasing pain tolerance in many situations. For example, patients of clients 50 can be instructed through the subject invention in breathing and relaxation prior to their first attempt to get out of bed after surgery. Support delivered by the physician or counselor 200 through the subject invention by reducing anxiety can increase the patient's or client's sense of control. By increasing the sense of control patients or clients 50 have been found to generally experience less pain and stress. In addition, other diversion strategies can be utilized such as: 1) imagination—inattention: pleasant imagery compatible with feeling pain, such as imagining something very positive during dental treatment; 2) imaginative transformation of pain: reinterpreting pain into a sensation like numbness, something that is part of a LAMAZE "natural childbirth" training, in which women are encouraged to substitute "pressure" for pain; 3) imaginative transfer of context: reframing the pain in some other context so as to interpret the flow of negative thinking and facilitate the generation of coping strategies; 4) external attention—diversion: focusing on external aspects of the environment such as counting ceiling tiles; 5) internal attention—diversion: focusing attention on other self-generated thoughts, such as doing complex mathematical operations; and, 6) disassociation from pain: thinking that a painful part such an arm, belongs to someone else.

The subject invention can be utilized for implementing the above or other strategies for hypnotic inductions. The subject invention can thus be utilized for stress inoculation training. It can be used to educate the patient or client 50 about the nature of pain while the client 50 experiences it in his natural environment; describing in detail the techniques available for coping with pain; and encouraging practice in and application of techniques that are relevant to the patient or client 50.

Alternatively, the physician or counselor 200 can use hypnosis for pain. The history of anesthesia is closely connected with hypnosis. Hypnosis was used widely in the middle and late 19th Century to reduce pain. The introduction of anesthetic drugs diminished the use of hypnosis. However, the subject invention uniquely allows hypnosis to be transmitted to the patient or client 50 in his natural environment without the use of anesthetics. Cognitive strategies of diversion or disassociation can be strengthened by encouraging their use under hypnosis and are facilitated in a novel manner by the subject invention. In the case of chronic or continuing pain operant conditioning can be utilized that rewards the patient or client 50 for gradually increasing general activity level and social interaction, decreasing the use of pain medication, and reducing reliance on all pain-related healthcare services. Utilizing this approach, pain is approached as a maladaptive learned behavior. Over time pain behaviors are reinforced by attention, nuturence, rest, avoidance of responsibilities and the receipt of money for disability. By using the subject invention to reverse these contingencies in the patient's or client's natural environment, it extends the prior art in a novel manner which can reduce medical costs. In addition, the subject invention may be utilized to implant and reinforce various cognitive interventions such as reducing stress with the use of covert self-statements that serve to decatastrophize pain.

Counterirritation has been utilized for many years by physicians as a method of intervention which is generally referred to as stimulation-produced analgesia. Mechanical or electrical stimulation of the peripheral nerves or neural stimulation techniques have been used to alleviate pain and increased range of motion and exercise tolerance by physicians. The subject invention can provide counterirritation in a novel and unique manner by utilizing interventions such as guided imagery, cognitive distractive techniques, and hypnotic suggestion in a manner to utilize distraction to manage both acute and chronic pain. Inasmuch as there are a wide variety of diseases and medical conditions for which treatment does not provide complete relief such as arthritis, and degenerative spinal disease, cancer and central pain conditions such as thalamic pain syndrome, the subject invention uniquely facilitates their alleviation by combining cognitive behavioral strategies with computer-driven wired and wireless telecommunications.

Another preferred embodiment is the continued measuring of mood in the subject client, employee 50 or patient. By receiving daily feedback and allowing the patient, employee or client 50 to self-rate his mood, the counselor, physician, manager or expert 200 is able to vary the intervention accordingly utilizing the subject invention. In sports, coaches attempt to prevent over training and staleness. The subject invention by providing feedback as to the mood states of the client, employee 50 or patient can allow the physician, manager or counselor 200 to anticipate periods of staleness using the self-reported psychological markers provided by the employer or patient. The physician, manager or counselor 200 is thus able to change the behavioral intervention or prescribe temporary discontinuance in order to potentiate the overall effect. The physician, manager or counselor 200 by receiving periodic or daily feedback from the client, employee 50 or patient is thus able to engage various cognitive behavioral interventions such as imagery, mental preparation strategies, progressive muscle relaxation, encouragement, autogenic training, biofeedback, hypnotherapy and cognitive restructuring coping strategies consistent with the client's mood.

And yet another embodiment of the subject invention is the monitoring of the patient's or client's 50 level of compliance in taking prescribed medicines. The subject invention by polling and providing quizzes can assess the level of self-reported consumption of medication by the patient or client 50. The computer 16 can not only thereby monitor the level of consumption but provide timely reminders to the patient or client 50 to refill his prescribed medication upon depletion. Alternatively, it can remind the physician that the prescription needs to be renewed or adjusted according to the patient's medical status. In addition, the patient's pharmacy could be alerted as to the need to refill his or her prescription based upon messages provided by the computer.

Another preferred embodiment would be the use of human interface technology to recognize the patient's, employees or client's 50 gestures for interpreting body language and speech recognition. In his practice, the physician, counselor, manager or other expert 200 often while consulting with the patient, employee or client 50 observes his gestures, body language and reaction to suggestions and instruction. The subject invention uniquely extends the prior art by obtaining feedback from the client 50 or patient in his natural environment through the use of human interface technology.

The subject invention in this embodiment combines artificial intelligence software which combines various knowledge based software systems and neural network pattern recognition. In addition, vision tracking devices and continuous speech recognition software and devices provide input to the subject invention in order to interpret and guide the client's, employee's 50 or patient's interactions with the system. The subject invention observes and determines characteristics of the patient, employee or client 50 which is in turn used to provide prompts and behavioral reinforcement and to adjust and tune the invention's computer 16 allowing it to respond to the subject patient's, employee's or client's 50 moods, performance, preferences and choices.

By applying human factors and the psychology of perception, the subject invention uniquely combines a number of desperate technologies. These technologies for input, output, entry, image management and command reduce user disorientation and combine to more closely simulate a natural interaction between the physician, counselor, administrative or expert 200 and the patient, employee or client 50. Command technologies allow the user to tell the subject invention of his choices and selections by speaking a command or reply and by directing the system through eye movements or gesturing just as pointing devices, like the mouse, have been used in the past. Semantic modeling is utilized to enable diagnostic, error recovery, and user-cueing procedures. The use of gesture recognition increases the naturalness of the interaction between the patient, employee or client 50 and the system and further facilitates convenience and ease of use in a novel manner which exceeds the prior art.

An additional preferred embodiment is the integration of multiple modes of communicating by the patient or client 50 with the subject invention. For instance, the patient, employee or client 50 could begin responding to the system over the telephone 26 and continue through his computer terminal 54 and next reply by manipulating a computer pointing device and then finish the routine by speaking a command or directing the system through eye movement or gesturing which were sensed by a video camera or other motion sensing device. The subject invention uniquely utilizes multiple modes of communicating in the provision of reinforcement and guidance. Multiple modes of communicating by the patient, employee or client 50 provide greater convenience and ease of use uniquely in his or her natural environment.

An additional embodiment will be the use of high fidelity speech and music which will be possible through transmission media which include ISDN, ATM and other broad band transmission systems. High fidelity speech will make it easier for communication between the physician, manager or counselor 200 and the patient, employee or client 50 in as much as spoken words depend as much on the nuances of expression as on the logic of the words. Another advantage that ISDN and other advanced transmission systems will make possible is speech and data that are encrypted for privacy within the subject invention.

Today there exists telephones that are secure and that are made expressly for government applications. These telephones are quite expensive and their sound is so poor that it is sometimes hard to recognize the identity of the speaker inasmuch as they first digitize the speech and then encrypt the resulting digital stream. ISDN and other broad band transmission systems use data streams which possess many times higher data transmission rates making security relatively easy to provide in addition to high fidelity of sound. The addition of music in this embodiment allows the expert or counselor 200 to provide visual imagery with greater emotional impact. The greater emotional impact provided by the use of music in the provision of information, instruction, prompts and cues for behavioral reinforcement and guidance is a novel extension of the prior art within the subject invention.

The use of the higher data rates in ISDN and other broad band transmission systems allow the facsimile of higher quality glossy printed material which may be utilized for behavioral reinforcement. A novel and distinct feature of the proposed invention is the provision of higher quality and color pictures and related printed material which can be transmitted to the patient, employee or client 50 by the physician, manager, administrator, counselor or other expert 200.

An additional embodiment of the subject invention would be the use of satellite systems which provide a transponder for communication in conjunction with the use of telecommunications. The provision of behavioral guidance could be remotely distributed in this embodiment over a wider range through the use of satellite systems and a small antenna receiver for the patient, employee or client 50. In this embodiment, the patient, employee or client 50 would attach a small antenna to his television or computer for receiving visual and audio transmissions for behavioral guidance from his physician, counselor, manager or other expert 200. He would thus be able to view his counselor, manager or physician 200 at great distance, even between continents.

Alternatively, satellite systems could be utilized for the transmission of beeper messages for behavioral motivation and guidance or said satellites could be interlinked in order to pass off signals where the patient, employee or client 50 and physician, manager or counselor 200 are separated by greater distances than can be covered by the transmission of a single satellite.

A further embodiment of the subject invention is the provision of a live counselor which would be available online, as necessary during a recorded transmission of behavioral reinforcement as previously described in all prior embodiments. While the patient, employee or client 50 was receiving a transmission he could at any time interrupt the recorded material by pushing a number on his digital touchtone phone, or using a mouse, keyboard, or similar device in conjunction with his online computer or interactive television thus intercepting the transmission and signalling his need or request for the intervention of a live counselor, company representative, nurse, surrogate physician or expert. The interception of the transmission by the surrogate would thus provide a live individual to answer questions and receive additional requests from the patient, employee or client 50 in a novel and unique manner which extends the prior art and adds an additional dimension to the interaction and regimen.

While the invention has been described in complete detail and pictorially shown in the accompanying drawings it is not to be limited to such details, since many changes and modifications may be made in the invention without departing from the spirit and scope thereof. For example, a variety of emerging telecommunication technologies provide varied platforms to transmit behavioral motivation and reinforcement. Some of these devices include: enhanced telephones containing LCD display screens for the representation of data and graphs; personal communication networks which use low power digital radio; palm-top calculators which received satellite transmissions as part of a nationwide network; wireless radio networks which exchange data on a national basis; digital cellular phones which signal their whereabouts on a continuous basis in order that their owner may be located anywhere in the world through linkage to a satellite network; and personal digital assistants (PDA) which can receive data, organize it, monitor the patient's activities, give reminders and then communicate via an internal modem as to the patient's or employee's compliance with a central mainframe computer. Also, the application of the spiral or staged model of change may be applied to all of the behavioral modification programs heretofore discussed, in addition to other areas requiring continuing behavioral reinforcement.

Still another embodiment is that of a means for initiating a behavioral contract between the patient, employee 50 and the physician, counselor, manager or trainer. The findings in counseling and behavioral research indicate that it is beneficial to encourage the patient 50 to make clear statements committing himself to a course of action. For example, in a smoking discussion, the counselor clearly states the opinion that the patient 50 ought to stop smoking and then encourages a verbal commitment from the patient 50 to a specific day and hour when he or she will stop smoking. Alternatively, a physician elicits a commitment from a patient to engage in a given number of specific exercises per week and the regular taking of medication or a manager elicits a commitment from an employee to complete a given number of tasks or goals.

This model of behavioral contracting has been used in both verbal and written forms signed by the patient in various therapies and has been tested on a variety of behaviors as reported by I. L. Janis in *Counseling on Personal Decisions, Theory, and Research on Short Term Helping Relationships*, New Haven, Yale University Press (1982) and by V. C. Li, Y. J. Kim, and C. E. Ewart et al as reported in "Effects of Physician Counseling on the Smoking Behavior of Asbestos Workers, *Preventive Medicine*, 13: 462–476 (1973). Physicians' success in eliciting this commitment was shown to be closely related to patient compliance, as reported by Bertram Stoffelmayr, et al in "Facilitating Patient Participation: The Doctor-Patient Encounter," *Primary Care*, 16:1, 269–70 (1989). Therefore, the making of direct verbal statements in the form of commitments by the patient or employee is an important form of behavior modification for compliance.

Therefore, the patient program may request that the patient or employee 50 make a verbal statement as to his proximate and distal goals based upon various prompts and cues received by the system described herein. The patient, client or employee 50 is asked to press a button on the keypad or other response device when he is about to state his goals. Upon completion of his verbal commitment, he then presses the button on the keypad again to signal that he has finished. Upon giving his first signal that he will state his commitment, his voice is recorded and stored in the device's memory. After a discrete interval, perhaps a week or more, his commitment in his own voice is played to him without prior warning following relevant prompts and cues in order to remind him forcefully in his own voice of his undertaking. The combined effect of replaying the commitment without warning after a discrete interval is one of novelty and surprise which in turn reinforces the patient, client or employee 50 of his original intention at an earlier time. By combining the instant invention and its ability to record and store verbal data, with proven behavioral findings, the state of the art is extended in a novel and unique manner.

Still another embodiment would be behavioral video conferencing. Motivational guidance and reinforcement can be provided by the use of a computer 16 connected to a telephone line by providing the patient 50 with one or more video compression boards wherein he can receive compressed video transmissions which are synchronized to sound in addition to text. The personalized transmission can be either in real time or delayed transmission. In instances where delayed transmission is utilized, it may be provided from various storage media such as CD-1, CD-ROM and video tape (VCR).

The advantage of providing video images to patients with a personal computer is that the patient, employee or client 50 can experience the presence of his health care provider, manager or counselor for greater effect and impact in behavioral guidance. In instances where the patient or client 50 receives real time transmissions, he may interact with the health care provider or manager immediately. By contrast, in instances where the patient, client or employee 50 receives recorded transmissions, he may respond and his responses can be noted by the host computer. Alternatively, the patient 50 can call a voice mailbox and ask individual questions for later response by the physician, manager or counselor.

By the addition of a video camera to the patient, client or employees 50's personal computer, the health care provider can observe him or her 50 and record his responses. Transmission can be over ATM, ISDN lines or via MODEM over analog telephone lines with appropriate signal compression. Configurations commercially available, such as INTEL, Personal Conferencing Video Systems, among others, provide the necessary components for this extension of the art.

Yet another embodiment would be the utilization of the numerous configurations of mainframe servers currently under development for interactive multimedia transmission for enabling thousands of individual customers to order video-on-demand simultaneously or home shopping. This technology configuration of a large central mainframe containing thousands of microprocessors would be particularly applicable to clinics and local or regional hospitals. Each hospital may currently serve a population in its locality of between 50,000 and 200,000 individuals. Therefore, the hospital of the future, by using the above-described interactive behavioral modification program, will place increasing emphasis on home health care.

Yet another preferred embodiment would be the use of the subject invention with an interconnected server similar to the one envisaged by Microsoft which connects a large number of "motherboards" similar to those in a PC and runs them simultaneously with custom software. Likewise, large server configurations can be adapted to small retail chains for ownership and operation at one central location, interconnecting all of its stores with its customers via cable or telephone for shopping purposes.

Alternatively and yet another configuration would be for a large hospital server as described to rent or share space with local clinics, psychotherapists and other health care providers. Prescriptions at the local pharmacy could be made part of this health delivery system wherein patient consumption of medication could be monitored and refills ordered based upon consumption profiles recorded in the data base and through polling questions administered daily. Further, local pharmacy personnel could be utilized to further explain and educate patients on the precise manner in which to administer prescribed medication. In this configuration, the subject invention would provide continuing motivation and behavioral guidance though the use of mass storage technology and various configuration of servers.

Yet another configuration would be with respect to the behavioral model, including a portion or all of the transtheoretical or Stage Process Model and all of its preferred embodiments, as to its location within the hardware and software architecture. In other words, the model could be located for administrative purposes in the server, the platform Server or both. Alternatively, a portion of the model 100 could be downloaded or located in the patient, client or employee personal computer 16, video-set top box, handheld personal communicator or screen-phone. The model 100 would be flexible in its software architecture in order to allow tuning to adapt to new or specific issues or changes, or enhancements to the model 100 or the patient, client or employee's 50 behavior.

Another preferred embodiment shall be the formulation and publication of individually customized information in the form of reports, or graphs, indicating performance and response profiles, educational monographs and tutorials and other materials necessary for providing motivation and education. By storing in the patient data base 12 a group of pre-recorded informational data of a generalized nature and accumulating personal response profiles in said patient data base 12, it is possible to mix or formulate an individual or customized printed educational document.

The specific content of said document would be adapted to each individual patient, client or employee 50 based upon his education, gender, age, demographic profile, psychological profile and prior response profiles, said educational document and text would be further formulated according to the individual's present behavioral stage 100. The patient or employee program 14 would respond to the individual response profiles, individual psychological, demographic and other historical data, and selectively draw upon generalized educational and motivational data in accordance with a behavioral algorithm containing various processes 114 for appropriate and timely insights and guidance for each individual all in accordance with the predetermined model 100. The patient or employee program 14 would thus respond to stored information signals indicative of customized recipient information for selecting certain generalized informational and educational prompts and cues of said pre-recorded signals indicative of certain segments to be retrieved selectively and in a given sequence for compilation purposes all in accordance with the predetermined model 100.

All of the aforesaid would be available as text and printed or transmitted by wired or wireless telephone, cable, the mail or delivered in person or by video. In addition, the aforesaid customized text and graphic communications could be accessed by the patient 50 via facsimile (FAX) transmission for behavioral guidance. A further variation on this embodiment would be to transmit the text via modem and telephone or cable by giving each patient, client or employee 50 a telephone number. The system would ask what information he wanted and request his fax number along with a menu of additional options. By giving his current FAX number through touch tone or voice recognition and selecting menu options by the same, the patient 50 would be able to receive a customized hard copy of his requested educational and motivational text immediately. Alternatively, the above could be sent via modem to the patient's, client's or employee's printer.

In instances where the patient, employee or client did not receive a hard copy of FAX but instead received transmission of text and data via wireless, phone or cable, a group of generalized motion picture or taped vignettes could be included for illustrating various situations or incidents of an educational nature. Said transmissions would thereby be available for recording and retention by the patient.

Another preferred embodiment would be the utilization of asynchronous transfer mode (ATM) or similar broadband protocols such as ISDM for the transmission of behavioral guidance, since all prior claims and embodiments have relied upon wired or wireless telecommunications which is transmitted or delivered on a lower grade of bandwidth. As an alternative, this embodiment relates to the asynchronous transmission of information by both wired and wireless means in private and public networks. ATM for example is equally suited for both data and real time transmissions, such as voice and video. It equally is adaptable to both local and wide-area networks.

And yet another embodiment is the mediation of positive expectancies by the subject invention. The mediation of interpersonal expectancy is an affect is an affect that has been rigorously studies in the fields of learning and enhancing human performance for decades. It is based on the observation that an authority figure 200 can alter the behavior or performance of an individual 50 by transmitting his expectations which result in altering the individual's behavior. interpersonal expectancies can be conveyed through praise, positive statements, speech rate, encouragement, praise after correct responses, giving directions, warmth, criticism, frequency of questions, frequency of interactions, and off-task behavior which references topics which do not directly relate to the task or behavior at hand.

The mediation of positive interpersonal expectancies has long been shown to increase human performance in a variety of domains such as teaching, sports, work and medicine. The interpersonal expectancy affect as it is now known has been shown in meta-analysis across a wide variety of behaviors to both favorably influence intellectual functioning and physical well being in over 400 studies. Se: Harris and Rosenthal, "Mediation of interpersonal Expectancy Affects: 31 Meta-Analyses," 1985, *Psychological Bulletin*, Vol. 97, No. 3, pgs. 363–386. Darley and Fazio, "Expectancy Confirmation Process Arising in the Social Interaction Sequence," 1980, *American Psychologist*, Vol. 35 No. 10, pgs. 867–881. Roberts, Kewman and Mercier, "The Power of Non-Specific Effects in Healing: Implications for Psychosocial and Biological Treatments," 1993, *Clinical Psychology Review*, Vol. 13, pgs. 375-391.

The subject invention by its means to enhance more frequent mediation of interpersonal expectancies on the part of the counselor, manager or physician to clients, employees and patients 50 expands the number of opportunities and places for enhancing individual performance through the mediation of interpersonal expectancies in a unique and meaningful manner unknown in the prior art.

An additional embodiment would be the use of simulations in the forms of video games and other immersive technologies such as virtual reality systems to reestablish feelings or expectancies of confidence, competence and self-efficacy through the provision of choice and goals. It has been found that where video games were provided to aging individuals during an experimental study that the experience resulted in higher quality of life scores as measured by a standardized test. It has been hypothesized that simulations such as video games have a positive affect on individuals by granting them an opportunity to exercise control over a simulated environment. Subjects who were provided semi-weekly video game exercise for 30 minutes during a period of 8 weeks showed improvement in performance of routine behavior and were more attentive, careful, and purposeful in the performance of daily tasks. In other studies, it has been shown that experience with a relatively uncomplicated routine beneficially impacted on the quality of life in aging individuals. Researchers have proposed that such experiences allow individuals to draw heightened inference or expectancy about their level of competence and control from their performance with a simulated environment. See: Monty and Perlmuter, "Choice, Control and Motivation in the Young and Aged," pgs. 99–122, *Advances in Motivation and Achievement*, 1987, Vol. 5, JAI Press, Inc., Greenwich, Conn.

Research results have shown that simple behaviors can be used to enhance the perception of control. The use of simulations such as video games, virtual reality environments and other devices can most importantly be utilized to generalize the affect from their practice to a variety of behaviors in everyday life thus providing the potential for still further increase in control and motivation.

Through the use of the subject invention, the patient, client or employee 50 can be cued or motivated to utilize simulations for enhancement of self-efficacy, control, motivation and confidence by his or her counselor, physician, manager or other authority figure 200. Simulations may be directly provided by the subject invention from stored or recorded media by the subject invention through any screen based device such as a personal computer or interactive television 44 via enhanced transmission such as ATM or ISDN or wireless transmission. The simulation or game can either be downloaded for later replay or may be transmitted in real time. The provision of simulations and games is based on the widely-accepted theoretical approach that environmental changes in response to behavior can provide feedback to individuals about their competence with respect to the environment. Changes in competence, in turn, may influence the individual's level of motivation. Increased levels of motivation may potentiate additional behaviors or increase the effectiveness of behavior, which then in turn can increase further competence and motivation. Often simulations such as video games and other immersive environments utilize a goal in addition to automatic score keeping, audio effects, randomness and the importance of speed to maintain interest and focus the player's attention. All of these qualities are transferable and may be modified or adapted to behavioral reinforcement and guidance outside of their customary use in the fields of entertainment and education. Goals, automatic score keeping, randomness, and rapid feedback are all adaptable to increasing self-efficacy, confidence and motivation under the direction of a physician, counselor, or manager 200.

Such computerized simulations have the additional advantage from a psychological point of view: error become something to learn from rather than to fear. Computerized interaction in a simulation is totally impersonal. Simulations lower the real and psychological cost of error. Often negative patterns of behavior grow out of fear of error and fear of failure. Simulations allow an individual to freely practice over and over again with a variety of permutations until an increased degree of mastery is achieved in relative privacy without human criticism.

The subject invention allows individuals to learn from their own behavior. More importantly, this feature is exploited to increase the perception of control in aging individuals and as such is a unique application. In aging individuals, the perception of control and competence are largely derived from self-appraisals thus it become important to provide the aged with a sense of intentionality, purpose, and control. This may be attained by encouraging a belief, that must be nurtured and based on experience with control. Control, goals and motivation are all intrinsically linked by the use of the subject invention in a novel manner unknown in the prior art thereby establishing or reestablishing feelings of confidence, competence and self-efficacy through the use of choice, goals and feedback.

Another embodiment would be the use of the subject invention for the provision of goal setting and visualization for stress reduction. The subject invention can be utilized for visualization and behavioral rehearsal of performance in simulated or visualized stressful situations. The subject invention can establish short and long-term goals and establish a time table for goals. Various types of software can be utilized for the process of providing feedback to clients, patients, and employee 50 in relation to their pre-established goals. Software such as ManagePro and other packages which are linked to the computer clock and calendar continuously monitor individuals in relation to the attainment of their goals. The subject invention can reduce individual stress by providing time management and goal setting, and, as such, mitigates stress-inducing personal and work-derived overload. IN addition, it provides visualization of performance which acts as a form of stress inoculation which is a technique used in pain, anger, and anxiety management. The rehearsal of feared stressful events through the use of the subject invention is a novel application and unknown in the prior art.

Yet another embodiment is the use of extrinsic or grade incentives. The subject invention through its provision of graded or rated incentives can provide rewards based upon improvement over past performance to the patient, client, or employee 50. Rewards which are based upon improvement over past performance have been found to be effective incentives for improved behavior. Studies of graded versus pass-fail courses in learning have found that substantially higher achievement results where grades are provided. IN providing graded performance, the subject invention provides reinforcement in a novel and unique manner. Alternatively, clients, employees or patients 50 may be given a form of mastery learning. Mastery learning has been shown to provide successful, motivational reinforcement for achievement. In mastery learning, individuals are given clear objectives which they must attain, such as an achievement score of 90 percent, in order to pass a test. Such individuals are allowed many attempts to pass the test but yet they are required to achieve a minimum criteria in order to do so. The subject invention by applying mastery learning thus does so in a unique and original manner.

Still, yet another embodiment is the application of the subject invention to the sequencing of temporally distributed outcomes or goals. Individuals consistently show a preference for proximal goals over distal goals. In the fields of motivation and self-regulation through behavior modification, the counselor, physician or employer 200 consistently attempts to orchestrate short and long-term goals of the individual or joint advantage of the client, patient, or employee 50. Often an individual's actions produce costs and benefits that endure over time. Often the problem of choosing between short and long-term goals creates ambivalence and becomes the central focus of an intervention. New research has shown that sequencing outcomes or goals in a manner in which values or goals increase is preferred by individuals and may be utilized for their motivation. The empirical results provided by these studies show that sequencing outcomes or goals in a manner which is consistent with individual preferences will, therefore, be useful for individual motivation. See: Lowenstein and Prelec, "Preference for Sequences of Outcomes," 1993, *Psychological Review*, Vol. 100, No. 1, pgs. 91-108.

The subject invention uniquely dispenses and monitors goals and expectancies or sequences of outcomes while it provides continuing motivational guidance and feedback. As such, it provides a unique and novel application of the prior art by integrating known findings of individual preferences for the sequencing of reinforcement.

And yet another embodiment would be the utilization of devices employing flat-panel technology for various forms of displays for motivational and behavioral reinforcement such as electronic books, facsimile terminals, office automation display, graphic and picture display. Currently, cathode ray displays, liquid crystal displays, and electroluminescent displays are utilized for the above devices. Flat-panel displays can combine many characteristics which will be adaptable to the provision of motivational guidance and behavioral reinforcement. The subject invention by utilizing flat-panel displays extends the prior art in a novel manner.

Another embodiment is the incorporation of hand-held portable electronic books. Electronic books take many forms but all have a common characteristic of being battery-powered and having a replaceable memory unit which may be in the form of a disk, cartridge or other memory unit which contains content. Electronic Books may be utilized to provide information, polling, quizzes, simulations, games and other forms of reinforcement and content which strengthens motivational guidance.

And yet another embodiment is the adoption of the Marlatt Unified Theory of Relapse to the subject invention. The Marlatt Theory developed by G. Alan Marlatt, Phd.D. provides a basis or model for avoiding, preventing or correcting behavior. In behavior modification relapse is always a possibility. The Marlatt Theory of Relapse seeks to provide the theoretical construct to reduce or prevent relapse. The integration of the Marlatt Theory of Relapse provides an important function in the subject invention of attending to the inevitable problem of relapse which occurs during behavior modification. The entire Marlatt Theory of Relapse is set forth in *Relapse Prevention*, ed. G. Alan Marlart and Judith R. Gordon, 1985, Guilford Press, New York, London.

And yet another embodiment of the subject invention would be for its use in learning, goal setting and management, and behavior modification with respect to peers or teams. As such, the subject invention can be utilized to mediate social support for individuals in their program towards goals and modification of behavior. Peer or team training and behavior modification are guided by research in socio-behavioral domains which demonstrate the positive effect of group support in behavioral modification and goal attainment. Social psychology research provides insights into the positive impact on individual productivity due to the effect of social interdependence. Behavioral psychology research adds insights on the use of rewards which may be individual or for the group or team as a whole. The subject invention allows the physician, counselor or manager to form groups or teams of individuals which share a common goal or have a common health or behavioral issue. It further allows the use or intermittent use of simulations or games for role playing exercises modeling and transfer of skills. Team or group learning can be provided by the subject invention either at a single site or at a multiplicity of sites through the use of wired or wireless communications, WAN's or LAN's and all other available means for telecommunications. The feedback thus provided and advantages thereof are: First, it personalizes the learning situation. Personal feedback in teams of groups provides a cooperative context for feedback. Trainees, patients, clients or employees process the feedback they receive from collaborators or peers differently than the feedback they receive from trainees. Secondly, peers can provide immediate and sustained remediation after an individual gives an incorrect answer or response, supportively probing, providing cues, rephrasing the query or allowing more individual attention than the physician, counselor or manager. Teams, peers or groups therefore are particularly helpful in continually monitoring members behavior, learning or performance and providing immediate interpersonal feedback and remedial help and assistance. Extensive research or peer or team leaning and performance reviewed by the National Research Council supports the use of peers or teams for goal management and behavioral reinforcement. See Druckman and Bjork, "Learning, Remembering, Believing: Enhancing Human Performance," 1994, National Academy Press: Washington, DC, Part III, Pgs. 81-170. As such the subject invention mediates peer, team, or group behavior through social behavioral principles in a manner unknown in the prior art.

There has been described and illustrated herein an improved system and apparatus for interactively changing a behavioral pattern of a patient 50. The aforesaid system uniquely extends the prior art of modifying individual behavior to the place where behavior occurs in a customized, personal manner utilizing various computer driven telecommunications platforms. While particular embodiments of the system and apparatus have been described, it is not intended that the invention be limited exactly thereto, as it is intended that the invention be as broad in scope as the art will permit. The foregoing description and drawings will suggest other embodiments and variations within the scope of the claims to those skilled in the art, all of which are intended to be included in the spirit of the invention as herein set forth.

APPENDIX A

Table of Contents

I.     Introduction . . . . . . . . . . . . . . . . . . . . . . . . i

II.    Glossary . . . . . . . . . . . . . . . . . . . . . . . . . . ii

III.   Script . . . . . . . . . . . . . . . . . . . . . . . . . . . 1

I. Introduction

This script represents the first thirty days of a prototype program indeterminate length for a hypothetical client. It is an accurate representation of the LifeStar System but the following should be noted: it is retrospective by its nature as a hypothetical model. In reality, no "script" can be written in advance for a client; it is, rather, "built" on a day-to-day ongoing basis by the counselor selecting and/or special tailoring daily modules comprised of messages of an appropriate process of change from the computer's databank of process messages. Selection is based upon client responses from the prior day, the client's position within the Spiral Model of Change, the client's entry assessment profile and program objectives.

The script, as presented, is an instructional tool for the counselor to learn how to develop a day-script vis-a-vis content and construction. The flow chart is provided as a visual representation of the day-script as "seen" by the computer; it illustrates for the counselor the script's underlying structure.

The content is a synthesis of the state of the art in management of Chronic Intractable Benign Pain Syndrome (CIBPS), a triadic approach comprised of cognitive, behavioral and stress reduction therapy strategies and tactics, as adapted to LifeStar's Interactive Medicine™ system of behavior motivation, modification, and reinforcement. Because management (versus prevention) of chronic conditions does not involve behavior change *per se* but may include modification of specific behavior(s) which might affect successful management, the Prochaska Transtheoretical Model of Behavior Change is used only as a general framework and guide rather than a paradigm for chronic disease management.

This script and its content have been approved by the National Medical Research Council's panel of advisors, many of whom are pioneers in behavioral medicine and psychology and have widely published within their fields.

II. Glossary

Stages of Change and Processes of Change

Stages:

Precontemplation: Engaged in undesired behavior with no plans to change within six months.

Contemplation: Consideration, with intent to change within six months.

Preparation: Intent to change within one month, or initiation of first steps to change.

Action: Change has been initiated.

Maintenance: Change has been ongoing for six months.

Processes:

CR: Consciousness Raising

Increasing information about oneself and problem, including observations, confrontations, interpretations, bibliotherapy. Example: "I look for information related to health and exercise." Peak Stage Effectiveness*: Precontemplation and Contemplation.

DR: Dramatic Relief

Experiencing and expressing feelings about one's problems and solutions, including psychodrama, role playing, grieving losses. Example: "Warnings about the consequences of not exercising move me emotionally." Peak Stage Effectiveness: Contemplation.

SRE: Self-Reevaluation

Assessing how one feels and thinks about oneself with respect to a problem, including value clarification, imagery, a corrective emotional experience. Example: "My physical condition embarrasses me." Peak Stage Effectiveness: Preparation.

ERE: Environmental Reevaluation

Assessing how one's problem affects physical environment, including empathy training, documentary information. Example: "I realize I can't mow the lawn; I get winded." Peak Stage Effectiveness: Preparation.

HR: Helping Relationships

Being open and trusting about the problem with someone who cares, including therapeutic alliance, social support, self-help groups. Example: "There's someone who listens and cares when I need to talk about my exercise (or lack of)." Peak Stage Effectiveness: Preparation and Action.

SL: Self-Liberation

Choice, and commitments to act; the belief in one's ability to change, including decision making therapy, self-efficacy reinforcement. Example: "I know I can become physically fit if I want to." Peak Stage Effectiveness: Action.

CC: Counter Conditioning

Substituting alternatives for problem anxiety behaviors, including relaxation, desensitization, assertion, positive self-statements. Example: "When I worry about my appearance while exercising, I say to myself, 'I look a lot better than that person over there!'" Peak Stage Effectiveness: Action and Maintenance.

SC: Stimulus Control

Avoiding stimuli that elicit problem behaviors, including adding stimuli that encourage alternative behaviors, restructuring one's environment, avoiding high-risk cues, fading techniques. Example: "I gave the Barco-Lounger to Goodwill so I won't veg-out in front of the TV after dinner, and take a walk instead." Peak Stage Effectiveness: Action and Maintenance.

RM: Reinforcement Management

Rewarding oneself or being rewarded by others for making changes, including self-reward, contingency contracts, overt and covert reinforcement. Example: "When I exercise, I feel good about myself, and my spouse comments on my improving appearance." Peak Stage Effectiveness: Action.

So.L: Social Liberation

Increasing alternatives for non-problem behaviors available in society, including empowering, policy interventions, financial incentives. Example: "I realize that people who are fit and trim appear to reap greater social and financial rewards than non-exercisers." Peak Stage Effectiveness: Precontemplation.

IC: Interpersonal Control

Avoiding people or social situations that encourage problem behavior, a variant of stimulus control, including seeking people or situations that encourage healthier behavior, restructuring social relationships. Example: "I asked my friends if we could socialize less around food, and plan more outdoor group activities. Peak Stage Effectiveness: Action and Maintenance.

BC: Behavioral Contract

A formal commitment to change, either intrapersonally, via diary or journal, or interpersonally with a trusted friend or therapeutic alliance. Peak Stage Effectiveness: Preparation and Action.

ERP: Establishing Referent Power

The first phase in Rodin and Janis' (1979) triad model for establishing and using the physician's referent power to help patients to change their behavior and be motivated to adhere to a prescribed regimen. Referent power is acquired as the physician responds to patient self-disclosure and unconditional positive regard. In Phase One (ERP), the practitioner attempts to build up motivating power; the patient is encouraged to disclose his or her personal feelings, troubles or weaknesses; a judicious level of reciprocal self-disclosure is deemed helpful in the initial stages of the physician/patient relationship.

URP: Using Referent Power

In Phase Two (URP), the physician uses his or her motivating power to encourage the patient to embark on the needed course of action and helps provide necessary resources for the patient to do so.

MRP: Maintaining Referent Power

Phase Three (MRP) demands that the practitioner retains their motivating power as an agent of change to promote further and permanent internalization of the recommended behavior changes. The physician prepares the patient to be on their own and seeks to promote feelings of self-efficacy and self-esteem.

* All processes are effective across the stages of change but are at peak effectiveness within particular stages.

Processes Specific to Pain Management

SGA: Secondary Gains Assessment:

Used to gauge an individual's reliance upon their discomfort for psychological benefit(s); a tool for both client and counselor.

CS: Coping Strategy:

Method(s) by which an individual can successfully face and deal with their discomfort.

GS: Goal Setting:

Strategy designed to cut through broad generalities ("I want to be cured") and break down treatment into smaller, realistic objectives that the client can achieve and build upon.

PAIN MANAGEMENT PROGRAM

Client:  Joseph P.
         Age 47

Referring Physician:  Dr. M. Katz

Diagnosis:  Degenerative Disc, L-4; CIBPS

Medication(s):  Ibuprofen, 600 mg; Aristocort Tab, (2) 4mg, 3 x day

Stage Evaluation:  Preparation

Goal:  Move to Action Stage - Maintenance

Hobbies:  Weight-training, gardening

Personal Metaphor:  Ice; Fire

Pets:  Dog; "Max;" Mutt

KEY TO PROCESS

| | |
|---|---|
| CR: | Consciousness Raising |
| DR: | Dramatic Relief |
| SRE: | Self-Reevaluation |
| ERE: | Environmental Reevaluation |
| HR: | Helping Relationship |
| SL: | Self-Liberation |
| CC: | Counter-Conditioning |
| SC: | Stimulus Control |
| RM: | Reinforcement Management |
| SO.L: | Social Liberation |
| IC: | Interpersonal Control |
| BC: | Behavioral Contract |
| ERP: | Establishing Referent Power |
| URP: | Using Referent Power |
| MRP: | Maintaining Referent Power |
| SGA: | Secondary Gains Assessment |
| CS: | Coping Strategy |

STRESS REDUCTION EXERCISES

| | |
|---|---|
| GS: | Goal Setting |
| PMR: | Progressive Muscle Relaxation |
| RR: | Relaxation Response |
| AD: | Active Progressive Relaxation |
| AT: | Autogenic Training |
| V: | Visualization |
| LG: | Letting Go Exercise |
| LPM: | Levine Pain Meditation |

DAY ONE

PHONE

1:0:0     (Good morning; Good afternoon; Good evening), (Name). I know you'd like to get started on your pain management program, but before we begin, I'd like to ask you a few necessary questions. OK?

1:0:1     On a scale of 0 to 5, 0 being no pain, 1 being mild, 2 being moderate, 3 being distressing, 4 being horrible, and 5 being unbearable pain, how do you rate your level of comfort at this time? Please press the appropriate number on your phone now. (Client opts 3) Thank you, (Name). (Comfort rating)

1:0:2     Now, (Name), please tell me by pressing the appropriate button what you were doing when you started to experience your pain.
        If you were active, please Press 1
        If you were sitting, please Press 2
        If you were at rest, either lying down or sleeping, please Press 3
        (Client opts 3)

Thank you, (Name).

1:03

(CR)

(SL)
    Because most other pain treatments are administered from the outside, you may not believe you can control your pain from the inside, using the power of your mind and body. But you can, and have in the past without realizing it. Music in the dentist's office, a nurse slapping your skin before giving you an injection -- these techniques are a part of a method known as distraction, one of many ways we can reduce or eliminate pain. Proof that distraction really works can be found in your own experience. Have you ever had a headache and then stubbed your toe? The headache was "forgotten" while you experienced the discomfort of your toe. You may be able to remember similar situations where you were distracted from your original source of pain by another. Please make notes as you recall these kinds of situations in your own life. Now, (Name), based upon what we've just gone over, and your own prior experience as you've recalled, do you believe that it's possible for you to learn to control your experience of pain?
        IF YES, please Press 1
        IF NO, please Press 2

1:0:4

(SL)
    IF YES:   Wonderful, (Name). Together, we'll harness your inner powers to reduce or eliminate your pain. It'll take practice and consistent application, but you can do it. We'll speak later. Thank you.

1:0:5    IF NO:    That's all right, (Name). I know it may seem a little far-fetched; after all, since childhood you've been taught to believe that someone else makes our pain go away. But you can do it. For instance, there are documented cases of people who, using self-hyponsis as their only anesthetic, have undergone major surgery without being put to sleep.

(SL)      These people were exceptional only in that they had much experience using self-hypnosis over many years. Nevertheless, the profound levels of pain prevention and relief they experienced are available to us all. You may be seeking much less dramatic results, but relief from your pain is certainly dramatic if you are suffering. You <u>can</u> learn how to manage your pain, (Name). Let's work together to unlock this power within you.

PAGER OR PHONE

1:1:0    HELLO, (NAME), THIS IS (NAME), DR. (NAME)'S NURSE. HAVE YOU TAKEN YOUR MEDICATION YET? PLEASE
         PRESS 1 FOR YES, OR
         PRESS 2, FOR NO

1:1:1    IF YES:    THAT'S GOOD, (NAME).
I'LL BE IN TOUCH LATER REGARDING YOUR MEDICATION. THANK YOU.

1:1:2    IF NO:    THAT'S OK, (NAME)
BUT PLEASE TAKE YOUR MEDICATION <u>NOW</u> WHILE WE'RE ON THE PHONE TOGETHER. IT'S VERY IMPORTANT TO TAKE YOUR MEDICINE CONSISTENTLY AT THE PROPER TIME OF DAY. I'LL WAIT A MOMENT; WHEN YOU'VE TAKEN IT, PLEASE PRESS 1 TO CONFIRM...THANK YOU.

(REPEAT 1:1:0 2X AT SIX-HOUR INTERVALS)

DAY TWO

PHONE

2:0:0

(ERP)

(Good morning), (Name). This is Dr. (Name). I'm so glad you're getting started on your pain management program. I want you to know that I understand how difficult it must be for you to cope with your suffering. It isn't easy. I know that sometimes you must feel a great sense of despair. I support your efforts. I can help. Together we can reduce your pain. Now, (Name), your attitude about your pain is important. If you believe that you can be cured of your pain, entirely rid of it, please Press 1. If you believe that your pain is something that you have to live with and learn to cope with, please Press 2.

2:0:1

IF 1:

(SRE)

That's good, (Name). Your tough, determined attitude will be a real asset to you, but there is a truth that you need to learn to accept: Some pain, such as yours, will never go away completely. It's a straightforward fact. And people who continually try to "get rid of" pain such as yours, embark on an endless odyssey of "cures," seeking someone, anyone, to stop their pain permanently. These attempts are doomed to fail, and heighten your sense of being an invalid.

2:0:2

The key to pain management is <u>acceptance</u>, acceptance of the fact of having pain that will not go away. This doesn't mean having to like it or give into it. Rather, it means realizing that nothing more can be done, medically or surgically, to eliminate the pain -- and going on from there: To have a pain program that offers a way to cope with your pain so you can live as normal a life as possible, as comfortably as possible.

2:0:3   IF 2:    That's good, (Name).
                 (ACCESS 2:0:2)

PAGER
2:1:0    (ACCESS 1:1:0; REPEAT 2X AT SIX-HOUR INTERVALS.)

PAGER
2:2:0    (ACCESS 1:0:1)

4

DAY THREE

PAGER
3:0:0     (ACCESS 1:0:1)

PAGER
3:1:0     (ACCESS 1:1:0; REPEAT 2X AT SIX-HOUR INTERVALS.)

PHONE

3:2:0     (Good morning; Good afternoon; Good evening), (Name). We all have a natural, built-in reflex to avoid or escape pain -- our bodies seem to cry out that we do something -- anything -- to get rid of it. But after you've taken reasonable steps to determine whether it is possible -- going to the doctor, getting a confirmed second opinion -- it's time to stop (CR) shopping for a miracle from an outside source, and begin to look within ourselves. Even if there's no way to eliminate your pain completely, there are safe ways of reducing it significantly, or at least "taking the edge off." You may consider your results from these techniques to be miraculous, but they all begin with a realistic acceptance of the fact of your pain -- not chasing after unreal diagnoses or impossible cures. It will be extremely helpful to you if you take a few moments to write down your answers to the following questions and explore your relationship to your pain: What philosophy, (SRE) attitude or method of living with pain works for you? What do you do when you feel pain, and how do you do it? If you're open to making these notes, a method accepted by eminent pain specialists as a valuable first step in mastery of chronic pain, please
      Press 1 for Yes, or
      Press 2 for No 3:2:1     IF YES:   Excellent, (Name)!
3:2:2                    Your answers will reveal much about you and your pain; whether you may be unconsciously allowing your pain to control your life by giving into it, (SRE) surrendering, using it as a comforting crutch to avoid living your life fully, or any other unconscious attitudes that may inhibit your efforts to gain mastery over your pain. Take your time with this list. Explore your emotions, your feelings. Are you angry? Depressed? Defeated? Or resolved to do something that will work, perhaps not as well as you'd prefer, but will work nonetheless? The list is private; no one will see (HR) it. But if you have someone in your life who you can share it with, it will be very helpful. You will need the support of someone close to assist you, be empathetic, be sympathetic. If you have someone in your life who you can share your feelings with, please
    Press 1 for Yes, or
    Press 2 for No 3:2:3    IF YES:    Wonderful, (Name). Lean on them for support during your efforts to manage your pain. Thank you, (Name).

3:2:4    IF NO:    That's OK, (Name). I'll be with you every day, every step of the way. Together, we can do it. Thank you, (Name).

3:2:5    IF NO:    That's OK, (Name). But,
    (ACCESS 3:2:2)

PAGER
3:3:0    THREE PROVEN STEPS TO MANAGING PAIN: 1. ACCEPT THE PAIN; 2. PLAN ACTIVITIES THAT DISTRACT FROM THE PAIN; 3. GET ANGRY AT YOUR PAIN IF IT SEEMS TO BE GETTING THE BEST OF YOU.

DAY FOUR

PAGER
4:0:0    (ACCESS 1:0:1)

PAGER
4:1:0    (ACCESS 1:1:0; REPEAT 2X AT SIX-HOUR INTERVALS.)

PHONE
4:2:0    (Good morning; Good afternoon; Good evening), (Name). Once you have decided to overcome your natural resistance to pain, to accept it as a part of your life and not fight it, it's important to figure out how you want to live, and what you want to do that's realistically possible for you to do. You
(GS)     must set goals. And by goals, I don't mean something impossible, like "getting rid of pain," or vague like "keeping busy." I'm referring to very specific achievements
(SRE)    or activities, for example: getting a job as a writer, working on a garden, or taking an art class. Or, how can I adapt myself to certain things I enjoy doing, but have been unable to enjoy because of my pain? For instance, if you enjoy weight-training exercise, how can you change your
(ERE)    routine, no matter how beloved, so that your pain is minimized. It might be as simple as changing your position from standing to sitting. Can you think of ways to adapt the way you perform your activities to your pain?

Now, if you're a dentist, for instance, and find that standing over your patients while they're in the chair is painful to you, you have two options. One is to retire, collect disability, and remain inactive, an invalid. If you're comfortable with that, that's fine. But you are likely to remain in pain; it may, in fact, get worse. Or, you can rethink your career. If you're that dentist, you may do some exploring and perhaps discover that you can still practice, but differently. You can teach dentistry. You can consult, you can write. Or, you may decide on another career altogether, something you can enjoy without experiencing a great deal of discomfort. If you are willing to take some time to set some specific, realistic goals for yourself, please
          Press 1 for Yes, or
          Press 2 for No 4:2:1    IF YES:   That's terrific, (Name).
4:2:2              It's very important for people in pain to set work and activity goals for several reasons: you may get additional, or primary income; you'll gain pride in accomplishment and overcoming your affliction; you'll stay busy and be less likely to get into

|         |       | poor mental and physical condition; and, significantly, you'll keep your mind off the pain so it is not noticed as much. Thank you, (Name). Speak to you later. |
|---------|-------|---|
| 4:2:3   | IF NO: | That's okay, (Name). It can sometimes be very difficult to concentrate while in pain, and look beyond it to the future. To ease your discomfort so you can think a little clearer and set goals for yourself, try this simple, effective technique: when in pain, count your breaths. Count your exhalations up to ten and begin again. If you lose count, that's okay; begin again at one. Continue the cycle: count breaths to ten, begin again at one. Concentrating on your breathing tends to stabilize the mind and quiet the anxiety that often accompanies discomfort. When you feel more comfortable, then set your goals. (ACCESS 4:2:2) |
| (CC)    |       |   |

PAGER
4:3:0   IF BEING IN PAIN MAKES YOU ANGRY, GOOD! USE YOUR ANGER AS A MOTIVATING FORCE TO LIVE THE LIFE YOU WANT TO LIVE, DESPITE THE PAIN. DIRECT YOUR ANGER AT YOUR PAIN AND THE FRUSTRATION IT CAUSES. REFUSE TO ALLOW PAIN TO DOMINATE YOUR LIFE. IF YOUR PAIN MAKES YOU MAD, PLEASE PRESS 1.

(MOVE TO ACTION)

DAY FIVE

PAGER
5:0:0 (ACCESS 1:0:1)

PAGER
5:1:0 (ACCESS 1:1:0; REPEAT 2X AT SIX-HOUR INTERVALS.)

PHONE

5:2:0

(BC)

(Good morning; Good afternoon; Good evening), (Name). I think we can both agree that we're going to work on your problem with pain together -- that we would like to see better results than you've had up until now. If you agree that is is our goal, press Press 1. If this is your intention, but you have another issue that's equally important to you, go ahead and Press 2.

(CR)

There are many ways for you to learn how to manage your pain, for example: relaxation training, physical activity, reframing and imagery, and environmental adaptation. The reason it's important for you to learn about each one of these areas is because each have been proven effective in controlling pain. Now, we're going to begin with relaxation techniques. As anyone who's ever had pain knows, stress aggravates the intensity of discomfort. If you feel open to begin controlling your pain now, using your vast inner powers to reduce it, please Press 1. If you'd rather wait until later, perhaps at bedtime, please Press 2.

5:2:1  IF 1:  That's wonderful, (Name).

5:2:2

(CR)

In 1929, physiologist Walter B. Cannon studied how the body reacts to sudden changes. He found that fear, anger, and, importantly, pain cause the body and emotions to trigger the "flight or fight" response which pumps up the body's defense mechanisms. Good for short emergencies, bad for long-term situations such as chronic pain. Your body's efforts to resist the pain after its initial onset can lead to a progressive breakdown of your immune system.

5:2:3

(APR)

(CC)

Now, I want you to use your own feelings of tension to relax. Please begin by taking a few deep, satisfying breaths, slowly inhaling and exhaling. Take a few moments to mentally examine where your tension has accumulated; perhaps it's right at the spot that causes your pain. That's OK. Try to gauge its intensity on a scale of one to ten, for example. Now, close your eyes for a few seconds. Perhaps you can imagine a speedometer reading of

|  |  | your tension. Now, I'd like you to deliberately tense those areas in your body that feel tight: your pain zone, your forehead, shoulders, jaw -- wherever. Take a deep breath while doing this. Hold each breath a few seconds along with the additional tension...now, slowly exhale and release the air and all the stress that has built up. Repeat for each area that you feel tension in, and if you don't feel your tension ease, go through this procedure again. |
|---|---|---|
| 5:2:4 | IF 2: | That's all right, (Name). We'll always move at your own pace. If you would like me to work with you later this evening, please Press 1. If you would prefer to wait until another time soon, please Press 2. |
|  |  | (If client opts 5:2:3, ACCESS 5:2:2 for later call.) |

DAY SIX

PAGER
6:0:0 (ACCESS 1:0:1)

PAGER
6:1:0 (ACCESS 1:1:0; REPEAT 2X AT SIX-HOUR INTERVALS.)

PHONE

6:2:0 (Good morning; Good afternoon; Good evening), (Name). In 1978, endocrinologist and stress research specialist, Hans Selye, used the term "distress" to describe damaging or excessive stress, the kind that you're experiencing as a
(CR) result of your pain. He found that when "distress" continues, powerful hormones are secreted that, over time, wear down the body's ability to cope. If you're open to learning another way to cope with the stress of your discomfort, please Press 1...OK.

6:2:1 Now, I want you to take several deep, satisfying breaths...Yes, that's good...At this time, as you begin to feel a little relaxed, I want you to focus your attention on a part of your body, perhaps your
(CC) pain zone, or hand; or leg; or, on a spot on the wall, on a
(IMAGERY) sound, or a color...As you focus, you might encourage your
(RR) body to relax even more...You may visualize the stress and tension and pain that has built up as constricting bands or layers that can be peeled away. Deep breathing breaks the bonds of the outer layer of stress and pain...You may be experiencing a numbness, a coldness, a warmth, or any feelings that follow in your hands, your arms, you feet, your pain zone that can further reduce your tension and discomfort. You may choose to progressively relax each muscle group in your body...Layer by layer, you can unravel the knot of distress...Your heartbeat may decrease, and with further relaxation many other changes will occur. These are positive feelings that promote good health and increase the quality of your life.

6:2:2 Now, slowly, gently, without any tension, please rate your level of discomfort. On a scale of 0 to 5, 0 being no discomfort, 5 being much discomfort, now...Thank you, (Name).

DAY SEVEN

| PAGER 7:0:0 | (ACCESS 1:0:1) |
|---|---|

| PAGER 7:1:0 | (ACCESS 1:1:0; REPEAT 2X AT SIX-HOUR INTERVALS.) |
|---|---|

PHONE

7:2:0     (Good morning; Good afternoon; Good evening), (Name). I know that sometimes you feel on edge, can't concentrate, are irritable and restless, and get tired easily as a result of your pain. That's OK; many people feel that way sometimes, and they aren't experiencing any physical pain at all -- you have every right to feel these things. If you would like to learn a way to ease these feelings and decrease you pain <u>now</u>, please <u>Press 1</u>. If you would prefer for us to work together later on, please <u>Press 2</u>.

7:2:1
7:2:2

(CC)
(VISUALIZATION)

IF 1: That's good, (Name).
Now, I want you to take several deep, satisfying breaths...Yes, that's good...deep, deep, breaths... Now, choose an activity, a place, a situation, or a person that has given you pleasure in the past, or you have fantasized about...Any thing or person that you associate with relaxation and positive feelings. Now, slowly, as you continue to breathe deeply, visualize and experience with your imagination the positive features of your choice. Explore your actions in your imagination. Perhaps remember a good time you had while engaged in this activity, visiting this place, seeing this person. Imagine the aromas, sounds, the sights...perhaps you can even recall all the nice warm, glowing feelings all over again, vividly, within your heart ...you can begin to let those feelings of contentment wash over you, gently filling you with quiet joy...Allow yourself to feel these things fully...And now, I'd like you to listen to me... listen to yourself: Anxiety will not kill me, there are lots of unpleasant things in the world, but I can stand them...I don't have to get rid of them all to feel in control. I control my emotional future...I like being non-anxious and there is no logical reason why I must be excessively anxious... I would prefer to be more relaxed, even when I feel discomfort, feel pain...I control me.
(ACCESS 6:2:2)

7:2:3    IF 2:    That's okay, (Name). We'll speak later today.
(If client opts 7:2:3, ACCESS 7:2:2 for later call)

PAGER
7:3:0    SHARE YOUR EXPERIENCES WITH OTHERS WHO HAVE PAIN. YOU ARE
(HR)     NOT ALONE. REMAIN HOPEFUL.

DAY EIGHT

PAGER
8:0:0    (ACCESS 1:0:1)

PAGER
8:1:0    (ACCESS 1:1:0; REPEAT 2X AT SIX-HOUR INTERVALS.)

PHONE

8:2:0    (Good morning; Good afternoon; Good evening), (Name). This is Dr. (Name). I've been monitoring your progress and you've made a good start. I want you to continue practicing the techniques you've learned so that you can make further
(URP)    progress toward your goal of pain reduction. Together, we can do it, (Name). Now, don't forget -- please make a note to yourself -- you have an appointment at our office on (Date). I'll see you then, and speak to you sooner. Take care.

PHONE

8:3:0    (Good morning; Good afternoon; Good evening), (Name). Sometimes, it's difficult to shut off your mind from thinking about your pain. If this is sometimes a problem for you, please Press 1...Okay, (Name), if you're open to learning how to turn off your pain thoughts now, please Press 2. If you'd prefer that we work together later on, please Press 3.

8:3:1    IF 2:    Good, (Name).
8:3:2             Now, let's begin...Begin to take several deep, satisfying breaths, really satisfying ones...Yes, just like that...Carefully experience each
(CC)              exhalation of air, four or five times, noticing the "let go" from the air escaping and your body letting go of tension, your lungs letting go of
(LG)              air, and a "let go" of thoughts for only a moment or two...As you continue to follow yourself through slow, deep breathing "let-gos," softly exhale to make a gentle humming sound from as deep in your throat as you can...really let it vibrate as slowly and as soothingly as you are able...Hum softly as you exhale for four or six slow, deep breaths... Now, let yourself watch your thoughts as they begin to come back to you, one at a time, as you might
(CC)              watch clouds drifting by on a gentle breeze...Try to have only one thought at a time; observe it, hear it, or sense it in your own way, then allow it to be replaced by another thought... You may sense the thoughts as clouds, or as birds, or as leaves floating on a stream, or a person walking by, or any image you are comfortable with...Now, (Name), (CC)   distance yourself from your thoughts...Drift with your ideas, thoughts, concerns...one at a time. Let go of each one along with a slow exhaled breath ...imagine each exhaled breath gently blowing the thought away from you, into the distance...Perhaps hum it along in your own unique way. Now...notice any emotional feeling you may be experiencing, no matter what it may be...it's OK...because you're aware of it...Experience it as fully as you can... Yes, that's right...Now, allow the feeling to move out of you just as you let go of your thoughts and let them float away. Accept the feelings as you accept the one-by-one thoughts...observe them approach, experience them as they pass over you, and then watch or sense them depart from you.

(SL)   Imagine how you can do this as often as you wish... Perhaps you will want to practice this technique several times a day, maybe once an hour for just a few minutes. With practice, you'll be able to convert your stressful thoughts into a state of deep relaxation and ease using your breathing as a cue, and your thoughts as individual markers of breathing and counting and focus. (ACCESS 6:2:2)

8:3:3   IF 3:   (ACCESS 7:2:3)
                (If client opts 8:3:3, ACCESS 8:3:2 for later call)

DAY NINE

PAGER
9:0:0     (ACCESS 1:0:1)

PAGER
9:1:0     (ACCESS 1:1:0; REPEAT 2X AT SIX-HOUR INTERVALS.)

PHONE

9:2:0     (Good morning; Good afternoon; Good evening), (Name). One common technique for relieving tension is called "autogenic training," a method that originated in Germany and is quite
(CR)     effective. Would you like to learn it? It's simple, and consists of repeating certain phrases to yourself as you focus on relaxing various parts of your body. If you would like to practice autogenic training right <u>now</u>, please <u>Press 1</u>. If you would prefer to wait until later on, perhaps after dinner, please <u>Press 2</u>.

9:2:1     IF 1:     Wonderful, (Name).
9:2:2                Now, let's begin as we generally do...get comfortable...take four or five slow, deep satisfying breaths...that's right...Yes...Now, beginning with your feet, say to yourself, "My feet are heavy and warm, very heavy and warm." Repeat this phrase several times as you focus your attention on your feet until you can actually <u>feel</u> them becoming heavy and warm...Yes, that's right... While you say this, imagine your feet in a tub of
(CC)                warm water, or near a fireplace...they are getting warmer and heavier...warmer and heavier...Now,
(AT)                gently, shift your focus to your legs, and repeat: "My legs are heavy and warm, very heavy and warm. Continue...gently move up your body, until you reach your scalp. By repeating this phrase to yourself and visualizing your body becoming heavy and warm in this way, you are promoting greater blood flow to the muscles and muscle relaxation... Feel the blood course through your body and with it comes warmth, gentle, comforting, relaxing warmth ...Yes, warmth and relaxation. (ACCESS 6:2:2).

9:2:3     IF 2:     (ACCESS 7:2:3)
                    (If client opts 9:2:3, ACCESS 9:2:2 for later call)

PAGER
9:3:0     PRACTICE YOUR RELAXATION TECHNIQUES REGULARLY. KEEP BUSY. DON'T ALLOW PAIN TO DETERMINE YOUR PLANS.

DAY TEN

PAGER
10:0:0    (ACCESS 1:0:1)

PAGER
10:1:0    (ACCESS 1:1:0; REPEAT 2X AT SIX-HOUR INTERVALS.)

PHONE

10:2:0    (Good morning; Good afternoon; Good evening), (Name). This is Dr. (Name). I just wanted to touch base with you to let you know how proud I am of you. On many of the days when you
(JRP)     were asked to rate your discomfort <u>after</u> your session, you reported your discomfort to be <u>less</u> than the number you had reported <u>prior</u> to your session. That's wonderful, (Name). Keep it up! You can do it, and I'll support you all the way.

PHONE

10:3:0    (Good morning; Good afternoon; Good evening), (Name). Sometimes when your pain has got your muscles really tense and knotted, it's helpful to work directly on them. If you're open to doing so <u>right now</u>, and getting rid of all that tightness you feel, please <u>Press 1</u>. If you'd prefer that we work together later on today, please <u>Press 2</u>.

10:3:1    IF NO:   That's terrific, (Name).
10:3:2             Let's begin now with four or six slow, deep breaths
                   ...deeply satisfying breaths...Yes...Now, beginning
                   with your feet, curl your toes and tighten them as
                   much as you can, feeling all the muscles in your
                   feet tense, allow yourself to feel this tension and
                   hold it for about ten seconds, then relax your feet
                   completely...Yes, relax them...notice how your toes
                   uncurl and the muscles feel tired and heavy...focus
                   on the differences you notice when your muscles are
(PMR)              tense and when they are relaxed...Yes, relaxed, so
                   relaxed...Now, tighten the muscles in your legs so
                   that they are as stiff and rigid as possible...hold
                   all the tension in your legs, tight as possible for
                   ten seconds...feel that tension...then...relax your
                   legs, let them go limp, focus on the sense of
                   relief you feel in them now that they are relaxed.
                   Now, move through each muscle group in your body,
                   alternating tensing and relaxing your buttocks...
                   abdomen...your back...your neck...now your jaw...
                   your arms...hands...face...Now, (Name), when you
                   have tensed and relaxed each set of muscles in your
                   body, remain still...mentally check your muscles,
                   allow yourself to experience how very heavy and
                   relaxed they feel...Notice that sense of deep, deep

|  |  |  |
|---|---|---|
|  |  | relaxation throughout your body.  This technique is called Progressive Muscle Relaxation, and you can use this method any time you need relief from the tension of your discomfort.  (ACCESS 6:2:2). |
| 10:3:3 | IF 2: | (ACCESS 7:2:3)<br>(If client opts 10:3:3, ACCESS 10:3:2 for later call) |
| PAGER<br>10:4:0 |  | TAKE FIVE DEEP BREATHS.  IMAGINE AN ICE CUBE IS IN YOUR PAIN ZONE.  YOUR PAIN IS THE PAIN OF FRIGID COLD.  VISUALIZE THE ICE CUBE SLOWLY, SLOWLY MELTING...AND AS IT MELTS AWAY, SLOWLY, SLOWLY, YOU FEEL LESS DISCOMFORT...LESS...AND LESS... UNTIL THE ICE CUBE HAS COMPLETELY MELTED AWAY, AND ALL YOU CAN FEEL IS A NUMB SENSATION WHERE THE ICE CUBE WAS. |

DAY ELEVEN

<u>PAGER</u>
11:0:0 (ACCESS 1:0:1)

<u>PAGER</u>
11:1:0 (ACCESS 1:1:0; REPEAT 2X AT SIX-HOUR INTERVALS.)

<u>PHONE</u>

11:2:0 (Good morning; Good afternoon; Good evening), (Name). It's been seven months since your injury, and I'm wondering if you've begun to consider getting some form of exercise into your daily routine so that your discomfort won't get worse. If staying in the best possible physical condition you can to minimize your discomfort is important to you, please
  <u>Press 1</u> for yes, or
  <u>Press 2</u> for no.

11:2:1 IF YES: That's good, (Name).
11:2:2         Light to moderate exercise is an excellent way to prevent your discomfort from worsening. Beginning slowly and simply, you can gradually increase your range of motion, and the strength of the muscles that surround your back injury and support your
(CR)           spine. If you remain sedentary for too long, the weakness and stiffness in your back will slowly, steadily get worse, and your discomfort and suffering will remain strong. If you'd like to find out more about exercise and its proven effectiveness toward pain relief, please
  <u>Press 1</u> for yes, or
  <u>Press 2</u> for no.

11:2:3: IF YES: Wonderful, (Name).
11:2:4:          I'm going to send you important written materials about this subject you will find instructive and informative. And afterward, if you decide to ease into a light exercise routine to help smooth the roughness of your discomfort, we'll work together, along with Dr. (Name), to see you through. Thank you, (Name).

11:2:5  IF NO:  I understand, (Name), but...
11:2:6          (ACCESS 11:2:4)

11:2:7 IF NO: That's OK, (Name). But did you know that...
11:2:8        (ACCESS 11:2:2)

18

PAGER
11:3:0    HAVE YOU PRACTICED ONE OF YOUR RELAXATION EXERCISES TODAY?
          IF YES, PLEASE PRESS 1.  IF NO, PLEASE PRESS 2.

11:3:1    IF 2:       IF YOU WOULD LIKE ME TO CALL YOU TO GUIDE YOU
                      THROUGH A RELAXATION EXERCISE PLEASE PRESS THE
                      # KEY.

11:3:2                IF # PRESSED:  IF I CAN CALL BEFORE 8 PM, PLEASE
                                     PRESS 1.  IF YOU PREFER I CALL AFTER
                                     8 PM, PLEASE PRESS 2.  (LOAD TIME)

(IF 11:3:1 CHOSEN)

PHONE

11:4:0                Hello, (Name).  If you would like to perform a
                      progressive relaxation exercise, please Press 1.
                      If you wuld rather do an autogenic training
                      exercise, please Press 2.  If you prefer to do a
                      deep-breathing "letting go" exercise, Press 3.  To
                      be guided through a visualization response, please
                      Press 5.  For active progressive relaxation, Press
                      6.  To hear the Levine Pain Meditation, Press 7.

IF 1:  (ACCESS 10:3:2)
                      IF 2:  (ACCESS 9:2:2)
                      IF 3:  (ACCESS 8:3:2)
                      IF 4:  (ACCESS 7:2:2)
                      IF 5:  (ACCESS 6:2:1)
                      IF 6:  (ACCESS 5:2:3)
                      IF 7:  (ACCESS 18:2:1)

DAY TWELVE

PAGER
12:0:0    (ACCESS 1:0:1)

PAGER
12:1:0    (ACCESS 1:1:0; REPEAT 2X AT SIX-HOUR INTERVALS.)

PHONE

12:2:0

(CC)

(Good morning; Good afternoon; Good evening), (Name). Maintaining negative thoughts about your condition can contribute to prolonging your suffering. Negative thoughts are always at hand during difficult times, ready to invade and sabotage your best efforts and intentions to improve. There have probably been times in the past -- and will be times in the future -- when you've said to yourself: "Forget it, it's hopeless, give up. I'll never feel better." This kind of thinking is self-defeating, and if you hold onto these kind of thoughts you'll have real difficulties making progress. If you sometimes find yourself dwelling on negative thoughts regarding your condition, please
    Press 1 for yes, or
    Press 2 for no.

12:2:1    IF YES:    That's OK, (Name); it's natural. But negative thoughts have the effect of increasing your anxiety and pain. Because they focus on catastrophe and resentment, negative thoughts create a reality where the worst appears to be inevitable and you are its helpless victim. The natural reaction to this grim scenario is for your body to tense up with fear and anger. As your body tightens, your pain increases.

(CC)      Now, (Name), it will be very helpful to you if you can recall and make a list of your typical negative thoughts about your condition. Some common examples are: "I'll never get better; this is going to get worse and drive me crazy; no one understands my pain; I'll never enjoy life again; it's my fault." Perhaps these sound familiar. You likely have other negative thoughts you can think of. If you're open to making this helpful list, please
    Press 1 for yes, or
    Press 2 for no.

| | | | |
|---|---|---|---|
| 11:2:2: | | IF YES: | Wonderful, (Name). Take your time, be honest with yourself, and don't worry: your list is private; no one will see it. Afterward, review your list and consider how you may be making things more difficult for yourself. Consider -- don't condemn. The purpose of this exercise is to illustrate your thinking, not cloud it with guilt and _more_ negative thoughts. Thank you. |
| 12:2:3 | | IF NO: | That's OK, (Name). Please call your counselor, though, for further insight. |
| 12:2:4 | IF NO: | | That's wonderful, (Name). A positive state of mind in concert with your exercises, will work as a catalyst toward relief of your discomfort. Keep it up! |

PAGER

12:3:0    (ACCESS 11:3:0)

21

(CLIENT'S OPTED 12:2:1)

DAY THIRTEEN

PAGER
13:0:0    (ACCESS 1:0:1)

PAGER
13:1:0    (ACCESS 1:1:0; REPEAT 2X AT SIX-HOUR INTERVALS.)

PHONE

13:2:0    (Good morning; Good afternoon; Good evening), (Name). Did you complete your list of negative thoughts? If you have, please
      Press 1 for yes, or
      Press 2 for no.

13:2:1    IF YES:    That's good, (Name).
13:2:2               If you'd like to learn ways to control negative thoughts, please
      Press 1

(CC)

IF 1:    There are three effective ways to replace your negative thoughts. Thought stopping, a proven method of behavioral therapy, is quite effective. Its function is to stop those bad thoughts cold by replacing them with quick, alternative thoughts which are realistic and positive in nature. Rather than dwell on why you're thinking negatively, you simply choose these positive responses and commit to them when you begin to notice yourself slipping into negative thinking. An example might be: when you hear yourself thinking, "Oh no, the pain is coming, I'm going to suffer," think instead, "the pain comes and goes; I'm on top of it; I can cope." I'm going to send you a suggested list of negative thought-stopping phrases. Put it by your bed, on the refrigerator, dashboard of your car -- wherever it will be handy when you need it. You can add your own positive, thought-stopping phrases to the list. Practice regularly; it works better and better the more you use it. You can even use what are known as howitzer mantras, angry rebuttal statements that substitute for your negative thoughts. The more angry and hostile your howitzer mantra, the better. Use

22

|  |  |  |
|---|---|---|
|  |  | expletives to add force and determination, if you care to. Make it sort of fun. "Stop this negative garbage!" "To hell with this bull!" "Cut the 'helpless' crap!" are examples. Can you think of more? If you'd like to continue learning about ways to replace negative thoughts, please <u>Press 1</u>. |
| 13:2:3 | <u>IF 1</u>: | Great, (Name). We'll speak tomorrow, thank you. |
| 13:2:4: | <u>IF NO</u>: | That's OK, (Name). Take whatever time you need. (ACCESS 13:2:2) |

<u>PAGER</u>
13:3:0   (ACCESS 11:3:0)

(CLIENT OPTED 13:2:4)

DAY FOURTEEN

PAGER
14:0:0   (ACCESS 1:0:1)

PAGER
14:1:0   (ACCESS 1:1:0; REPEAT 2X AT SIX-HOUR INTERVALS.)

PHONE

14:2:0   (Good morning; Good afternoon; Good evening), (Name). The second effective method for replacing your negative thoughts is the ABCD Model, developed by Drs. Albert Ellis, Aaron Beck and others. It has proven to be a very useful tool for confronting and altering your negative thoughts. Here's a summary of how it works: A is the "activating event" or stressor. B is your "belief system" -- your thoughts and attitudes about the stressful event. C stands for the (CC)     "consequences" -- your feelings, essentially -- and are a result of B. D is a way to "dispute" and change A, B, and C: You dispute the negative thinking you've discovered in your belief system which led to the consequences of feeling bad. This structured format may take some getting used to. With practice, however, you'll soon become familiar with your own typical patterns and be able to automatically and quickly dispute negative thinking that gets in your way. I'd like to send you a complete report on the ABCD Model so you can benefit fully from it. If you'd like to receive this information as soon as possible, please Press 1. Thank you.

PAGER
14:3:0   THERE ARE EIGHT STYLES OF NEGATIVE THINKING: 1. BLAMING; 2. 'SHOULD' STATEMENTS; 3. THINKING IN BLACK AND WHITE TERMS; 4. CATASTROPHIZIING; 5. CONTROL FALLACIES; 6. SUBJECTIVE REASONING; 7. FILTERING; 8. ENTITLEMENT. TO LEARN ABOUT THEM, PRESS 1 AND INFO WILL BE SENT TO YOU.

PAGER
14:4:0   (ACCESS 11:3:0)

DAY FIFTEEN

PAGER
15:0:0    (ACCESS 1:0:1)

PAGER
15:1:0    (ACCESS 1:1:0; REPEAT 2X AT SIX-HOUR INTERVALS.)

PHONE

15:2:0    (Good morning; Good afternoon; Good evening), (Name). Today I'd like to discuss the third way you can replace the negative thoughts that plague and prevent you from finding relief from your condition. First, however, please indicate by Pressing 1 if you have completed your list of negative thoughts that you typically experience. If you have not yet finished your list, please Press 2.

15:2:1    IF 1:    Wonderful, (Name). I'm glad you have.

15:2:2             The third way to replace your negative thoughts depends upon your having made this important list. Thought Analysis is a particularly effective method, one that requires that you dig a little deeper in studying your thought patterns and how they relate to your pain situation. I've saved it for last because it is often the most difficult step to take, but one that is key in ultimately coping with pain. It requires a high degree of honest self-assessment, and a non-defensive study
(CC)               of the choices you make about your pain. This is an entirely private exercise -- you will not be judged. The first step requires that you take some time to think about the various situations you've been in where pain was a factor. Now, (Name), the next step may be difficult for you but your doctor and our staff encourage you to encourage yourself: honestly ask yourself if there have been times when you needed, for whatever reason -- and there are no wrong answers -- to magnify your pain. Honestly ask yourself if there have been times when you were rewarded for remaining focused on your pain. In short, (Name), is it possible that by staying focused on your condition, your experience of being cared for and supported is enhanced? Does it help you to avoid unpleasant tasks, responsibilities or stressful events? Don't judge yourself harshly or feel guilty for the choices you may have made. The majority of people with chronic pain just like yours have all, at one time or another, used their pain to get something they needed. In fact, this phenomenon is so common it's considered normal behavior, so don't be too hard on yourself. It's OK. But you do need to work through this issue.

The increased awareness you'll develop as a result
                    of Thought Analysis is a tool to help you cope.
                    Acknowledging that you may, at times, be using your
                    condition for some form of gain will likely help
                    you to control it more effectively. If you're open
                    to taking some time to analyze your thoughts about
                    the possible benefits of pain, please
                    Press 1, for Yes, or
                    Press 2, for No.

15:2:3      IF 1:   Be proud of yourself, (Name).
15:2:4              This method may not be easy but it will
                    go a long way towards freeing yourself
                    from unconscious motivations which may be
                    subverting your genuine desire for im-
                    provement. If you feel comfortable doing
                    so, discuss this issue with a trusted
                    friend or family member. They truly want
                    to see you feeling better and will be
                    anxious to give you support. Do the
                    exercise. It'll pay off in pain relief.

15:2:5      IF 2:   That's all right, (Name). It may seem
                    ridiculous that you might have reasons
                    for staying in pain. Only a crazy person
                    would do that, right? Well, you don't
                    have to be crazy, just human with
                    frailties we all possess.
                    (ACCESS 15:2:4)

15:2:6  IF 2:  That's all right, (Name). But please complete your
               list soon so you can benefit from it.
               (ACCESS 15:2:2)

PAGER
15:3:0  (ACCESS 11:3:0)

DAY SIXTEEN

PAGER
16:0:0   (ACCESS 1:0:1)

PAGER
16:1:0   (ACCESS 1:1:0; REPEAT 2X AT SIX-HOUR INTERVALS.)

PHONE

16:2:0   (Good morning; Good afternoon; Good evening), (Name). Did
         you know that for many people with conditions just like
         yours, <u>pacing oneself</u> is an important aspect of managing
         discomfort? It's true. Sometimes, we just try to do too
         much -- and for good reasons. Enjoying gardening, as you do,
         you want to be able to do it as long as you did it before
         your problem developed. You may want to prove to yourself
         that you can perform just as before, so you work in the
         garden for 3 or 4 hours straight. The next day -- you're a
(CR)     wreck, really uncomfortable -- it'll be days before you can
         garden again. Now, what if, instead of trying to garden for
         long stretches at a time, you break it up into segments: An
         hour in the morning, an hour sometime after lunch, an hour
         before dinner. You'll have accomplished all you wanted to in
         the garden but without prolonged stress to your pain point.
         Or, on the job, take a short break every hour. You might be
         thinking: "How can I get anything done taking breaks all
         day?" To which you might respond: "A whole lot more than if
         I overdo it and have to take a day or two, or three off to
         recover!"

Pacing yourself is one of the simplest, most direct methods
         for helping you to remedy your discomfort level.

PAGER
16:3:0   PACE YOUR ACTIVITIES. LET SLOW, STEADY, AND SENSIBLE BE YOUR
         WATCHWORDS. THE RACE IS WON BY THE JOCKEY WHO KNOWS HOW TO
         HUSBAND A POWERFUL HORSE'S RESOURCES SO IT DOESN'T FADE IN
         THE BACKSTRETCH.

PAGER
16:4:0   (ACCESS 11:3:0)

27

DAY SEVENTEEN

PAGER
17:0:0    (ACCESS 1:0:1)

PAGER
17:1:0    (ACCESS 1:1:0; REPEAT 2X AT SIX-HOUR INTERVALS.)

PHONE

17:2:0    (Good morning; Good afternoon; Good evening), (Name).
          Shakespeare wrote: "The miserable have no other medicine but
          only hope." Sometimes, no matter how practical you are at
          managing you pain, it just gets you down, draining your
          energy and spirit. No matter how adept you've become at
          blocking negativity, it just creeps in, along with the pain.
          You may begin to feel frightened by your thoughts, and that
          scared feeling adds to your despair. Or, you experience the
(CR)      pain equivalent of a "bad hair day." These occasional bleak
(CC)      moods are not unusual. You are not alone. You need to deal
          with these feelings of hopelessness just as you would with a
          flare-up of severe pain. As soon as you realize that you are
          having a "hell day," take action immediately: Remember that
          this is a natural but temporary reaction -- it will pass.
          Remember that there are many reasons to be optimistic -- the
          millions of fellow sufferers who have learned to successfully
          manage their pain. Get up, <u>now</u> and change what you are
          doing. Do something that occupies your mind as well as your
          body. NEVER LOSE HOPE. Thank you.

PAGER
17:3:0    EMERGENCY Rx FOR DESPAIR: 1) DON'T PANIC -- DESPAIR COMES --
          AND GOES. THIS, TOO, SHALL PASS. 2) PREPARE AN ADVANCE
          ACTION STRATEGY: WHAT TO <u>DO</u> TO HELP GET YOU THROUGH THIS
          EPISODE. 3) <u>DO</u> <u>NOT</u>, REPEAT, <u>DO</u> <u>NOT</u> GO OFF BY YOURSELF.
          VISIT SOMEONE, OR PHONE A FRIEND. TALK ABOUT <u>ANYTHING</u> EXCEPT
          PAIN. ISOLATION FEEDS HOPELESSNESS.

PAGER
17:4:0    (ACCESS 11:3:0)

DAY EIGHTEEN

PAGER
18:0:0    (ACCESS 1:0:1)

PAGER
18:1:0    (ACCESS 1:1:0; REPEAT 2X AT SIX-HOUR INTERVALS.)

PHONE

18:2:0    (Good morning; Good afternoon; Good evening), (Name). Steven Levine, an expert who works with the terminally ill in pain, believes very strongly in directly confronting pain and despair. His theories and practices are rooted in classic Buddhist principles, particularly the concept of acceptance. His series of pain meditations have been found by many to ease their spirits as well as their discomfort. If you would like to take a few minutes now to practice one of his excellent meditation exercises, please Press 1. If you would prefer to wait until later to do this, please Press 2.

18:2:1    IF 1:    Excellent, (Name). This particular meditation is called "Opening Around Pain." Sit or lie down in a position you find comfortable. Allow yourself to settle into this position so your whole body feels fully present where it sits or lies...Bring your attention to the area of sensation that has been uncomfortable...Let your attention come wholly into that area. Let your awareness be present, moment to moment, to openly receive the sensations you feel...Allow the discomfort to be felt...moment to moment, new sensations seem to arise...Does the flesh seem to cramp against the pain?..Feel how the
(LPM)              body tends to grasp it in a fist, tries to close it off...Begin to allow the body to open all around that sensation...Feel the tension and resistance that comes to wall off the sensation...Don't push the pain away...Just let it be there...Feel how the body tries to isolate it...Tries to close it off... Picture that fist...Feel how the body is clenched in resistance...Feel how the body holds each new sensation...Begin to gradually open that closedness around sensation...The least resistance can be so painful...Open...Soften...All around the sensation ...Allow the fist, slowly, moment by moment, to open...To give space to the sensation...Let go of the pain...Why hold onto it a moment longer? Like grasping a burning ember, the flesh of the closed fist is seared in its holding...Open...Soften all around the sensation. Let the fist of resistance begin to loosen...to open. The palm of the fist softening...The fingers beginning to loosen their grip...Opening...All around the sensation...The fist loosening...Gradually opening. Moment to moment, letting go of the pain...release the fear that surrounds it...Notice any fear that has gathered around the pain...Allow the fist to melt. Let tension dissolve, so that the sensations can softly radiate out. Don't try to capture the pain ...Let it float free...No longer held in the grasp of resistance...Softening...Opening all around the sensation...The fist opening...The fingers, one by one, loosening...Let the pain soften...Let the pain be...Let go of the resistance that tries to smoother the experience...Allow each sensation to come fully into consciousness...No holding...No pushing away...The pain beginning to float free in the body...All grasping relinquished...Just awareness and sensation meeting moment to moment... Received gently by the softening flesh...the fist is open...the fingers loose...the fist dissolved back into the soft, open flesh...not tension...no holding...Let the body be soft and open...Let the sensation float free...Easy...Gently...Softening, opening all around the pain...Just sensation... Floating free in the soft, open body...

Now, slowly, slowly, without any tension, (ACCESS 6:2:1)

18:2:2    IF 2:    OK, Name). If I can call you <u>before</u> 8 PM, please <u>Press 1</u>. If I amy call you <u>after</u> 8 PM, please <u>Press 2</u>. Thank you.

<u>PAGER</u>
18:3:0    (ACCESS 11:3:0)

DAY NINETEEN

PAGER
19:0:0    (ACCESS 1:0:1)

PAGER
19:1:0    (ACCESS 1:1:0; REPEAT 2X AT SIX-HOUR INTERVALS.)

PHONE

19:2:0    (Good morning; Good afternoon; Good evening), (Name). This
          is Dr. (Name). I just wanted to follow-up on something your
          LifeStar counselor discussed with you the other day. It's
          the phenomenon of "secondary gains," when people in severe
          discomfort subconsciously find a benefit or benefits to
          remain in pain. (Name), it's so common; I've seen it many
          times. And, importantly, I've seen people who suffer
(URP)     transform their lives for the better when they begin to
          recognize how they -- through no conscious desire -- are
          aiding and abetting their discomfort. You don't have to be a
          slave to suffering -- you can turn the tables on it, become
          the master of this tyrant. It's a fact, one that has been
          proven time and time again. You have the inner power to
          overcome. I'm with you on this, every step of the way. You
          can do it. You will do it. I believe in you. I know you
          really don't want to be in pain one moment more. Be honest
          with yourself. I trust you. Trust yourself. We'll speak
          again soon, (Name). Thank you.

PAGER
19:3:0    YOU CAN ENDURE A PAINFUL EXISTENCE OR YOU CAN LIVE LIFE FULLY
          BY HONESTLY COPING WITH DISCOMFORT. REJECT HELL. CHOOSE
          LIFE.

PAGER
19:4:0    (ACCESS 11:3:0)

DAY TWENTY

PAGER
20:0:0    (ACCESS 1:0:1)

PAGER
20:1:0    (ACCESS 1:1:0; REPEAT 2X AT SIX-HOUR INTERVALS.)

PHONE
20:2:0    (Good morning; Good afternoon; Good evening), (Name). I'd very much like it -- and I firmly believe that you'll find it valuable -- if you'd take a little time today to make a list for yourself. This list will help all of us -- you, me and
(SGA)     Dr. (Name) in further planning and carrying out your pain management program.

Please divide a sheet of paper into two columns. In one column, please list your pros or advantages for remaining in pain. Pros might be: don't have to work; get a lot of attention; sympathy; great excuse to get out of obligations, etc. In the other column, please list your cons or disadvantages to remaining in pain. Cons might be: it hurts; decreased income due to work absence; makes me feel powerless; can't be independent, etc. Your list is totally private: no one but no one, including Dr. (Name) or I will ever know the exact content of your list. When you're through, carefully go over your list. Make additions if necessary. This list is very important, (Name), so please indicate your willingness to make it by Pressing 1. Thank you, (Name). I'll call you later today to follow-up, so please have it ready. Speak to you later.

20:2:1    IF NO BUTTON PUSHED:    Please contact your counselor for further insight. Thank you.

PHONE
20:3:0    Hello, (Name). If you've completed your list of pros and cons for remaining in pain, please
          Press 1 for Yes, or
          Press 2 for No.

20:3:1    IF YES:   Good work! Now please have your list in front of you...Press the # key when you do. Fine. Now please count up the number of pros on your list and enter that number now. Thank you, (Name). Now please total the number of cons on your list and enter that number now. You listed (ACCESS NUMBER) pros and (ACCESS NUMBER) cons. If this is correct, please Press the * key. Thank you.

You may recognize this list of pros and cons for remaining in pain as a variation on the Thought Analysis technique for replacing negative thoughts that we discussed last week. I will periodically ask you to make this list of pros and cons so you have a way to assess your thoughts on your relationship to pain. Virtually everyone suffering from chronic pain finds relief, over time, when the list of disadvantages to being in pain outweighs the list of advantages, and they act based upon all their perceived disadvantages. I'm proud of you, (Name). This list you've made is not an easy task. Give yourself a reward today.

If you would like to review the material on Thought Analysis, please Press 1.

20:3:2     IF 1:     (ACCESS 15:2:2)

20:3:3     IF NO BUTTON PUSHED:     Thank you, (Name). I'll speak to you soon.

20:3:4     IF NO:     That's all right, (Name). I'll call you later to go over it with you. If I can call before 8 PM, please Press 1. If you prefer that I call after 8 PM, please Press 2.

(ACCESS 20:3:0 for later call.)

PAGER
20:4:0     (ACCESS 11:3:0)

DAY TWENTY-ONE

PAGER
21:0:0    (ACCESS 1:0:1)

PAGER
21:1:0    (ACCESS 1:1:0; REPEAT 2X AT SIX-HOUR INTERVALS.)

PHONE

21:2:0    (Good morning; Good afternoon; Good evening), (Name). Today, let's have a little fun, OK? We're going to do a survey which we'll repeat occasionally. The survey is based upon the Pain Coping Strategies Questionnaire developed in 1983 by Rosenstiel and Keefe. It will help you, help Dr. (Name), and help us get an accurate picture of your situation so we can all work together to ease your suffering. To do this, I'll ask, "When in pain..." and then make a statement as if I were you. After each statement, please <u>Press 1</u> for Yes or <u>Press 2</u> for No. For instance, I might say, "When in pain, I get angry," and you respond by pressing 1 for Yes, or 2 for No. Are you ready to begin? Please <u>Press the # key</u> if you are ready. OK, (Name). Remember, <u>Press 1</u> for Yes, or <u>2</u> for No.

(CS)

<u>When in pain</u>,
- I count numbers in my head or run a song through my mind.
- I try to think of something pleasant.
- I think of things I enjoy doing.

<u>When in pain</u>,
- I try to feel distant from the pain, almost as if the pain was in someone else's body.
- I just think of it as some other sensation, such as numbness.
- I pretend it is not a part of me.

<u>When in pain</u>,
- It is terrible and I feel it is never going to get any better.
- It is awful and I feel it overwhelms me.
- I feel I can't stand it anymore.

If you would like to continue with this survey, <u>now</u>, please <u>Press the # key</u>. If you would prefer to continue later today, <u>please Press the * key</u>.

21:3:1    IF #:    Wonderful, (Name), let's go on.

21:3:2             <u>When in pain</u>,
                   - I don't think about the pain.
                   - I tell myself it doesn't hurt.
                   - I ignore it.

When in pain,
- I pray to God it won't last long.
- I have faith that someday there will be a cure for my pain.
- I rely on my faith in God.

When in pain,
- I tell myself to be brave and carry on despite the pain.
- I tell myself that I can overcome the pain.
- I see it as a challenge and don't let it bother me.

When in pain,
- I try to be around other people.
- I do something I enjoy, such as watching TV, or listening to music.
- I do something active, like household chores, projects or a hobby.

That's it, (Name). Thank you for participating. We'll speak again soon to discuss your responses and what they mean. Take care, and remember: reject hell, choose life.

21:3:3  IF *:  That's fine, (Name). If I can call you before 8 PM, Press 1. If you prefer that I call back after 8 PM, Press 2. (Load time for later call.)

PHONE  (If client opts 21:3:3)

21:4:0  Hello, (Name). Let's continue our survey now. Remember, at the end of each statement, Press 1 for Yes, or Press 2 for No. OK? Let's begin.

(ACCESS 21:3:2)

PAGER
21:5:0  (ACCESS 11:3:0)

DAY TWENTY-TWO

PAGER
22:0:0     (ACCESS 1:0:1)

PAGER
22:1:0     (ACCESS 1:1:0; REPEAT 2X AT SIX-HOUR INTERVALS.)

PHONE
22:2:0     (Good morning; Good afternoon; Good evening), (Name).
           Yesterday, when we did the survey together, you may have
           recognized that many of the statements were actually
           strategies to help you control your pain. For example: "When
           in pain, I count numbers in my head or run a song through my
           mind." That is an attention diversion method. You may
           recall that when we first began, I mentioned diversion, or
(CS)       distraction, as a key technique in pain management. I asked
           you to make some informal notes to yourself recalling situ-
           ations in your own life where you unconsciously distracted
           yourself from pain with another stimulus, like the one I
           mentioned above. Yesterday, you said yes to the statement:
           (UNLOAD RESPONSE: "When in pain I try to think of something
           pleasant.") That's an excellent distraction technique. If
           you've had success with it, by all means continue. You can
           also incorporate, if you wish, thinking of things you enjoy
           doing, or, like above, counting numbers, or running a song
           through your mind. Those three techniques can be quite
           effective. They all involve a mental distraction. If you
           would enjoy learning a few methods of physical distraction
           now, please Press 1. If you would prefer learning methods of
           physical distraction from pain later, please Press 2.

22:2:1   IF 1:   Wonderful, (Name). Let's continue.

22:2:2           Methods of physical distraction from pain involve
                 simple, everyday activities that take your mind off
                 your discomfort. For instance, yesterday you
                 answered yes to the statement: (UNLOAD RESPONSE:
                 "When in pain I try to be around other people.")
                 That's a wonderful distraction technique. You can,
                 if you wish, incorporate doing something active,
                 like chores, projects, or a hobby; and doing
                 something you enjoy, like watching TV or listening
                 to music. All these involve some form of action or
                 doing, in contrast to mental distraction techniques
                 which involve thinking. The important thing to
                 remember, no matter what distraction technique you
                 use, is to get your mind off your discomfort.
                 Thank you, (Name). Speak to you later.

22:2:3   IF 2:   (ACCESS 20:3:3)

PHONE      (If client opts 22:2:3)

22:3:0     Hello, (Name). Let's continue our discussion of distraction techniques. Earlier, I reviewed <u>mental</u> distraction. (ACCESS 22:2:2)

PAGER
22:4:0     (ACCESS 11:3:0)

DAY TWENTY-THREE

PAGER
23:0:0    (ACCESS 1:0:1)

PAGER
23:1:0    (ACCESS 1:1:0; REPEAT 2X AT SIX-HOUR INTERVALS.)

PHONE
23:2:0    (Good morning; Good afternoon; Good evening), (Name). Everyone perceives pain differently. What might be agony for one person, may be felt merely as an unpleasant annoyance by another. How one _interprets_ painful sensations varies from individual to individual, also. I'd like to review with you how you can reduce your pain by _reinterpreting_ it, but first, one quick question. Do you understand the principle of pain
(CS)      distraction that you learned yesterday? If you know what pain distraction is, and recall the pain distraction methods I suggested, please _Press 1_ for Yes. If you would like to review this material, please _Press 2_.

23:2:1    IF 1:    Excellent, (Name). Use these pain distraction techniques whenever necessary. You can probably come up with a few of your own that will be effective.

23:2:2             Now, let me introduce you to some simple, practical ways you can decrease your suffering by reinterpreting your pain sensations. You may recall from the survey, a series of three statements: "When in pain: I try to feel distant
(CS)               from the pain, almost as if the pain was in someone else's body; I just think of it as some other sensation, like numbness; I pretend it is not a part of me." You said yes to (UNLOAD ANSWER: "I think of it as some other sensation.") You may have, on your own, come up with this method, or recalled the Steven Levine meditation you did a little while back called "Opening Up to Pain" which, essentially, guides you through a reframing or reinterpretation of your suffering. In any case, reinterpreting pain sensations is an important, effective way to alter how pain affects you. By thinking differently about the nature of
(CS)               your pain, you can change the way you experience it. It requires focus and practice but will work. If you would like to practice the Steven Levine meditation, "Opening Up to Pain," as a helpful way to review, or reinterpret your sensation of pain, please _Press 1_. If you would enjoy reviewing some more of your responses to the survey, please _Press 2_. If you would like to end our session today, please _Press 3_.

| | | |
|---|---|---|
| 23:2:3 | IF 1: | (ACCESS 18:2:1) |
| 23:2:4<br><br>(SL)<br>(CS) | IF 2: | Self-efficacy, the belief that you have the power to do something you wish to do is another pain coping strategy. In the survey, the following statements of self-efficacy were presented: "When in pain, I tell myself to be brave and carry on despite the pain; I tell myself that I can overcome the pain; I see it as a challenge and don't let it bother me. You said yes to: (UNLOAD ANSWER: "No yeses chosen") |
| 23:2:4<br><br>(CS) | IF 1 OR MORE YESES: | Remaining positive in the face of adversity and believing that you have the power to change is an important asset in your struggle to cope with pain. Practice using positive statements of self-efficacy. Perhaps you can think of others. It will give you inner comfort and relief. Thank you. Speak to you soon. |
| 23:2:5 | (IF NO YESES): | (ACCESS 23:2:4) |
| 23:2:6 | IF 3: | That's OK, (Name). We'll speak later. |
| 23:2:7 | IF 2: | (ACCESS 22:2:0) |
| PAGER<br>23:3:0 | (ACCESS 11:3:0) | |
| PAGER<br>23:4:0 | (ACCESS 1:0:1) | |

39

DAY TWENTY-FOUR

PAGER
24:0:0      (ACCESS 1:0:1)

PAGER
24:1:0      (ACCESS 1:1:0; REPEAT 2X AT SIX-HOUR INTERVALS.)

PHONE
24:2:0      (Good morning; Good afternoon; Good evening), (Name). When something bad happens to us, we all have a natural tendency to dwell on the worst possible outcome, to exaggerate the circumstance beyond reality. In short, we tend to turn a negative event into a full-blown catastrophe. "Catastrophizing" is one of the eight recognized styles of cognitive distortion, forms of negative thinking that can severely hamper our ability to clearly and objectively assess
(CS)        our relationship with a person or event. The survey that you responded to the other day contained three "catastrophizing" statements: "When in pain: it is terrible and I feel it is never going to get any better; it is awful and I feel that it overwhelms me; and last, I feel I can't stand it anymore. You said yes to (UNLOAD RESPONSES: Last two).

In the second week of our working together, I sent you information concerning catastrophizing and the seven other styles of negative thinking. If you have read this material, please <u>Press 1</u>. If you have not yet had a chance to review this information, please <u>Press 2</u>. If you have not received this information, please <u>Press 3</u>.

24:2:1  IF 1:   Excellent, (Name).

24:2:2          We've spent time recently discovering how negative thinking can keep you in pain, and even make it worse. When you find yourself dwelling on a catastrophic thought, try using one of the methods of replacing negative thoughts that you've learned. (ACCESS 13:2:2; 14:2:0; 15:2:2)

24:2:3  IF 2:   That's OK, (Name), but please review this material soon so you can benefit from it. (ACCESS 24:2:2)

24:2:4  IF 3:   I'm sorry, I'll see that this information is sent to you today, (Name) (ACCESS 24:2:2)

PAGER
24:3:0      (ACCESS 11:3:0)

DAY TWENTY-FIVE

PAGER
25:0:0     (ACCESS 1:0:1)

PAGER
25:1:0     (ACCESS 1:1:0; REPEAT 2X AT SIX-HOUR INTERVALS.)

PHONE

25:2:0     (Good morning; Good afternoon; Good evening), (Name). Two of the most powerful medicines to cope and combat pain can't be prescribed by your doctor. They don't come in a bottle, are not pills or capsules. They have no side effects. They are free.

(CS)       The power of faith and hope in coping and controlling low back pain like yours is documented. In 1986, Keefe & Doba, contrasting patients with low back pain and patients with pain in other areas of the body, found that the patients with low back pain used significantly more diversion and praying and hoping strategies than the other group. Further, while diversion strategies in the low back pain group were effective in taking their minds off their pain, only praying and hoping were associated with <u>decreased</u> pain.

I'd like, at this time, to go over your survey responses as they relate to praying and hope. If you would like to do this <u>now</u>, please <u>Press 1</u>. If you would prefer that we discuss this <u>later</u>, please <u>Press 2</u>.

25:2:1  IF 1:   Thank you, (Name), let's continue.

25:2:2          In the survey, three statements of praying and hoping were given: "When in pain: I pray to God it won't last long; I have faith that someday there will be a cure for my pain; I rely on my faith in God." You said yes to (UNLOAD ANSWER: "I have faith that someday there will be a cure for my pain.").

(CR)
(CC)            Further, hope and prayer are all aspects of a positive attitude, and as we've learned, a positive attitude is fundamental to managing and decreasing your pain. Research by Dr. Martin Seligman, presented in his books, <u>Learned Helplessness</u>, and <u>Learned Optimism</u>, demonstrates a clear relationship between belief and outcome, or the phenomenon of self-fulfilling prophecy. If you believe something will turn out badly for you, it almost surely will; conversely, believing that a particular goal, condition or event will turn out well, almost always ensures that, indeed, it will. Faith, hope and prayer are all tied into a belief in personal

41 control: that an individual has the ability to influence or shape their future. You have this ability within you. Tap into it as a wellspring of personal power.

You can probably come up with a personal prayer, declaration of faith, or message of hope that can be yours alone, if you are so inclined. If you are, please do. If you would find it comforting to listen to one specially created for LifeStar, please Press the # key now.

IF NO KEY PUSHED:

Thank you, (Name) for your time today. I'll speak to you later.

25:2:3  IF #:  Thank you. If you would like to hear a prayer, please Press 1. If you prefer to listen to a declaration of faith, please Press 2. If you would rather hear a message of hope, please Press 3.

25:2:4  IF 1:  Dear God, give me the strength to endure and overcome my suffering. Let your soaring spirit come into me to ease my burden and lift my heavy heart. Allow the supreme mysterious power that is Yours alone to work within me, to calm and subdue my hurting, to comfort and support me during these difficult times. Turn my tears into sweet water that will wash away my anguish and extinguish the fire in my body. Draw me out of this harsh exile of pain and darkness and lead me to the soft light of peace and well being. I am wholly, but only human. You are whole, the One and only God. I pray for Your grace and thank You for my life. Amen.

(CS)

If you would like a copy of this prayer to be sent to you, please Press 1. If you would also like to receive a copy of the Pain Coping Strategies Survey you responded to, please Press 2. Thank you. Speak to you soon.

| | | |
|---|---|---|
| 25:2:5 | IF 2: | I have faith that if I truly want to overcome my suffering a way will be found for me to do so. I have faith that my doctor will help me as much as possible, that LifeStar will always be here for me if I so desire, and that my friends and family will encourage and support my efforts to successfully manage my pain. I have faith in my heart that there is much I can do on my own to make my life more comfortable, and can foresee a time in the future when my suffering will have surrendered to the pleasures of a full life, and my pain will be reduced, at worst, to a mere nuisance, an annoying little fly I can swat away. My faith in the future is strong, and with time, patience, and practice my pain will slip slowly into the past. |
| | | If you would like a copy of this declaration of faith to be sent to you, please <u>Press 1</u>. If you would also like to receive a copy of the Pain and Coping Strategies Survey you responded to, please <u>Press 2</u>. |
| | | Thank you. Speak to you later. |
| 25:2:6 (CS) | IF 3: | Someday, I will once again be able to feel the joy of simply being alive and free of discomfort. Someday, I will be able to smile and not feel my lips tighten, be able to laugh without pain crying out, and be able to move without cursing my body. Someday, I will forget myself, bend down to smell a flower, and not be punished because I love the scent of new marigolds in blossom within rich, dark soil. Someday, I will be able to dance with life again, be released, and move with the rhythms of the world. Someday, I will awaken and | arise afresh, my movements supple. I will stand, suffused with well being, and face the promised dawn. One morning, the sun will rise and the pain will set, my dark moon of suffering vanquished by a new horizon...

If you would like to have a copy of this message of hope sent to you, please <u>Press 1</u>. If you would also like to receive a copy of the Pain and Coping Strategies Survey you responded to, please <u>Press 2</u>.

Thank you. Speak to you later.

25:2:7   IF 2:   That's all right, (Name). If I can call you <u>before</u> 8 PM, please <u>Press 1</u>. If you prefer that I call you <u>after</u> 8 PM, please <u>Press 2</u>. (Load time for later call).

PAGER
25:3:0   (ACCESS 11:3:0)

PHONE
25:4:0   Hello, (Name). Let's now go over your survey responses with respect to hope and praying.
(ACCESS 25:2:2)

DAY TWENTY-SIX

PAGER
26:0:0 (ACCESS 1:0:1)

PAGER
26:1:0 (ACCESS 1:1:0; REPEAT 2X AT SIX-HOUR INTERVALS.)

PHONE

26:2:0 (Good morning; Good afternoon; Good evening), (Name). You've learned a great deal recently about the necessity of controlling negative thoughts and how to do so. Its importance cannot be underestimated. So, too, the importance of positive thinking, for example, having faith and hope that you <u>will</u> be able to successfully manage your pain. I want to encourage you to think positively, but more so, I'd like you to encourage yourself. Do you remember the "Thought Stopping" technique to replace negative thoughts when they occur with positive statements? I believe you'll find it very rewarding to work on a variation of this technique. It's called self-reinforcement, and it works quite simply.

(RM)
(CS) When you find yourself aware of thinking positively about yourself or your pain problem, <u>reward yourself</u>. You can do this many ways. The most immediate, and perhaps most effective way to reward yourself for positive thoughts is to repeat a positive statement, or series of statements, praising yourself <u>right then and there</u>. You may do it silently or aloud. The important thing is do it as soon as possible whenever you have a positive thought. Examples of positive statements of self-praise might be a simple but forceful and enthusiastic "YES!" or "All right, (Name)!" as if you've just scored a touchdown, or hit a homerun, for, indeed, every time you have a positive thought, you <u>have</u> scored points. Conversely, every time you have a negative thought, it's like the other team has scored. So, who's going to win the game? You or the other team?

Other examples of positive statements of praise might run the gamut from a silly but heartfelt "Atta boy! That's a <u>good</u>, <u>good</u> boy," as if you were praising your child or dog, (UNLOAD DOG'S NAME: "Max"), to a more formal but no less encouraging, "Good for you, (Name). You're a good man and deserve good things in life." I'm sure you can think of a short list of positive statements to reward yourself for positive thinking, that will work for you. Are you open to taking a little time today to make this helpful list? If you are, please <u>Press 1</u>. If not, please <u>Press 2</u>.

26:2:1 IF 1: That's wonderful, (Name).

26:2:2 I'm sure that sometimes making these kinds of therapeutic lists seems sort of juvenile and simplistic, and a big pain (if you don't mind the

45

P-word!). They are, however, quite effective, their usefulness demonstrated time again in pain management research. So, I encourage and applaud any efforts you make toward making this list and any others that might be appropriate to your condition. Now, (Name). If you would like to learn more about self-reinforcement of positive thinking, right now, please Press the # key. If you would prefer that I call you later so that we can continue, please Press the * key.

26:2:3    If #:    OK, (Name), let's go on.

26:2:4

(RM)    Do you have a favorite treat, whether food, buying a good book to read, or just spending a little money on yourself for something perhaps frivolous but no less desirable? Good! Now, whenever you become aware of having positive thoughts about yourself or your pain problem, indulge yourself -- eat that treat, buy that book you've been wanting to read, or that garden tool you've been meaning to get. Use these rewards in combination with positive self-statements. For instance, it might not be practical and healthy to eat a brownie after each positive thought you have, so you might try making a game of it. Every time you have a positive thought, repeat a positive statement of self-praise to yourself. Keep score, one point for each positive thought. When you've accumulated five (or however many you choose) points, then eat that brownie, or buy that special little something for yourself. Perhaps you can think of other ways to use these two effective self-reward therapies? Thank you, (Name). Speak to you soon.

26:2:5    If *:    If I may call you before 8 PM tonight, please Press 1. If you prefer that I call you after 8 PM tonight, please Press 2. (Load time for later call).

26:2:6    IF 2:    That's all right, (Name), I understand (ACCESS 26:2:2)

PHONE
26:3:0    (If call back) Hello, (Name). Let's continue learning about self-reinforcement of positive thinking. (ACCESS 26:2:4)

PAGER
26:4:0    (ACCESS 11:3:0)

DAY TWENTY-SEVEN

PAGER
27:0:0    (ACCESS 1:0:1)

PAGER
27:1:0    (ACCESS 1:1:0; REPEAT 2X AT SIX-HOUR INTERVALS.)

PHONE

27:2:0    (Good morning; Good afternoon; Good evening), (Name). You've
          been in the program for over three weeks now, and I'd like to
          take a moment to congratulate you for your continued
          participation. Working <u>actively</u> to cope with your condition
          is not always easy. But as you've probably experienced in
(RM)      other areas of your life, the truly satisfying things in life
          are rarely easy to attain but always worth the effort. So, a
          big pat on the back and good for you, (Name)! You deserve
          it.

Now, (Name), the first week of the program I stressed the
          importance of setting realistic, attainable goals that were
(GS)      specific. If you would like to review this material on goal
          setting, please <u>Press 1</u>. If you'd like to continue <u>now</u>,
          please <u>Press 2</u>.

27:2:1    IF 1:    (ACCESS 4:2:0)

27:2:2    IF 2:    OK, (Name), let's continue.

By now you've probably given some thought to how
                   you want to live and what you want to do. If you
                   have a list handy, or can easily recall these
                   goals, please <u>Press 1</u>. If you need a little more
                   time to think about these issues and set goals for
                   yourself, please <u>Press 2</u>.

27:2:3    IF 1:        Terrific, (Name). I'm glad to hear
                       you've given this serious thought. What
                       I would like you to do <u>now</u> is choose one,
                       two, or three goals you've set for your-
                       self and record them in your LifeStar
                       Goal Book. Take a moment now. Are your
                       goals specific? Are they challenging yet
                       attainable? Have you set a time frame
                       for accomplishing them? Here's an ex-
                       ample of an appropriate goal: "I want to
                       figure out ways I can work in my garden
                       with minimal discomfort, and do it within
(GS)                   three weeks," or "I want to figure out
                       what kinds of work I can do that won't
                       irritate my back and will use my skills
                       and knowledge, and I want to have some
                       answers within thirty days." OK, (Name),

47

|  |  |  |
|---|---|---|
|  |  | take a moment now, and when you're ready to record <u>Press the # key</u>, and wait for the tone. When you've finished recording, <u>Press the * key</u>. All right? Begin whenever you're ready. (LOAD GOAL RECORDING.) Thank you, (Name). Speak to you later. |
| 27:2:4 | IF 2: | That's OK, (Name), take your time. But please follow-up at your earliest convenience. If you think you can have some goals set for yourself within the next <u>two days</u>, please <u>Press 1</u>. If you think you'll need <u>five days</u>, please <u>Press 2</u>. If you think you'll need <u>more than five days</u>, please <u>Press 3</u>. |
| 27:2:5 | IF 1: | That's great, (Name). I'll contact you two days from now and we'll go over your list of goals. Thank you. Speak to you soon. |
| 27:2:6 | IF 2: | That's great, (Name). I'll contact you five days from now and we'll go over your list of goals. Thank you. Speak to you soon. |
| 27:2:7 | IF 3: | I understand, (Name). You are likely experiencing some difficulty. That's OK. We can help. Please contact your counselor for assistance today. Thank you. Speak to you soon. |

<u>PAGER</u>
27:3:0    (ACCESS 11:3:0)

DAY TWENTY-EIGHT

PAGER
28:0:0     (ACCESS 1:0:1)

PAGER
28:1:0     (ACCESS 1:1:0; REPEAT 2X AT SIX-HOUR INTERVALS.)

PHONE

28:2:0     (Good morning; Good afternoon; Good evening), (Name). Recently, we discussed the importance of faith and hope in managing and decreasing your discomfort. A LifeStar prayer, declaration of faith, and message of hope were offered for your consideration and comfort. You chose to listen to a (UNLOAD ANSWER: Declaration of Faith). I'm wondering, (Name), if you'd be willing to give a little thought to creating a brief one or two sentence personal statement that reflects your faith in the future regarding your back problem. Your personal declaration of faith might be, for example, "I have faith that within six months I will lower my degree of suffering" or "I believe that with help I can get a handle on my level of pain." Nothing elaborate. Just a simple expression of your belief. If you're open to taking a little time today to think about and jot down your personal declaration of faith, please Press 1. If you need another day to think about this beneficial statement, please Press 2.

28:2:1     IF 1:    That's terrific, (Name). I'll call you later today and you can record it for placement into your personal LifeStar Journal, where it will be safe and secure and private. Then, if at some point you would like to "consult" with your innermost self, you can retrieve this personal article of faith and hear, in your own voice, how you felt at the time. Now, if I may call you back before 8 PM, please Press 1. If you prefer that I call you back after 8 PM, please Press 2. (Load time for later call.)

IF 2:    That's OK, (Name). I understand. I'll call you to follow-up. Thank you.

PHONE (IF 28:2:1 CHOSEN)
28:3:0     Hello, (Name). Have you had a chance to create your personal declaration of faith? If you have and are ready to record it into your LifeStar Personal Journal, please Press 1. If you would like me to call back later today, please Press 2. If you need more time and would prefer that I call back tomorrow, please Press 3.

| | | |
|---|---|---|
| 28:3:1 | IF 1: | Wonderful, (Name). |
| | | Now, when you're ready to record your statement, Press the # key, then wait for the tone. When you're finished with your statement, Press *. Thank you, (Name). Begin whenever you wish. |
| 28:3:2 | IF 2: | That's all right, (Name). At the tone, enter a time later today when I may call. If, for example, you wish me to call back at 7:30 tonight, punch in 7-3-0 and the letter P afterward for "PM." Thank you, (Name). Wait for the tone, then punch in your time. Speak to you later. |
| 28:3:3 | IF 3: | That's OK, (Name), I understand. I'll call back tomorrow to follow-up. Thank you. |

PAGER
28:4:0    (ACCESS 11:3:0)

DAY TWENTY-NINE

PAGER
29:0:0    (ACCESS 1:0:1)

PAGER
29:1:0    (ACCESS 1:1:0; REPEAT 2X AT SIX-HOUR INTERVALS.)

PHONE

29:2:0    (Good morning; Good afternoon; Good evening), (Name). This
          is Dr. (Name). A few weeks ago, your LifeStar counselor
          asked if you'd begun to consider getting some form of
          exercise so your discomfort wouldn't worsen. You were asked
          if staying in the best possible physical condition you could
(URP)     to minimize your suffering was important to you. You said
          yes, and were sent some written materials on the subject to
          read. Have you had an opportunity to do so? I sure hope so,
          because -- and I can't stress this enough, (Name) -- regular,
          careful exercise is a fundamental part of the recovery pro-
          cess for back problems such as yours, and this recovery
          process includes the lessening of your pain and suffering.
          Now, (Name), I'm your doctor. I know how difficult things
          are for you these days. Suffering is not fun. But, (Name),
          if you ever hope to live as fully as possible without suffer-
          ing -- and I know you do, everybody does -- you must take
          this step forward and begin to exercise now, or as soon as
          you possibly can. As someone who has spent a lot of time in
          the past working-out with weights, you may feel that you'll
          never be able to workout like you used to. Perhaps. But you
          will be able to workout, (Name), and all the efforts in the
          gym you've made through the years will not have been wasted.
          You'll be able to once again feel that good, strong, vibrant
          sensation after your workout -- and maintain youthful vigor
          and appearance. I want to make a note in your chart that
          you're going to start exercising again soon. Can I do that?
          If you can promise me that you'll begin to start a safe and
          supervised exercise program as soon as you can so I can go
          ahead and make a note in your records, please Press 1. If
          you need a little more time to make this critical decision,
          please Press 2.

29:2:1    IF 1:    Excellent, (Name), that's great to hear. I applaud
                   your decision; I know how concerned you probably
                   are about this subject. You've made the right
                   choice -- a choice to be as healthy and pain-free
                   as possible. Now, (Name), can I make a note that
                   you'll begin within the next ten working days? If
                   you'd like to get started on your exercise program
                   in less than two weeks, please Press 1. If it will
                   take you longer than two weeks to get started but
                   less than a month, please Press 2.

51

| | | | |
|---|---|---|---|
| 29:2:2 | IF 1: | | Terrific, (Name). I'll make a note on your chart that you're starting to exercise, and give you a call in two weeks to see how things are going. Congratulations, (Name). Speak to you soon. |
| 29:2:3 | IF 2: | | Terrific, (Name). I'll make a note on your chart that you're starting within a month and will give you a call soon to see how you're doing. Congratulations, (Name), speak to you soon. |
| 29:2:4 | IF 2: | | That's OK, (Name). I understand. Making important choices about your future can be difficult sometimes, particularly concerning your health. Perhaps I can help. I suspect that you may fear that if you begin to exercise you might hurt yourself further. This is highly unlikely if you are careful and have adequate supervision. It's possible you might feel some muscle soreness or achiness -- but don't confuse those expected and harmless sensations with the discomfort from your injury. And don't let those sensations make you stop exercising. They will subside as you continue to exercise, as will the discomfort from your injury. There is no question about it, (Name). You must start exercising soon. I'm going to go ahead and make a notation on your chart that you'll start to get some exercise within a month's time. If I'm making a mistake by doing so, please contact your LifeStar counselor so that they can send me an official notification. I hope that's not necessary. I sincerely want you to get better, don't you? Thank you, (Name), I'll stay in touch. |

PAGER
29:3:0   (ACCESS 11:3:0)

DAY THIRTY

PAGER
30:0:0   (ACCESS 1:0:1)

PAGER
30:1:0   (ACCESS 1:1:0; REPEAT 2X AT SIX-HOUR INTERVALS.)

PHONE

30:2:0   (Good morning; Good afternoon; Good evening), (Name). Often, in the aftermath of a back injury such as yours and the chronic pain that can result, it can appear to be impossible to perform common chores and household responsibilities that were once yours. Simply taking out the garbage can seem like an ordeal. Are there responsibilities around the house that you're no longer able to carry out? If your answer is <u>yes</u>, please <u>Press 1</u>. If carrying out your household chores is <u>not</u> a problem for you, please <u>Press 2</u>.

(ERE)
(CC)

30:2:1   IF 1:   I understand, (Name), and it's okay. But do you know that there are ways to do simple household chores that won't aggravate your discomfort? If, for instance, taking out the garbage is a problem for you there are a few things you can do to make it easier. If, for example, its weight is too heavy then take that into consideration and plan on taking out the garbage <u>before</u> the wastebasket or kitchen trashcan is full. Now that the weight problem is dealt with, perhaps bending over to pick it up remains a challenge. Solution? Don't bend over to pick it up, that puts strain on your lower back. Instead, bend down at the knees, stay as relaxed as possible, and keep your back as straight as possible. Use your leg power to lift. Now, hold it close to your body as you walk to the outdoor trashbin. Holding the load in this way also takes the stress of your back. I'm sure you can think of new ways to perform your household chores, if you give yourself a little time and accept that you are capable of carrying out most but perhaps not all of your household responsibilities. While everyone enjoys being pampered occasionally, few adults enjoy feeling helpless and dependent for very long; these emotions tend to erode self-esteem, promote feelings of guilt and frustration and ultimately develop into anger, anger that is more often than not directed inward toward oneself. That inner anger is stressful -- and as we've learned, stress aggravates pain. Now, I want you to choose one household responsibility that you formerly carried out. Think about how you might be able to do it by making a change here, a change there. Then do it. I believe you'll succeed. You (ERE)
(CC)

|  |  |  |
|---|---|---|
|  |  | will succeed. And the sense of satisfaction you'll experience will be invaluable. Reward yourself appropriately. This is a positive step forward. Thank you, (Name). Speak to you soon. |
| 30:2:2 | IF 2: | I'm so glad to hear that, (Name). I'm sure you must feel a wonderful sense of satisfaction that your discomfort hasn't prevented you from being active and involved in your home. Be judicious -- don't try to do _too_ much, just as much as you are capable of doing at this time. You can always increase your responsibilities over a period of time. So, (Name), good for you. Reward yourself. You deserve it. Thank you. Speak to you later. |

PAGER
30:3:0    (ACCESS 11:3:0)

I claim:

1. A system for interactive preventative medical guidance and commercial goal management comprising:
   a) polling means for creating a database of personalized input data indicative of an individual's particular behavioral issue;
   b) evaluation means for determining an individual's temporal behavioral stage from said database selected from one of a plurality of behavioral stages;
   (c) mediation means for determining from said evaluation means and said database a behavioral routine for changing said selected temporal behavioral stage;
   (d) program means including transmission means for delivering to said individual specific content based communication based on said behavioral routine determined by said mediation means for changing said selected temporal behavioral stage; and
   (e) feedback means for receiving an individual's response to said content based communication wherein said mediation means provides periodic reevaluation of said response for determining readjustment of said behavioral routine and said content based communication.

2. The system as specified in claim 1 wherein said polling means for creating said database comprising a compact disc and a compact disc player interfacing with a computer.

3. The system as specified in claim 2 wherein said evaluation means for determining an individual's temporal behavioral stage comprising a compact disc and a compact disc player that interfaces with a computer.

4. The system as specified in claim 1 wherein said mediation means for determining a behavioral routine is a physician.

5. The system as specified in claim 1 wherein said mediation means for determining a behavioral routine is a counselor.

6. The system as specified in claim 5 wherein said behavioral routine for changing said selected temporal behavioral stage utilizes guided imagery through prompts and ques delivered by said counselor.

7. The system as specified in claim 5 wherein said behavioral routine for changing said selected temporal behavioral stage utilizes systematic desensitization.

8. The system as specified in claim 1 wherein said plurality of behavioral stages comprises a precontemplation stage; contemplation stage; preparation stage; action stage; maintenance stage; and relapse stage.

9. The system as specified in claim 1 wherein said behavioral routine for changing said selected temporal behavioral stage comprises an overlearning technique.

10. The system as specified in claim 1 wherein said behavioral routine for changing said selected temporal behavioral stage comprises application of a generation effect.

11. The system as specified in claim 1 wherein said behavioral routine for changing said selected temporal behavioral stage utilizes refresher practice.

12. The system as specified in claim 1 wherein said behavioral routine for changing said selected temporal behavioral stage utilizes contextual variety.

13. The system as specified in claim 1 wherein said behavioral routine for changing said selected temporal behavioral stage utilizes delivery of an increased plurality of descriptive examples.

14. The system as specified in claim 1 wherein said behavioral routine for changing said selected temporal behavioral stage utilizes double-bind quizzes and questions to crystallize positive compliance.

15. The system as specified in claim 1 wherein said behavioral routine for changing said selected temporal behavioral stage utilizes an interactive quiz.

16. The system as specified in claim 1 wherein said behavioral routine for changing said selected temporal behavioral stage utilizes time and place shifting in delivering said individual specific content based communication.

17. The system as specified in claim 1 wherein said behavioral routine for changing said selected temporal behavioral stage integrates context-dependent memory for said individual's particular behavioral issue into said behavioral routine.

18. The system as specified in claim 1 wherein said behavioral routine for changing said selected temporal behavioral stage uses state-dependent memory for said individual's particular behavioral issue into said behavioral routine.

19. The system as specified in claim 1 wherein said behavioral routine for changing said selected temporal behavioral stage comprises means of awarding and crediting rewards from a predetermined deposit.

20. The system as specified in claim 1 wherein said feedback means for receiving said individual's response comprising an electronic weight scale that does not allow the individual to view his weight.

21. The system specified in claim 1 wherein said feedback means for receiving said individual's response comprising an olfactory unit to provide smells in association with said database.

22. The system specified in claim 1 wherein said feedback means for receiving said individual's response comprising a voice stress analyzer.

23. The system specified in claim 1 wherein said transmission means for delivering said individual content based communication and said feedback means for receiving said individual's response comprising using an interactive television system.

24. The system specified in claim 1 wherein said feedback means for receiving said individual's response comprising an EEG measuring and recording device.

25. The system specified in claim 1 wherein said transmission means for delivering said individual content based communication and said feedback means for receiving said individual's response comprising an interactive video system.

26. The system specified in claim 1 wherein said program means for delivering said individual specific content based communication addresses stored information from an optical disc.

27. The system specified in claim 1 wherein said transmission means for delivering said individual content based communication and said feedback means for receiving said individual's response comprises a cellular phone system.

28. The system specified in claim 1 wherein said transmission means for delivering said individual content based communication and said feedback means for receiving said individual's response comprises a dual tone multifrequency set having voice recognition.

29. The system specified in claim 1 wherein said transmission means for delivering said individual content based communication and said feedback means for receiving said individual's response comprises a Local Area Network (LAN).

30. The system specified in claim 1 wherein said transmission means for delivering said individual content based communication and said feedback means for receiving said individual's response comprises text and sound message software.

31. The system specified in claim 1 wherein said transmission means for delivering said individual content based communication and said feedback means for receiving said individual's response comprises asynchronized transfer mode (ATM).

32. The system specified in claim 1 wherein said transmission means for delivering said individual content based communication and said feedback means for receiving said individual's response comprises a software agent program having remote programming.

33. The system specified in claim 1 wherein said transmission means for delivering said individual content based communication and said feedback means for receiving said individual's response comprises a cellular digital packet data (CDPD) network.

34. The system specified in claim 1 wherein said transmission means for delivering said individual content based communication and said feedback means for receiving said individual's response comprises an interactive video system.

35. The system specified in claim 1 wherein said transmission means for delivering said individual content based communication and said feedback means for receiving said individual's response comprises a personal digital assistance.

36. The system specified in claim 1 wherein said transmission means for delivering said individual content based communication and said feedback means for receiving said individual's response comprises a wireless interactive personal communicator having the shape of a woman's compact.

37. The system specified in claim 1 wherein said transmission means for delivering said individual content based communication and said feedback means for receiving said individual's response comprises a wireless personal communicator.

38. The system specified in claim 1 wherein said transmission means for delivering said individual content based communication and said feedback means for receiving said individual's response comprises a wireless interactive personal communicator having the configuration of a wristband containing a two-way communication unit.

39. The system specified in claim 1 wherein said feedback means for receiving said individual's response comprises a timing device for measuring said individual response latency.

40. The system specified in claim 1 wherein said feedback means for receiving said program means including transmission means comprises a personalized monograph delivering said individual's specific content based communication.

41. The system specified in claim 1 wherein said program means including transmission means comprises a behavioral contract for delivering to said individual specific content based communication received from an earlier response.

42. An interactive preventative medical guidance system for use by a client comprising:
  a) means for recording and accessing a client's database that includes a client program which incorporates for each client, a calling schedule and personal identification number;
  b) means for reinforcing predetermined client behavior based upon said means for recording and accessing said clients database by use of an expert who determines for each client one of either specific motivational messages, stimuli or questions which are to be responded to by the client;
  c) a computer having means for accessing said client database and said client program, said computer producing in sequence, a digital telephone signal that corresponds to a client's telephone number, a digital client validation request signal and one of either said motivational messages, stimuli or questions determined by said expert as said means for reinforcing said predetermined client behavior that are only sent if said client's validation request signal is responded to by the client with a valid personal identification number,
  (d) means for converting digital signals produced by said computer to telephone tone signals that are sent to a client's dual tone multifrequency telephone set via a telephone network where said telephone set is queued to respond to the client's validation request, hear said motivational message(s) and to respond to said questions;
  (e) means for converting telephone tone signals originating at said client's telephone set to digital signals for application to and processing by said computer; and
  (f) means for permanently recording and evaluating all outgoing and incoming client communications for periodic reevaluation by said expert for updating said motivational messages, stimuli or questions determined by said expert as said means for reinforcing said predetermined client behavior.

43. The system as specified in claim 42 wherein said means for recording and accessing a client's database comprising a compact disc and a compact disc player interfacing with said computer.

44. The system as specified in claim 42 wherein said means for recording and accessing a client's program comprising a compact disc and a compact disc player that interfaces with said computer.

45. The system as specified in claim 42 wherein said computer comprising an IBM-AT compatible computer having an 80386 micro processor or equivalent including a Dialogic D41 4-line speech card.

46. The system as specified in claim 42 wherein said means for converting said digital signals from said computer to telephone tone signals comprising a digital/telephone tone signal converter having circuit means for performing the conversion in either direction.

47. The system as specified in claim 42 wherein said means for reinforcing a client's program comprising an electronic weight scale that does not allow the client to view his/her weight.

48. The system specified in claim 42 wherein said means for reinforcing a client's program comprising an olfactory unit to provide smells in association with said client database.

49. The system specified in claim 42 wherein said means for reinforcing a client's program comprising a voice stress analyzer.

50. The system specified in claim 42 wherein said means for reinforcing a client's program comprising using an interactive television system.

51. The system specified in claim 42 wherein said means for reinforcing a client's program comprising an EEG measuring and recording device.

52. The system specified in claim 42 wherein said means for reinforcing a client's program comprising an interactive video system.

53. The system specified in claim 42 wherein said means for reinforcing a client's program addresses stored information from an optical disc.

54. The system as specified in claim 42 wherein said mediation means for determining a behavioral goal routine is a peer.

55. The system as specified in claim 42 wherein said mediation means for determining a behavioral goal routine is a manager.

56. The system as specified in claim 42 wherein said mediation means for determining a behavioral goal routine is a supervisor of a manager.

57. The system specified in claim 42 wherein said transmission means for delivering said individual content based communication and said feedback means for receiving said individual's response comprises ISDN.

58. A method for an automated and interactive positive motivation system comprising the steps of:

(a) recording a client calling schedule and personal identification number for a client;

(b) storing said recording of said client calling schedule and said personal identification number in a client database;

(c) producing a digital telephone signal that corresponds to said recording and said storing of said personal identification number in accordance with said client calling schedule in said client database;

(d) converting said produced digital telephone signal to telephone tone signals in correspondence to said recording and said storing of said personal identification number in accordance with said client calling schedule in said client database;

(e) sending said telephone tone signals from said converting of said digital telephone signal in accordance to said recording and said storing of said client calling schedule in said client database to a client's dual tone multifrequency telephone set;

(f) comparing said telephone tone signals from said converting of said digital telephone signal corresponding to said personal identification number in said client database to a client's telephone tone signal input wherein if a match is found, a program means delivers one of either motivational messages, stimuli or questions to said client; and (g) processing said client's response to said motivational messages, stimuli or questions by said program means and permanently recording said client's response in said client database, whereby said client calling schedule in said client database is updated by said program means for producing and converting said digital telephone signal in accordance with said client calling schedule to deliver another set of said motivational messages, stimuli or questions to said client.

* * * * *